(12) United States Patent
Swyka et al.

(10) Patent No.: US 12,428,420 B2
(45) Date of Patent: Sep. 30, 2025

(54) TRICYCLIC HETEROCYCLES AS FGFR INHIBITORS

(71) Applicant: Incyte Corporation, Wilmington, DE (US)

(72) Inventors: Robert Swyka, Wilmington, DE (US); Evan Styduhar, Claymont, DE (US); Xin Li, Claymont, DE (US); Oleg Vechorkin, Wilmington, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 129 days.

(21) Appl. No.: 17/835,330

(22) Filed: Jun. 8, 2022

(65) Prior Publication Data

US 2023/0002384 A1 Jan. 5, 2023

Related U.S. Application Data

(60) Provisional application No. 63/208,661, filed on Jun. 9, 2021.

(51) Int. Cl.
| | | |
|---|---|---|
| *C07D 471/14* | (2006.01) |
| *A61K 31/4375* | (2006.01) |
| *A61K 31/444* | (2006.01) |
| *A61K 31/496* | (2006.01) |
| *A61K 31/506* | (2006.01) |
| *A61K 31/5377* | (2006.01) |
| *A61K 45/06* | (2006.01) |
| *A61P 35/00* | (2006.01) |
| *C07D 519/00* | (2006.01) |

(52) U.S. Cl.
CPC ........ *C07D 471/14* (2013.01); *A61K 31/4375* (2013.01); *A61K 31/444* (2013.01); *A61K 31/496* (2013.01); *A61K 31/506* (2013.01); *A61K 31/5377* (2013.01); *A61K 45/06* (2013.01); *A61P 35/00* (2018.01); *C07D 519/00* (2013.01)

(58) Field of Classification Search
CPC ............................ C07D 471/14; C07D 519/00; A61K 31/4375; A61K 31/444; A61K 31/496; A61K 31/506; A61K 31/5377; A61K 45/06; A61P 35/00
USPC ........................................................ 514/232
See application file for complete search history.

(56) References Cited

U.S. PATENT DOCUMENTS

| | | | |
|---|---|---|---|
| 850,370 | A | 4/1907 | Hynes |
| 3,894,021 | A | 7/1975 | Denzel et al. |
| 4,271,074 | A | 6/1981 | Lohmann et al. |
| 4,339,267 | A | 7/1982 | Levitt |
| 4,347,348 | A | 8/1982 | Chernikhov et al. |
| 4,402,878 | A | 9/1983 | D'Alelio et al. |
| 4,405,519 | A | 9/1983 | D'Alelio et al. |
| 4,405,520 | A | 9/1983 | D'Alelio et al. |
| 4,405,786 | A | 9/1983 | D'Alelio et al. |
| 4,460,773 | A | 7/1984 | Suzuki et al. |
| 4,874,803 | A | 10/1989 | Baron et al. |
| 4,940,705 | A | 7/1990 | Boshagen et al. |
| 5,159,054 | A | 10/1992 | Keller |
| 5,240,941 | A | 8/1993 | Bruneau |
| 5,480,887 | A | 1/1996 | Hornback et al. |
| 5,521,184 | A | 5/1996 | Zimmermann et al. |
| 5,536,725 | A | 7/1996 | Cullen et al. |
| 5,541,324 | A | 7/1996 | TenBrink et al. |
| 5,760,068 | A | 6/1998 | Talley et al. |
| 5,783,577 | A | 7/1998 | Houghten et al. |
| 5,845,025 | A | 12/1998 | Garito et al. |
| 5,994,364 | A | 11/1999 | Njoroge et al. |
| 6,465,484 | B1 | 10/2002 | Bilodeau et al. |
| 6,998,408 | B2 | 2/2006 | Pinto |
| 7,074,801 | B1 | 7/2006 | Yoshida et al. |

(Continued)

FOREIGN PATENT DOCUMENTS

| | | |
|---|---|---|
| CL | 2014003355 | 6/2015 |
| CL | 2015002628 | 8/2016 |

(Continued)

OTHER PUBLICATIONS

Yamani et al. European Journal of Medicinal Chemistry 2021, 210,112990, http://www.elsevier.com/locate/ejmech, "Discovery and optimization of novel pyrazole-benzimidazole, CPL304110, as a potent and selective inhibitor of fibroblast growth factor receptors FGFR (1-3)" (Year: 2021).*

(Continued)

*Primary Examiner* — Amy L Clark
*Assistant Examiner* — Liyuan Mou
(74) *Attorney, Agent, or Firm* — Fish & Richardson P.C.

(57) ABSTRACT

The present disclosure relates to tricyclic heterocycles, and pharmaceutical compositions of the same, that are inhibitors of the FGFR enzyme and are useful in the treatment of FGFR-associated diseases such as cancer.

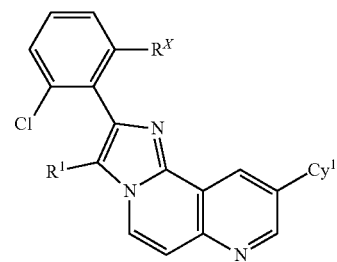

2 Claims, No Drawings
Specification includes a Sequence Listing.

(56) References Cited

U.S. PATENT DOCUMENTS

| | | | |
|---|---|---|---|
| 7,125,880 B1 | 10/2006 | Chen | |
| 7,488,802 B2 | 2/2009 | Collins et al. | |
| 7,618,975 B2 | 11/2009 | Cai et al. | |
| 7,642,255 B2 | 1/2010 | Sim | |
| 7,648,973 B2 | 1/2010 | DeLuca et al. | |
| 7,943,743 B2 | 5/2011 | Korman et al. | |
| 8,008,449 B2 | 8/2011 | Korman et al. | |
| 8,168,757 B2 | 5/2012 | Finnefrock et al. | |
| 8,217,149 B2 | 7/2012 | Irving et al. | |
| 8,754,114 B2 | 6/2014 | Yao et al. | |
| 8,759,398 B2 | 6/2014 | Nelson | |
| 8,889,711 B2 | 11/2014 | Bedjeguelal | |
| 9,266,892 B2 | 2/2016 | Zhuo et al. | |
| 9,388,185 B2 | 7/2016 | Lu et al. | |
| 9,533,954 B2 | 1/2017 | Yao et al. | |
| 9,533,984 B2 | 1/2017 | Sun et al. | |
| 9,580,423 B2 | 2/2017 | Lu et al. | |
| 9,611,267 B2 | 4/2017 | Wu et al. | |
| 9,708,318 B2 | 7/2017 | Lu et al. | |
| 9,745,311 B2 | 8/2017 | Lu et al. | |
| 9,801,889 B2 | 10/2017 | Lu et al. | |
| 9,890,156 B2 | 2/2018 | Lu et al. | |
| 10,016,348 B2 | 7/2018 | Lu et al. | |
| 10,040,790 B2 | 8/2018 | Sun et al. | |
| 10,131,667 B2 | 11/2018 | Wu et al. | |
| 10,208,024 B2 | 2/2019 | Andrews et al. | |
| 10,213,427 B2 | 2/2019 | Yao et al. | |
| 10,214,528 B2 | 2/2019 | Lu et al. | |
| 10,251,892 B2 | 4/2019 | Sokolsky et al. | |
| 10,308,644 B2 | 6/2019 | Wu et al. | |
| 10,350,240 B2 | 7/2019 | Gore et al. | |
| 10,357,431 B2 | 7/2019 | Staric et al. | |
| 10,450,313 B2 | 10/2019 | Lu et al. | |
| 10,611,762 B2 | 4/2020 | Jia et al. | |
| 10,632,126 B2 | 4/2020 | Lu et al. | |
| 10,669,271 B2 | 6/2020 | Wu et al. | |
| 10,738,048 B2 | 8/2020 | Lu et al. | |
| 10,813,930 B2 | 10/2020 | Yao et al. | |
| 10,851,105 B2 | 12/2020 | Wu et al. | |
| 10,947,230 B2 | 3/2021 | Sun et al. | |
| 11,014,923 B2 | 5/2021 | Lu et al. | |
| 11,053,246 B2 | 7/2021 | Wu et al. | |
| 11,173,162 B2 | 11/2021 | Sokolsky et al. | |
| 11,174,257 B2 | 11/2021 | Jia et al. | |
| 11,407,750 B2 | 8/2022 | Tao et al. | |
| 11,466,004 B2 | 10/2022 | Burn | |
| 11,607,416 B2 | 3/2023 | Vechorkin et al. | |
| 11,897,891 B2 * | 2/2024 | McCammant | A61P 35/00 |
| 11,939,331 B2 * | 3/2024 | Li | C07D 471/14 |
| 12,012,409 B2 | 6/2024 | Roach et al. | |
| 12,083,124 B2 | 9/2024 | Vechorkin et al. | |
| 2003/0078255 A1 | 4/2003 | Pinto | |
| 2003/0078277 A1 | 4/2003 | Hibi et al. | |
| 2003/0181622 A1 | 9/2003 | Chiu et al. | |
| 2004/0044012 A1 | 3/2004 | Dobrusin et al. | |
| 2004/0067948 A1 | 4/2004 | Hallett | |
| 2004/0097493 A1 | 5/2004 | Chen et al. | |
| 2004/0122029 A1 | 6/2004 | Liu et al. | |
| 2004/0127536 A1 | 7/2004 | Bhagwat et al. | |
| 2004/0127538 A1 | 7/2004 | Oinuma et al. | |
| 2004/0204427 A1 | 10/2004 | Chen et al. | |
| 2005/0009876 A1 | 1/2005 | Bhagwat et al. | |
| 2005/0070542 A1 | 3/2005 | Hodgetts et al. | |
| 2005/0148603 A1 | 7/2005 | Jimenez et al. | |
| 2005/0197340 A1 | 9/2005 | Arora et al. | |
| 2005/0222171 A1 | 10/2005 | Bold et al. | |
| 2006/0222637 A1 | 10/2006 | Bamdad | |
| 2006/0270849 A1 | 11/2006 | Nishino et al. | |
| 2007/0116984 A1 | 5/2007 | Park et al. | |
| 2007/0197510 A1 | 8/2007 | Ohmoto et al. | |
| 2007/0225286 A1 | 9/2007 | Ren et al. | |
| 2007/0280943 A1 | 12/2007 | Friedman et al. | |
| 2008/0249301 A1 | 10/2008 | Hornberger et al. | |
| 2009/0098086 A1 | 4/2009 | Zask et al. | |
| 2009/0099165 A1 | 4/2009 | Hurley et al. | |
| 2009/0099190 A1 | 4/2009 | Flynn et al. | |
| 2009/0105233 A1 | 4/2009 | Chua et al. | |
| 2009/0131467 A1 | 5/2009 | Kanazawa et al. | |
| 2009/0163545 A1 | 6/2009 | Goldfarb | |
| 2009/0246198 A1 | 10/2009 | Dong et al. | |
| 2010/0032626 A1 | 2/2010 | Akino | |
| 2010/0099684 A1 | 4/2010 | Cook, II et al. | |
| 2010/0105661 A1 | 4/2010 | Shirakami et al. | |
| 2010/0143547 A1 | 6/2010 | Kriegel et al. | |
| 2010/0204235 A1 | 8/2010 | Lizos | |
| 2010/0210636 A1 | 8/2010 | Ishikawa et al. | |
| 2010/0216798 A1 | 8/2010 | Nakai et al. | |
| 2010/0239496 A1 | 9/2010 | Gangadharmath et al. | |
| 2011/0045511 A1 | 2/2011 | Graus Porta et al. | |
| 2011/0159604 A1 | 6/2011 | Fan et al. | |
| 2011/0160203 A1 | 6/2011 | Liu et al. | |
| 2011/0195968 A1 | 8/2011 | Greul et al. | |
| 2011/0212077 A1 | 9/2011 | Noronha et al. | |
| 2011/0224155 A1 | 9/2011 | Tachdjian et al. | |
| 2011/0262525 A1 | 10/2011 | Wang et al. | |
| 2011/0313003 A1 | 12/2011 | Shi et al. | |
| 2012/0035153 A1 | 2/2012 | Saxty et al. | |
| 2012/0135997 A1 | 5/2012 | Kato et al. | |
| 2012/0165305 A1 | 6/2012 | Yao et al. | |
| 2012/0295881 A1 | 11/2012 | Lange et al. | |
| 2012/0319095 A1 | 12/2012 | Tada et al. | |
| 2013/0078731 A1 | 3/2013 | George et al. | |
| 2013/0200356 A1 | 8/2013 | Jung et al. | |
| 2013/0210825 A1 | 8/2013 | Rehwinkel et al. | |
| 2013/0338134 A1 | 12/2013 | Wu et al. | |
| 2014/0045814 A1 | 2/2014 | Lu et al. | |
| 2014/0054564 A1 | 2/2014 | Kim et al. | |
| 2014/0080892 A1 | 3/2014 | Bhanot et al. | |
| 2014/0088100 A1 | 3/2014 | Bifulco, Jr. et al. | |
| 2014/0103325 A1 | 4/2014 | Shin et al. | |
| 2014/0117318 A1 | 5/2014 | Choi et al. | |
| 2014/0148548 A1 | 5/2014 | Yamanaka et al. | |
| 2014/0171405 A1 | 6/2014 | Zhuo et al. | |
| 2014/0187559 A1 | 7/2014 | Miduturu | |
| 2014/0194430 A1 | 7/2014 | Eis et al. | |
| 2014/0228370 A1 | 8/2014 | Eis et al. | |
| 2014/0243308 A1 | 8/2014 | Yao et al. | |
| 2014/0288069 A1 | 9/2014 | Eis et al. | |
| 2014/0296233 A1 | 10/2014 | D'Agostino et al. | |
| 2014/0315902 A1 | 10/2014 | Sun et al. | |
| 2014/0374722 A1 | 12/2014 | Kim et al. | |
| 2014/0378468 A1 | 12/2014 | Aichholz et al. | |
| 2014/0378481 A1 | 12/2014 | Bifulco, Jr. et al. | |
| 2014/0378483 A1 | 12/2014 | Benazet et al. | |
| 2015/0011548 A1 | 1/2015 | Linnanen et al. | |
| 2015/0011560 A1 | 1/2015 | Legeai-Mallet | |
| 2015/0011579 A1 | 1/2015 | Clary-Ceccato et al. | |
| 2015/0038485 A1 | 2/2015 | Eis et al. | |
| 2015/0197519 A1 | 7/2015 | Bifulco | |
| 2016/0115164 A1 | 4/2016 | Wu et al. | |
| 2016/0244448 A1 | 8/2016 | Lu et al. | |
| 2016/0244449 A1 | 8/2016 | Lu et al. | |
| 2016/0244450 A1 | 8/2016 | Lu et al. | |
| 2016/0280713 A1 | 9/2016 | Lu et al. | |
| 2017/0107216 A1 | 4/2017 | Wu et al. | |
| 2017/0119782 A1 | 5/2017 | Lu et al. | |
| 2017/0137424 A1 | 5/2017 | Wu et al. | |
| 2017/0145025 A1 | 5/2017 | Li et al. | |
| 2017/0165263 A1 | 6/2017 | Yao et al. | |
| 2017/0166564 A1 | 6/2017 | Sun et al. | |
| 2017/0174671 A1 | 6/2017 | Wu et al. | |
| 2017/0174679 A1 | 6/2017 | Lajkiewicz et al. | |
| 2017/0260168 A1 | 9/2017 | Andrews et al. | |
| 2017/0290839 A1 | 10/2017 | Lu et al. | |
| 2017/0320875 A1 | 11/2017 | Li et al. | |
| 2017/0320877 A1 | 11/2017 | Wu et al. | |
| 2017/0342060 A1 | 11/2017 | Lu et al. | |
| 2017/0362253 A1 | 12/2017 | Xiao et al. | |
| 2018/0008610 A1 | 1/2018 | Lu et al. | |
| 2018/0016260 A1 | 1/2018 | Yu et al. | |
| 2018/0057486 A1 | 3/2018 | Wu et al. | |
| 2018/0072718 A1 | 3/2018 | Liu et al. | |
| 2018/0177784 A1 | 6/2018 | Wu et al. | |
| 2018/0177870 A1 | 6/2018 | Liu et al. | |

(56) References Cited

U.S. PATENT DOCUMENTS

| | | | |
|---|---|---|---|
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0244672 A1 | 8/2018 | Lu et al. |
| 2018/0273519 A1 | 9/2018 | Wu et al. |
| 2019/0040082 A1 | 2/2019 | Xiao et al. |
| 2019/0055237 A1 | 2/2019 | Pan et al. |
| 2019/0062327 A1 | 2/2019 | Sun et al. |
| 2019/0062345 A1 | 2/2019 | Xiao et al. |
| 2019/0071439 A1 | 3/2019 | Li et al. |
| 2019/0092767 A1 | 3/2019 | Li et al. |
| 2019/0127376 A1 | 5/2019 | Wu et al. |
| 2019/0127467 A1 | 5/2019 | Shah et al. |
| 2019/0144439 A1 | 5/2019 | Wu et al. |
| 2019/0152973 A1* | 5/2019 | Lee ................. A61P 35/00 |
| 2019/0202824 A1 | 7/2019 | Wu et al. |
| 2019/0225601 A1 | 7/2019 | Wu et al. |
| 2019/0240220 A1 | 8/2019 | Yao et al. |
| 2019/0241560 A1 | 8/2019 | Lu et al. |
| 2019/0269693 A1 | 9/2019 | Lu et al. |
| 2019/0284187 A1 | 9/2019 | Wu et al. |
| 2019/0300524 A1 | 10/2019 | Wu et al. |
| 2019/0337948 A1 | 11/2019 | Frietze et al. |
| 2019/0345170 A1 | 11/2019 | Wu et al. |
| 2020/0002338 A1 | 1/2020 | Jia et al. |
| 2020/0055853 A1 | 2/2020 | Ellies et al. |
| 2020/0095244 A1 | 3/2020 | Sun et al. |
| 2020/0255424 A1 | 8/2020 | Wu et al. |
| 2020/0270245 A1 | 8/2020 | Pan et al. |
| 2020/0277309 A1 | 9/2020 | Wu et al. |
| 2020/0306256 A1 | 10/2020 | Lu et al. |
| 2020/0377504 A1 | 12/2020 | Wu et al. |
| 2020/0399267 A1 | 12/2020 | Lu et al. |
| 2021/0009582 A1 | 1/2021 | Vechorkin et al. |
| 2021/0094935 A1 | 4/2021 | Vechorkin |
| 2021/0106588 A1 | 4/2021 | Vechorkin et al. |
| 2021/0115053 A1 | 4/2021 | Shvartsbart et al. |
| 2021/0171522 A1 | 6/2021 | Tao et al. |
| 2021/0171535 A1* | 6/2021 | McCammant ....... C07D 487/14 |
| 2021/0214366 A1 | 7/2021 | Roach et al. |
| 2021/0380587 A1 | 12/2021 | Wu et al. |
| 2021/0395246 A1 | 12/2021 | Sun et al. |
| 2022/0009921 A1 | 1/2022 | Lu et al. |
| 2022/0153740 A1 | 5/2022 | Jia et al. |
| 2023/0002385 A1* | 1/2023 | Li ..................... A61K 31/4375 |
| 2023/0192722 A1 | 6/2023 | Liu et al. |
| 2023/0338389 A1 | 10/2023 | Vechorkin et al. |
| 2024/0287086 A1 | 8/2024 | McCammant et al. |

FOREIGN PATENT DOCUMENTS

| | | |
|---|---|---|
| CL | 2017000654 | 12/2017 |
| CL | 2017001984 | 3/2018 |
| CL | 2018000089 | 5/2018 |
| CL | 2018000124 | 5/2018 |
| CL | 2017002117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 101679408 | 3/2010 |
| CN | 101715451 | 5/2010 |
| CN | 102399220 | 4/2012 |
| CN | 102399233 | 4/2012 |
| CN | 102666536 | 9/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| EP | 3184521 | 6/2017 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 2006028027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2007-522098 | 8/2007 |
| JP | 2008198769 | 8/2008 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 2011009348 | 1/2011 |
| JP | 2011044637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 2013049251 | 3/2013 |
| JP | 2013179181 | 9/2013 |
| JP | 2015517376 | 6/2015 |
| JP | 2018507214 | 3/2018 |
| JP | 2018511573 | 4/2018 |
| JP | 6336665 | 6/2018 |
| KR | 20010043829 | 5/2001 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| WO | WO 1988/03025 | 5/1988 |
| WO | WO 1991/09835 | 7/1991 |
| WO | WO 1991/10172 | 7/1991 |

(56) References Cited

FOREIGN PATENT DOCUMENTS

| | | |
|---|---|---|
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/09495 | 2/2000 |
| WO | WO 2002/000196 | 2/2000 |
| WO | WO 2000/24744 | 5/2000 |
| WO | WO 2000/053595 | 9/2000 |
| WO | WO 2000/68186 | 11/2000 |
| WO | WO 2001/02369 | 1/2001 |
| WO | WO 2001/014402 | 3/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |
| WO | WO 2001/58899 | 8/2001 |
| WO | WO 2001/64655 | 9/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/083648 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/024967 | 3/2003 |
| WO | WO 2003/037347 | 5/2003 |
| WO | WO 2003/037891 | 5/2003 |
| WO | WO 2003/040131 | 5/2003 |
| WO | WO 2003/042402 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099771 | 12/2003 |
| WO | WO 2003/099818 | 12/2003 |
| WO | WO 2003/101985 | 12/2003 |
| WO | WO 2004/002986 | 1/2004 |
| WO | WO 2004/005281 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046120 | 6/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056786 | 7/2004 |
| WO | WO 2004/056822 | 7/2004 |
| WO | WO 2004/056830 | 7/2004 |
| WO | WO 2004/065378 | 8/2004 |
| WO | WO 2004/080980 | 9/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/028444 | 5/2005 |
| WO | WO 2005/040119 | 5/2005 |
| WO | WO 2005/046589 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/056399 | 6/2006 |
| WO | WO 2006/058120 | 6/2006 |
| WO | WO 2006/062465 | 6/2006 |

(56) References Cited

FOREIGN PATENT DOCUMENTS

| | | |
|---|---|---|
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/037459 | 4/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2008/156712 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/050183 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/085185 | 7/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/124755 | 10/2009 |
| WO | WO 2009/125808 | 10/2009 |

(56) References Cited

FOREIGN PATENT DOCUMENTS

| | | |
|---|---|---|
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/148916 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/009735 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/036959 | 4/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/062571 | 6/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/075074 | 7/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/089411 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/053518 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/066342 | 6/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082400 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101409 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |

(56) References Cited

FOREIGN PATENT DOCUMENTS

| | | |
|---|---|---|
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2011/159877 | 12/2011 |
| WO | WO 2011/161699 | 12/2011 |
| WO | WO 2011/163330 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061156 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/078777 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/084704 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/129344 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/053051 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/064960 | 4/2016 |
| WO | WO 2016/134314 | 8/2016 |
| WO | WO 2016/192680 | 12/2016 |
| WO | WO 2017/023972 | 2/2017 |
| WO | WO 2017/023988 | 2/2017 |
| WO | WO 2017/023989 | 2/2017 |
| WO | WO 2017/024003 | 2/2017 |
| WO | WO 2017/024004 | 2/2017 |
| WO | WO 2017/024015 | 2/2017 |
| WO | WO 2017/024025 | 2/2017 |
| WO | WO 2017/028314 | 2/2017 |
| WO | WO 2017/050864 | 3/2017 |
| WO | WO 2017/223414 | 12/2017 |
| WO | WO 2018/041091 | 3/2018 |
| WO | WO 2018/049214 | 3/2018 |
| WO | WO 2018/067512 | 4/2018 |
| WO | WO 2018/093029 | 5/2018 |
| WO | WO 2018/093215 | 5/2018 |
| WO | WO 2018/105972 | 6/2018 |
| WO | WO 2018/105973 | 6/2018 |
| WO | WO 2018/153373 | 8/2018 |
| WO | WO 2018/234354 | 12/2018 |
| WO | WO 2019/037640 | 2/2019 |

(56) References Cited

FOREIGN PATENT DOCUMENTS

| | | |
|---|---|---|
| WO | WO 2019/079369 | 4/2019 |
| WO | WO 2019/105886 | 6/2019 |
| WO | WO 2019/213506 | 11/2019 |
| WO | WO 2020/049017 | 3/2020 |
| WO | WO 2020/131627 | 6/2020 |
| WO | WO 2020/131674 | 6/2020 |
| WO | WO 2020/182062 | 9/2020 |
| WO | WO 2021/113479 | 6/2021 |

OTHER PUBLICATIONS

Charoenngam, N., "Hereditary metabolic bone diseases: A review of pathogenesis, diagnosis and management." Genes 13.10 (2022): 1-34.
Liang, G., "Small molecule inhibition of fibroblast growth factor receptors in cancer." Cytokine & growth factor reviews 24.5 (2013): 467-475.
Office Action in Eurasian Appln. No. 202291162, dated May 19, 2023, 7 pages (with English translation).
"Sabiosciences.com" [online]. "FGF Pathway," 2000-2012, [retrieved on Jun. 23, 2015]. Retrieved from the Internet: URL <http://www.sabiosciences.com/pathway.php?sn-FGF_Signaling>, 3 pages.
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Adib et al., "FGFR2/3 genomic alterations and response to Enfortumab Vedotin in metastatic urothelial carcinoma," BJUI Compass., 2022, 3:169-172.
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.
Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.
Anonymous, "American Society for Clinical Pharmacology and Therapeutics," Clin Pharma and Thera., Feb. 13, 2019, 105(S1):S5-S121.
Anonymous, "In Vitro Metabolism- and Transporter-Mediated Drug-Drug Interaction Studies Guidance for Industry", Clinical Pharmacology, Oct. 2017, 47 pages.
Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.
Arai et al., "Characterization of the cell or origin and propagation potential of the fibroblast growth factor 9-induced mouse model of lung adenocarcinoma," J. Pathol., Mar. 2015, 235(4): 593-605.
Arai et al., "Fibroblast growth factor receptor 2 tyrosine kinase fusions define a unique molecular subtype of cholangiocarcinoma," Hepatology, 2014, 59(4):1427-1434.
Argentina Office Action in Argentina Application No. 20130102068, dated Jul. 17, 2020, 10 pages.
Argentina Office Action in Argentina Application No. 20140101651, dated Jul. 29, 2021, 9 pages.
Argentina Office Action in Argentina Application No. 20180101392, dated Mar. 8, 2022, 6 pages.
Argentina Office Action in Argentina Application No. 20140101651, dated Nov. 21, 2019, 5 pages.
Ash and Ash, "Handbook of Pharmaceutical Additives," Gower Publishing Company, 2007, 3rd ed, *********too voluminous to provide*******.
Atzrodt et al., "The Renaissance of H/D Exchange," Angew Chem Int Ed., 2007, 7744-7765.
Australian Allowance in Australian Application No. 2020250201, dated Jun. 23, 2022, 4 pages.
Australian Office Action in Australian Application No. 2013287176, dated Sep. 12, 2017, 4 pages.
Australian Office Action in Australian Application No. 2014253798, dated Jul. 31, 2017, 4 pages.
Australian Office Action in Australian Application No. 2016219816, dated Aug. 26, 2019, 3 pages.
Australian Office Action in Australian Application No. 2016219822, dated Jul. 8, 2019, 4 pages.
Australian Office Action in Australian Application No. 2018208772, dated Jul. 1, 2018, 5 pages.
Australian Office Action in Australian Application No. 2018272013, dated Sep. 2, 2021, 4 pages.
Australian Office Action in Australian Application No. 2019200066, dated Aug. 27, 2019, 6 pages.
Australian Office Action in Australian Application No. 2020250211, dated Sep. 13, 2021, 4 pages.
Australian Office Action in Australian Application No. 2020270520, dated Dec. 16, 2021, 4 pages.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Balek, L., "ARQ 087 inhibits FGFR signaling and rescues aberrant cell proliferation and differentiation in experimental models of craniosynostoses and chondrodysplasias caused by activating mutations in FGFR1, FGFR2 and FGFR3," Bone, Dec. 2017, 105:57-66.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Bauer, "Pharmaceutical Solids—The Amorphous Phase", Journal of Validation Technology, 2009, 15(3):63-68.
Bavin, "Polymorphism in Process Development," Chemistry & Industry, Society of Chemical Industry, Aug. 1989, 527-529.
Bazyl et al., "The selective ortho-methoxylation of pentafluorobenzoic acid—a new way to tetrafluorosalicylic acid and its derivatives," J Flour Chem., Feb. 11, 1999, 94(1):11-13.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 1977, 66(2):1-19.
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R )-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.

(56) References Cited

OTHER PUBLICATIONS

Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J Combi Chem., 2003, 5:670.
Blom et al., Preparative LC-MS Purification: Improved Compound Specific Method Optimization, J Combi Chem. 2004, 6(6):874-883.
Blom, K., "Two-Pump At Column Dilution Configuration for Preparative LC-MS", J Combi Chem., 2002, 4:295.
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Borad et al., "Fibroblast growth factor receptor 2 fusions as a target for treating cholangiocarcinoma," Current opinion in Gastroenterology, May 2015, 31(3):264-268.
Brazilian Office Action in Brazilian Application No. BR112019024769-6, dated Aug. 29, 2022, 7 pages.
Brennfuhrer et al., "Palladium-Catalyzed Carbonylation Reactions of Aryl Halides and Related Compounds," Angew Chem Int Ed., May 25, 2009, 48(23):4114-4133.
Brooks et al., "Fibroblast growth factor signaling: a new therapeutic opportunity in cancer," Clinical Cancer Research, 2012, 1-23.
Byrn et al., "Pharmacautical Solids: A Strategic Approach to Regulatory Considerations," Pharmaceutical Research., Jul. 1995, 12(7):945-954.
Caira, "Crystalline Polymorphism of Organic Compounds," Topics in Current Chemistry, Jan. 1, 1998, 198:163-208.
Canada Office Action in Canada Application No. 2,976,788, dated Apr. 7, 2022, 4 pages.
Canada Office Action in Canada Application No. 2,976,790, dated Apr. 25, 2022, 4 pages.
Cancer [online], [retrieved on Jul. 6, 2007] Retrieved from the Internet, URL: http://www.nlm.nih.gov/medlineplus/cancer.html.
Capelletti et al., "Identification of Recurrent FGFR3-TACC3 Fusion Oncogenes from Lung Adenocarcinoma," AACR Journals, 2014, 6551-6558.
Cappellen et al., "Frequent activating mutations of FGFR3 in human bladder and cervix carcinomas," Nature Genetics, Sep. 1999, 23: 18-20.
Carmichael et al., "Familial Tumoral Calcinosis: A Forty-Year Follow-up on One Family," The Journal of Bone & Joint Surgery, 2009, 664-671.
Casey et al., "Translating in vivo metabolomic analysis of succinate dehydrogenase deficient tumours into clinical utility," JCO Precis Oncol., Mar. 29, 2018, 2:1-12.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chandrani et al., "Drug-sensitive FGFR3 mutations in lung adenocarcinoma," Annals of Oncology, 2017, 28: 597-603.
Chase et al., "Activity of TKI258 against primary cells and cell lines with FGFR1 fusion genes associated with the 8p11 myeloproliferative syndryome," Blood, 2007, 110:3729-3734.

Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chen et al., "Genome-Wide Loss of Heterozygosity and DNA Copy Number Aberration in HPV-Negative Oral Squamous Cell Carcinoma and Their Associations with Disease-Specific Survival," PLOS One, Aug. 2015, 23 pages.
Cherukupalli et al., "An insight on synthetic and medicinal aspects of pyrazolo[1,5-a]pyrimidine scaffold," European Journal of Medicinal Chemistry, Nov. 10, 2016, 126:298-352.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chilean Office Action in Chilean Application No. 1984-2017, dated Sep. 12, 2019, 9 pages.
Chilean Office Action in Chilean Application No. 2015-003089, dated Apr. 24, 2017, 13 pages (English Summary).
Chilean Office Action in Chilean Application No. 2015-003089, dated Jan. 23, 2018, 8 pages.
Chilean Office Action in Chilean Application No. 2122-2017, dated Apr. 22, 2019, 25 pages.
Chilean Office Action in Chilean Application No. 2122-2017, dated Nov. 15, 2019, 15 pages.
Chilean Office Action in Chilean Application No. 2839-2020, dated Jan. 31, 2022, 42 pages (with English translation).
Chilean Office Action in Chilean Application No. 2848-2020, dated Mar. 7, 2022, 23 pages.
Chilean Office Action in Chilean Application No. 3355-2014, dated Jan. 18, 2017, 17 pages (with English translation).
Chilean Office Action in Chilean Application No. 3439-2019, dated Feb. 10, 2021, 26 pages.
Chilean Office Action in Chilean Application No. 3439-2019, dated Jan. 31, 2022, 15 pages.
Chilean Opposition in Chilean Application No. 3355-2014, received Feb. 3, 2017, 3 pages (English translation only).
Chinese Office Action in Chinese Application No. 10874686.0, dated Oct. 8, 2019, 10 pages.
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Apr. 4, 2018, 10 pages (English Translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chinese Office Action in Chinese Application No. 201680011332.7, dated Aug. 5, 2019, 14 pages.
Chinese Office Action in Chinese Application No. 201680011348.8, dated Aug. 2, 2019, 14 pages.
Chinese Office Action in Chinese Application No. 201710395346.X, dated Jan. 22, 2019, 17 pages.

(56) References Cited

OTHER PUBLICATIONS

Chinese Office Action in Chinese Application No. 201710395346. X, dated Sep. 9, 2019, 10 pages.
Chinese Office Action in Chinese Application No. 201710874686.0, dated Feb. 25, 2019, 17 pages.
Chinese Office Action in Chinese Application No. 201910023729.3, dated Mar. 23, 2022, 11 pages.
Chinese Office Action in Chinese Application No. 201910023729.3, dated Sep. 8, 2021, 11 pages.
Chinese Office Action in Chinese Application No. 201910023729.3, dated Mar. 3, 2021, 15 pages.
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Ciappetti and Geithlen "Molecular Variations Based on Isosteric Replacements," The Practice of Medicinal Chemistry, 2008, Chapter 15, pp. 290-341.
ClinicalTrials.gov, "A Study to Evaluate the Efficacy and Safety of Pemigatinib Versus Cherrotherapy in Unresectable or Metastatic ChoI (FIGHT-302)," NCT03656536, Mar. 6, 2019, retrieved from URL <https://www.clinicaltrials.gov/ct2/history/NCT03656536?V_5=View#StudyPageTop,>, 4 pages.
Cole et al., "Inhibition of FGFR2 and FGFR1 increases cisplatin sensitivity in ovarian cancer," Cancer Biol. Therapy, Sep. 1, 2010, 10(5):495-504.
Coleman, "Positive and negative regulation of cellular sensitivity to anti-cancer drugs by FGF-2," Drug Resistance Updates, 2003, 85-94.
Colombian Office Action in Colombian Application No. 14-275934-6, dated May 31, 2016, 3 pages (English translation only).
Colombian Office Action in Colombian Application No. 14-275934-6, dated Nov. 17, 2015, 12 pages (English translation only).
Colombian Office Action in Colombian Application No. 16100866, dated Aug. 10, 2017, 9 pages.
Colombian Office Action in Colombian Application No. NC2017/0008795, dated Nov. 29, 2018, 8 pages.
Colombian Office Action in Colombian Application No. NC2017/0008795, dated Aug. 16, 2019, 6 pages.
Colombian Office Action in Colombian Application No. NC2017/0008795, dated Aug. 29, 2017, 2 pages.
Colombian Office Action in Colombian Application No. NC2017/0008824, dated Aug. 31, 2017, 3 pages.
Colombian Office Action in Colombian Application No. NC2017/0008824, dated Nov. 29, 2018, 8 pages.
Colombian Office Action in Colombian Application No. NC2019/0009690, dated Jan. 22, 2020, 20 pages.
Colombian Office Action in Colombian Application No. NC2019/0014699, dated Jun. 6, 2022, 31 pages.
Colombian Opposition in Colombian Application No. NC 2021/0004568, dated Apr. 15, 2021, 21 pages.
Cordovilla et al., "The Stille Reaction, 38 Years Later," ACS Catal., Apr. 17, 2015, 5(5):3040-3053.
Corre et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Costa Rican Office Action in Costa Rican Application No. 2014-0577, dated Apr. 15, 2020, 18 pages.
Costa Rican Office Action in Costa Rican Application No. 2014-0577, dated Jun. 13, 2019, 17 pages.
Costa Rican Office Action in Costa Rican Application No. 2015-0578, dated Jun. 11, 2020, 15 pages.
Costa Rican Office Action in Costa Rican Application No. 2019-573, dated Jul. 12, 2022, 12 pages.
Costa Rican Opposition in Costa Rican Application No. PCT/US2013/045309, dated Jun. 29, 2015, 14 pages (English Translation).
Covic et al., "Vascular calcification in chronic kidney disease," Clinical Science, 2010, 119: 111-121.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Desnoyers et al., "Targeting FGF19 inhibits tumor growth in colon cancer xenograft and FGF19 transgenic hepatocellular carcinoma models," Oncogene, 2008, 27:85-97.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Ding et al., "Somatic mutations affect key pathways in lung adenocarcinoma," Nature., Oct. 23, 2008, 455:1069-1075.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Drueke et al., "Phosphate binders in CKD: bad news or good news?," Journal of the American Society of Nephrology, Aug. 2012, 23(8):1277-1280.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Ecuador Office Action in Ecuador Application No. IEPI-2015-1225, dated Dec. 30, 2021, 21 pages.
Ecuador Office Action in Ecuador Application No. IEPI-2015-1225, dated May 11, 2022, 18 pages.
Ecuador Opposition in Ecuador Application No. SENADI-2020-78226, dated Jun. 2022, 19 pages.
Ecuador Opposition in Ecuador Application No. SENADI-2020-78230, dated Jun. 2022, 21 pages.
Edmondson et al., "Aminopiperidine-fused imidazoles as dipeptidyl peptidase-IV inhibitors," Bioorg & Med Chem Lett., 2009, 19(15):4097-4101.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10):1049-1056.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.

(56) References Cited

OTHER PUBLICATIONS

Eurasian Office Action in Eurasian Application No. 201590005, Mar. 28, 2018, 6 pages.
Eurasian Office Action in Eurasian Application No. 201791866, dated Feb. 19, 2018, 10 pages (English Translation).
Eurasian Office Action in Eurasian Application No. 201791867, dated Apr. 4, 2018, 4 pages (English Translation).
Eurasian Office Action in Eurasian Application No. 201992794, dated Sep. 17, 2021, 7 pages.
Eurasian Office Action in Eurasian Application No. 202091923, dated Apr. 5, 2022, 4 pages.
Eurasian Office Action in Eurasian Application No. 202091923, dated Jul. 27, 2021, 6 pages (English Translation).
Eurasian Office Action in Eurasian Application No. 202092648, dated Feb. 8, 2022, 7 pages.
Eurasian Office Action in Eurasian Application No. 202092649/26, dated Apr. 22, 2022, 6 pages.
Eurasian Office Action in Eurasian Application No. 202190877, dated Oct. 6, 2021, 4 pages.
European Communication pursuant to Article 94(3) EPC in European Application No. 13783125.1, dated Jan. 26, 2016, 4 pages.
European Office Action in European Application No. 16715139.8, dated May 18, 2021, 9 pages.
European Office Action in European Application No. 18733045.1, dated Jan. 11, 2021, 5 pages.
European Office Action in European Application No. 19724670, dated Aug. 31, 2022, 3 pages.
European Office Action in European Application No. 19724670.5, dated Nov. 9, 2021, 4 pages.
European Office Action in European Application No. 19724676.2, dated Aug. 26, 2021, 5 pages.
European Office Action in European Application No. 20192679.7, dated Feb. 11, 2021, 7 pages.
European Office Action in European Application No. 20834013.3, dated Jul. 12, 2022, 3 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Ezzat et al., "Dual Inhibition of RET and FGFR4 Restrains Medullary Thyroid Cancer Cell Growth," Clinical Cancer Research, 2005, 11:1336-1341.
Faul et al., "FGF23 induces left ventricular hypertrophy," The Journal of Clinical Investigation, 2010, 1-16.
FDA.gov, "FDA grants accelerated approval to pemigatinib for cholangiocarcinoma with an FGFR2 rearrangement or fusion," Apr. 20, 2020, [Retrieved on Apr. 27, 2021], retrieved from URL <https://www.fda.gov/drugs/resources-information-approved-drugs/fda-grants-accelerated-approval-pemigatinib-cholangiocarcinoma-fgfr2-rearrangement-or-fusion>, 2 pages.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cell lung cancer cells: therapeutic implications and synergism with epidermal growth factor receptor inhibition," Mol Cancer Therapy, 2008, 3408-3419.
French et al., Targeting FGFR4 inhibits hepatocellular carcinoma in preclinical mouse models, PLoS One 2012;7:e36713.

Fricker, "Metal based drugs: from serendipity to design," Dalton Transactions, 2007, 43:4903-4917.
Fricker, "The therapeutic application of lanthanides," Chemical Society Reviews, 2006, 35(6):524-533.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fu et al., "Intratumoral inorganic phosphate deprivation: A new anticancer strategy," Medical Hypotheses, Feb. 2020, 135:109497.
Fukumoto and Yamashita, "FGF23 is a hormone-regulating phophate metabolism—Unique biological characteristics of FGF23," Bone, 2007, 1190-1195.
Fun et al., "2-7(7,8-Diphenyl-1H-imidazo[4,5-f]-quinoxalin-2-yl)phenol methanol disolvate," Acta Crystallographica Section E Structure Reports Online, 2008, 64(9):o1741-o1742.
Furniss "Acidic/Basic characteristics for purification," Vogel's Textbook of Practical Organic Chemistry, 5th edition, 1989, 131-133, 135-143.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Gallo et al., "Functions of Fibroblast Growth Factor Receptors in cancer defined by novel translocations and mutations," Cytokine & Growth Factor Reviews, 2015, 26(4):425-449.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gennaro et al., "Pharmaceutical Sciences," Remington's Pharmaceutical Sciences 17th Ed., Jan. 1985, 14-18 and 1409-1423.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno[b] Thieno(Pyridines, Quinolines, Oxazines and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed, 559 pages.
Goetz et al., "Isolated C-terminal tail of FGF23 alleviates hypophosphatemia by inhibiting FGF23-FGFR-Klotho complex formation," PNAS, Jan. 2010, 107(1):407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11):1045-1089.
Goyal et al,. "Polyclonal Secondary FGFR2 Mutations Drive Acquired Resistance to FGFR Inhibition in Patients with FGFR2 Fusion-Positive Cholangiocarcinoma," Cancer Discov., 2016, 7(3):252-263.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.

(56) References Cited

OTHER PUBLICATIONS

Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999), 799 pages.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxy-phenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Haas et al., "Recent Developments in Negishi Cross-Coupling Reactions," ACS Catal., 2016, 6(3):1540-1552.
Hackam et al. "Translation of Research Evidence From Animals to Humans," JAMA, 296(14), 2006, 296(14):1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.
Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3):1160-1170.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 22:259-267.
Hess et al., "Synergistic effect of combination of pemigatinib with enfortumab vedotin (EV) in human bladder cancer models," Molecular Cancer Therapeutics, Presented at AACR-NCI-EORT Virtual International Conference on Molecular Targets and Cancer Therapeutics, presented Oct. 7-10, 2021, 9 pages.
Hideshima and Anderson, "Preclinical Studies of Novel Targeted Therapies," Hematol Oncol Clin N Am, 2007, 1071-1091.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
ICH Harmonised Tripartite Guideline, "Specifications:Test Procedures and Acceptance Criteria for New Drug Substances and New Drug Products Chemical Substances," ICHTRRPHU, Oct. 6, 1999, 35 pages.
Ichikawa et al., "A homozygous missense mutation in human Klotho causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.
Indian Office Action in Indian Application No. 201717030265, dated Dec. 12, 2019, 5 pages.
Indian Office Action in Indian Application No. 201717030267, dated Dec. 3, 2019, 7 pages.
Indian Office Action in Indian Application No. 202017052609, dated May 23, 2022, 7 pages.
Indian Office Action in Indian Application No. 202017052853, dated May 13, 2022, 6 pages.
Indian Office Action in Indian Application No. 9781/DELNP/2015, dated Jan. 18, 2019, 6 pages.
Indian Oral Hearing in Indian Application No. 201717030265, dated Jan. 13, 2022, 2 pages.
Indian Oral Hearing in Indian Application No. 9781/DELNP/2015, dated Sep. 14, 2022, 3 pages.
Indonesian Office Action in Indonesian Application No. P00201507153, dated Apr. 27, 2018, 5 pages (English Translation).
Indonesian Office Action in Indonesian Application No. PID201705977, Jun. 5, 2020, 5 pages.
Inokuchi et al., "Therapeutic targeting of fibroblast growth factor receptors in gastric cancer," Gastroenterol Res Pract., Apr. 27, 2015, 2015:796380, 8 pages.
International Invitation to Pay Fees in International Appln. No. PCT/US2019/030633, dated Aug. 12, 2019, 5 pages.
International Preliminary Report on Patentability and Written Opinion in International Application No. PCT/US2011/066473, issued Jun. 25, 2013, 10 pages.
International Preliminary Report on Patentability in International Application No. PCT/US2013/045309, mailed Dec. 24, 2014, 11 pages.

(56) References Cited

OTHER PUBLICATIONS

International Preliminary Report on Patentability in International Application No. PCT/US2013/054361, mailed Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Preliminary Report on Patentability in International Application No. PCT/US2018/034559, dated Nov. 26, 2019, 8 pages.
International Preliminary Report on Patentability in International Application No. PCT/US2019/030578, dated Nov. 10, 2020, 14 pages.
International Preliminary Report on Patentability in International Application No. PCT/US2019/030633, dated Nov. 10, 2020, 10 pages.
International Preliminary Report on Patentability in International Application No. PCT/US2020/021313, dated Aug. 25, 2021, 11 pages.
International Preliminary Report on Patentability in International Application No. PCT/US2020/041104, dated Jan. 11, 2022, 7 pages.
International Preliminary Report on Patentability in International Application No. PCT/US2020/053436, dated Apr. 5, 2022, 8 pages.
International Preliminary Report on Patentability in International Application No. PCT/US2020/055547, dated Apr. 19, 2022, 7 pages.
International Preliminary Report on Patentability in International Application No. PCT/US2020/055735, dated Apr. 19, 2022, 8 pages.
International Preliminary Report on Patentability in International Application No. PCT/US2020/063038, dated Jun. 16, 2022, 8 pages.
International Preliminary Report on Patentability in International Application No. PCT/US2020/063064, dated May 17, 2022, 7 pages.
International Preliminary Report on Patentability in International Application No. PCT/US2021/013438, dated Jul. 28, 2022, 7 pages.
International Search Report and Written Opinion for International Application No. PCT/US2015/056583, dated Dec. 15, 2015, 10 pages.
International Search Report and Written Opinion in International Application No. PCT/US2020/053436, dated Dec. 4, 2020, 15 pages.
International Search Report and Written Opinion in International Application No. PCT/US2013/045309, mailed on Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, mailed Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report and Written Opinion in International Application No. PCT/US2018/034559, dated Mar. 8, 2019, 14 pages.
International Search Report and Written Opinion in International Application No. PCT/US2019/030578, dated Jul. 11, 2019, 26 pages.
International Search Report and Written Opinion in International Application No. PCT/US2019/030633, dated Nov. 28, 2019, 21 pages.
International Search Report and Written Opinion in International Application No. PCT/US2020/021313, dated Jun. 26, 2020, 19 pages.
International Search Report and Written Opinion in International Application No. PCT/US2020/041104, dated Sep. 4, 2020, 14 pages.
International Search Report and Written Opinion in International Application No. PCT/US2020/055547, dated Jan. 11, 2021, 13 pages.
International Search Report and Written Opinion in International Application No. PCT/US2020/055735, dated Dec. 15, 2020, 16 pages.
International Search Report and Written Opinion in International Application No. PCT/US2021/013438, dated Apr. 20, 2021, 16 pages.
International Search Report and Written Opinion in International Application No. PCT/US2022/032603, dated Aug. 26, 2022, 14 pages.
International Search Report and Written Opinion in International Application No. PCT/US2022/032604, dated Sep. 6, 2022, 15 pages.
International Search Report and Written Opinion in International Application. No. PCT/US2011/066473, dated Jun. 19, 2012, 15 pages.
International Search Report and Written Opinion in International Appln. No. PCT/US2020/063038, dated Mar. 15, 2021, 16 pages.
International Search Report and Written Opinion in International Appln. No. PCT/US2020/063064, dated Feb. 12, 2021, 13 pages.
Invitation to Pay Additional Fees and, Where Applicable, Protest Fee in International Application No. PCT/US2013/045309, mailed Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Israeli Office Action in Israeli Application No. 289834 dated Jul. 14, 2022, 4 pages.
Jackson et al., "8p11 Myeloproliferative syndrome: a review," Human Pathology, Apr. 1, 2010, 41:461-476.
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Japanese Office Action in Japanese Application No. 2016-509131, dated Feb. 20, 2018, 5 pages (English Translation).
Japanese Office Action in Japanese Application No. 2017-543981, dated Dec. 3, 2019, 4 pages.
Japanese Office Action in Japanese Application No. 2017-544021, dated Nov. 26, 2019, 6 pages.
Japanese Office Action in Japanese Application No. 2018-228352, dated Aug. 20, 2019, 6 pages.
Japanese Office Action in Japanese Application No. 2019-565177, dated May 13, 2022, 11 pages.
Japanese Office Action in Japanese Application No. 2020-069604, dated Nov. 15, 2021, 7 pages.

(56) References Cited

OTHER PUBLICATIONS

Japanese Office Action in Japanese Application No. 2020-093529, dated Mar. 1, 2022, 5 pages.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jebar et al., "FGFR3 and Ras gene mutations are mutually exclusive genetic events in urothelial cell carcinoma," Oncogene, 2005, 24: 5218-5225.
Ji et al., "Embase abstract: Modeling and simulation as gating for clinical pharmacology studies of INCB054828," 119th Annual Meeting of the American Society for Clinical Pharmacology and Therapeutics, Mar. 1, 2018, 2 pages.
Jiang et al., "miR-99a promotes proliferation targeting FGFR3 in human epithelial ovarian cancer cells," Biomedicine & Pharmacotherapy, 2014, 68: 163-169.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, "Tamoxifen: A Most Unlikely Pioneering Medicine," Nature Reviews: Drug Discovery, Mar. 2003, 2:205-213.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Khojasteh et al., "Chemical inhibitors of cytochrome P450 isoforms in human liver microsomes: a re-evaluation of P450 isoform selectivity," Eur J Drug Metab Pharmacokinet., Mar. 2011, 36:1-16.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFRI Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS One, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Korean Office Action in Korean Application No. 10-2015-7000701, dated Aug. 26, 2019, 19 pages.
Korean Office Action in Korean Application No. 10-2015-7032502, dated Sep. 9, 2020, 16 pages.
Korean Office Action in Korean Application No. 10-2020-7021884, dated Oct. 25, 2021, 6 pages.
Korean Office Action in Korean Application No. 10-2020-7021884, dated Oct. 28, 2020, 15 pages.
Korean Office Action in Korean Application No. 10-2021-7018897, dated Oct. 1, 2021, 15 pages.
Korean Office Action in Korean Application No. 10-2022-7018808, dated Sep. 16, 2022, 5 pages.
Kotha et al., "Recent applications of the Suzuki-Miyaura cross-coupling reaction in organic synthesis," Tetrahedron, 2002, 58:9633-9695.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.

(56) References Cited

OTHER PUBLICATIONS

Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," Blood, Mar. 2005, 105(5): 2115-2123.
Malaysian Office Action in Malaysian Application No. 2014003396, dated Dec. 15, 2017, 4 pages.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marks et al., "Mutational Analysis of EGFR and Related Signaling Pathway Genes in Lung Adenocarcinomas Identifies a Novel Somatic Kinase Domain Mutation in FGFR4," PLoS One, May 9, 2007, 2:e426.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Martino et al., "Mutant fibroblast growth factor receptor 3 induces intracellular signaling and cellular transformation in a cell type- and mutation-specific manner," Oncogene, 2009, 28: 4306-4316.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Mexican Office Action in Mexican Application No. MX/a/2014/015192, dated Jan. 24, 2018, 6 pages.
Mexican Office Action in Mexican Application No. MX/a/2019/014097, dated Aug. 9, 2022, 13 pages.
Mexican Office Action in Mexican Application No. MX/a/2019/014097, dated Mar. 15, 2022, 12 pages.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)-mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
Neidle et al., "Failure Modes in the Discovery Process," Cancer Drug Design, 2008, pp. 427-431.
New Zealand Examination Report in New Zealand Application No. 743274, dated Jul. 18, 2018, 4 pages.
New Zealand Office Action in New Zealand Application No. 702747, dated Mar. 8, 2019, 2 pages.
New Zealand Office Action in New Zealand Application No. 702747, dated Sep. 16, 2016, 3 pages.
New Zealand Office Action in New Zealand Application No. 713074, dated Feb. 18, 2020, 3 pages.
New Zealand Office Action in New Zealand Application No. 743274, dated Jul. 19, 2018, 5 pages.
New Zealand Office Action in New Zealand Application No. 752422, dated Feb. 18, 2020, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Novelli, "Fosrenol (TM) reduces damaging high levels of phosphate in end-stage kidney disease patients," EurekAlert!, Nov. 2, 2002 [retrieved on Dec. 1, 2020], retrieved from URL <https://www.eurekalert.org/pub_releases/2002-11/pn-fr110202.php>, 4 pages.
Office Action from the Intellectual Property Office of the Philippines in Application No. 1-2014-502772, dated Mar. 17, 2016, 3 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.

(56) References Cited

OTHER PUBLICATIONS

Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Peruvian Office Action in Peruvian Application No. 1424, dated Mar. 12, 2021, 13 pages.
Peruvian Office Action in Peruvian Application No. 1429, dated Mar. 19, 2021, 12 pages.
Peruvian Office Action in Peruvian Application No. 2433, dated Nov. 27, 2018, 13 pages.
Peterson et al., Expanding the Scope of Crystal Form Evaluation in Pharmaceutical Science, J Pharm Pharmaceut Sci., 9(3): 317-326.
Philippine Allowance in Philippine Application No. 1/2015/502383, dated Jun. 6, 2022, 2 pages.
Philippine Office Action in Philippine Application No. 1/2015/502383, dated Nov. 11, 2021, 4 pages.
Philippine Office Action in Philippine Application No. 1/2017/501483, dated Dec. 12, 2019, 5 pages.
Philippine Office Action in Philippine Application No. 1/2019/502810, dated Dec. 7, 2021, 4 pages.
Philippine Office Action in Philippine Application No. 1-2017-501481, dated Oct. 29, 2019, 4 pages.
Philippine Office Action in Philippine Application No. 1/2015/502383, dated Jul. 8, 2019, 7 pages.
Philippine Office Action in the Philippine Application No. 1/2017/501483, dated Aug. 31, 2020, 4 pages.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Porta, "FGFR a promising druggable target in cancer: Molecular biology and new drugs." Critical reviews in oncology hematology, 2017, 113:256-267.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)-positive multiple myeloma in mice," The Journal of Clinical Investigation, May 2009, 119(5): 1216-1229.
Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington, "The Science and Practice of Pharmacy," Lippincott Williams & Wilkins, 2005, 21st edition *************Too voluminous to provide************.
Remington's Pharmaceutical Sciences, 17th ed., Mack Publishing Company, Easton, Pa., 1985, p. 1418*.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Rowe et al., "Handbook of Pharmaceutical Additives," The Pharmaceutical Press and the American Pharmaceutical Association, 2009, 3rd ed., *************Too voluminous to provide************.
Rowe et al., "Handbook of Pharmaceutical Excipients," The Pharmaceutical Press and the American Pharmaceutical Association, 2009, 6th Edition, 917 pages.
Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Comptetitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.

(56) References Cited

OTHER PUBLICATIONS

Science IP Order 3032627, Chemical Structure Search , Science IP, Apr. 2012, 78 pages.
Science IP Order 3101926, Chemical Structure Search , Science IP, Jan. 2015, 50 pages.
Science IP Order 3101983, Chemical Structure Search , Science IP, Jan. 2015, 70 pages.
Science IP Order 3104564, Patent Chemical Structure Search , Science IP, Mar. 2015, 90 pages.
Science IP Order 3104565, Patent Chemical Structure Search , Science IP, Mar. 2015, 521 pages.
Segev et al., "Restrained chondrocyte proliferation and maturation with abnormal growth plate vascularization and ossification in human FRFR-3$^{G380R}$ transgenic mice," Human Molecular Genetics, 2000, 9(2): 249-258.
Seitzer et al., "A single nucleotide change in the mouse genome accelerates breast cancer progression," Cancer Res., Jan. 2010, 70(2):802-812.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.
Shinya et al., "Fgf signalling through MAPK cascade is required for development of the subpallial telencephalon in zebrafish embryos," Development, 2001, 4153-4164.
sigmaaldrich.com, "4-Chloro-1H-pyrrolo[2,3-b]pyridine-5-carbaldehyde," CAS # 958230-19-8, [retrieved on Feb. 4, 2021] retrieved from URL <https://www.sigmaaldrich.com/catalog/product/aldrich/ade000976?lang-en®ion=US>, 2 pages.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-IIIc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
Staerk et al., "Pan-Src Family Kinase Inhibitors Replace Sox2 during the Direct Reprogramming of Somatic Cells," Angewandte Chem., Jun. 14, 2011, 50(25):5734-5736.
STN International Search Report for CAS RN 2380276-25-3, dated Nov. 20, 2019, 11 pages.
STN Search Report dated Jan. 6, 2020, 88 pages.
STN Search Report, dated Sep. 11, 2019, 31 pages.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-Rβ Tyrosine Kinases," J. Med. Chem., 2000, 43: 2655-2663.
Sun et al., "Synthesis and Biological Evaluations of 3-Substituted Indolin-2-ones: A Novel Class of Tyrosine Kinase Inhibitors That Exhibit Selectivity toward Particular Receptor Tyrosine Kinases," J. Med. Chem., 1998, 41: 2588-2603.
Surry et al., "Dialkylbiaryl Phosphines in Pd-Catalyzed Amination: A User's Guide," Chem Sci., 2011, 2(1):27-50.
Taiwan Office Action in Taiwan Application No. 103114284, dated Apr. 9, 2018, 4 pages (English Search Report).
Taiwan Office Action in Taiwan Application No. 105104993, dated Feb. 11, 2020, 9 pages.
Taiwan Office Action in Taiwan Application No. 105105018, dated Oct. 22, 2019, 7 pages.
Taiwan Office Action in Taiwan Application No. 107146498, dated Dec. 19, 2019, 7 pages.
Taiwan Office Action in Taiwan Application No. 109132389, dated Aug. 23, 2021, 4 pages.
Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Takii et al., "Serotonin Derivative, N-(p-Coumaroyl)serotonin, Isolated from Safflower (Carthamus tinctorius L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Tan et al., "Development of covalent inhibitors that can overcome resistance to first-generation FGFR kinase inhibitors," PNAS, Oct. 2014, E4869-E4877.
Tang et al., "Role of fibroblast growth factor receptor 4 in cancer," Cancer Science, Oct. 2018, 109(10):3024-3031.
Taylor et al., "Identification of FGFR4-activating mutations in human rhabdomyasarcomas that promote metastasis in xenotransplanted models," J Clin Invest., Nov. 2009, 119(11):3395-3407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
The Cancer Genome Atlas Research Network, "Comprehensive molecular characterization of urothelial bladder carcinoma," Nature, 2014, 507: 315-22.
Thome and Weil, "Post-translational modifications regulate distinct functions of CARMA1 and BCL10," Trends in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistry Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast

(56) References Cited

OTHER PUBLICATIONS

Growth Factor Receptor-1 and Vascular Endothelial Growth Factor Receptor-2 Tyrosine Kinases," J. Med. Chem., 2005, 48: 4628-2653.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Tolcher et al., "381 Preliminary results of a dose escalation study of the Fibroblast Growth Factor (FGF)"trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turkington et al., "Fibroblast growth factor receptor 4 (FGFR4): a targetable regulator of drug resistance in colorectal cancer," Cell Death Dis., Feb. 6, 2014, 5:e1046.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.
Ukraine Office Action in Ukraine Application No. a 2019 12195, dated Nov. 11, 2021, 7 pages.
Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).
Ukraine Office Action in Ukraine Application No. a201709220, dated Dec. 9, 2019, 11 pages.
Ukraine Office Action in Ukraine Application No. a201801562, dated Jul. 28, 2021, 9 pages.
Ukraine Office Action in Ukraine Application No. a202007700, dated Sep. 13, 2022, 11 pages.
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
Van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Verstovsek et al., "Interim Results from Fight-203, a Phase 2, Open-Label, Multicenter Study Evaluating the Efficacy and Safety of Pemigatinib (INCB054828) in Patients with Myeloid/Lymphoid Neoplasms with Rearrangement of Fibroblast Growth Factor Receptor 1 (FGFR1)," Blood, Nov. 29, 2018, retrieved from URL <https://ashpublications.org/blood/article/132/Supplement%201/690/266005/Interim-Results-from-Fight203-a-Phase-2-0penLabel>, 132(Supplement 1):690.
Vietnamese Office Action in Vietnamese Application No. 1-2015-00102, dated Mar. 18, 2015, 4 pages.
Vietnamese Office Action in Vietnamese Application No. 1-2022-03016, dated Jul. 8, 2022, 2 pages.
Vogt et al., "FGF23 and phosphate cardiovascular toxins in ckd," Toxins, Nov. 6, 2019, 11(11):647.
Von Massenhausen et al., "Evaluation of FGFR3 as a Therapeutic Target in Head and Neck Squamous Cell Carcinoma," Targ. Oncol., 2016, 11: 631-642.
Walsky and Obach, "Validated assays for human cytochrome P450 activities," Drug Metab Dispos., 2004, 32(6):647-660.
Walsky et al., "Evaluation of 227 drugs for in vitro inhibition of cytochrome P450 2B6," J Clin Pharmacol., Dec. 2006, 46(12):1426-1438.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Wang et al., "The fibroblast growth factor receptor-4 Arg388 allele is associated with prostate cancer initiation and progression," Clin Cancer Res. 2004, 10:6169-6178.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Williams et al., "Oncogenic FGFR3 gene fusions in bladder cancer," Hum Mol Genet, 2013, 22:795-803.
Wu, "Urothelial Tumorigenesis: A Tale Of Divergent Pathways," Nature Reviews, Sep. 2005, 5: 713-725.
Wuts et al., "Greene's Protective Groups in Organic Synthesis," 4th Ed., 2006, Chapter 7, 696-926.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in A Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Xu et. al. "Design, synthesis and biological evaluation of deuterated nintedanib for improving pharmacokinetic properties," J Label Compd Radiopharm., 2015, 58(7):308-312.

(56) References Cited

OTHER PUBLICATIONS

Ye et al., "Combination of the FGFR4 inhibitor PD173074 and 5-fluorouracil reduces proliferation and promotes apoptosis in gastric cancer," Oncol Rep., Dec. 2013, 30(6):2777-2784.

Ying et al., "Genome-wide screening for genetic alterations in esophageal cancer by aCGH identifies 11q13 amplification oncogenes associated with nodal metastasis," PLoS One, Jun. 25, 2012, 7:e39797.

Yu et al., "Amorphous pharmaceutical solids: preparation, characterization and stabilization," Advanced Drug Delivery Reviews, May 16, 2001, 48(1):27-42.

Yu et al., "Analysis of the Biochemical Mechanisms for the Endocrine Actions of Fibroblast Growth Factor-23," Endocrinology, Nov. 2005, 146(11): 4647-4656.

Yu et al., "FGFR-4 Arg(3)(8)(8) enhances prostate cancer progression via extracellular signal-related kinase and serum response factor signaling," Clin Cancer Res., Jul. 2011, 17:4355-4366.

Zaid et al., "Identification of FGFR4 as a Potential Therapeutic Target for Advanced-Stage, High-Grade Serous Ovarian Cancer," Clin Cancer Res, 2013, 19(4): 809-820.

Zhang et al., "AZD4547, a potent and selective FGF-receptor inhibitor induces tumor regressions in a human primary model of FGF-receptor 2 amplified gastric cancer and is efficacious in combination with chemotherapy," 2012, AstraZeneca, 1 page.

Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.

Zhang et al., "Enhanced FGFR signalling predisposes pancreatic cancer to the effect of a potent FGFR inhibitor in preclinical models," British Journal of Cancer, 2014, 110: 320-329.

Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.

Zhang et al., "Predicting Drug-Drug Interactions: An FDA Perspective," The AAPS Journal, May 6, 2009, 11(2):300-306.

Zhang et al., "Recent progress in therapeutic and diagnostic applications of lanthanides," Mini-Reviews in Medicinal Chemistry, 2011, 11(8):678-694.

Zhang et al., "Receptor Specificity of the Fibroblast Growth Factor Family," Journal of Biological Chemistry, Jun. 2006, 281(23): 15694-15700.

Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.

Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.

Zhao et al., "Homozygous Deletions and Chromosome Amplifications in Human Lung Carcinomas Revealed by Single Nucleotide Polymorphism Array Analysis," Cancer Res, Jul. 2005, 5561-5570.

Zhou et al., "A Structure-Guided Approach to Creating Covalent FGFR Inhibitors," Chemistry and Biology, Mar. 2010, 285-295.

Zhu et al., "Fibroblast growth factor receptor 3 inhibition by short hairpin RNAs leads to apoptosis in multiple myeloma," Mol Cancer Ther, May 2005, 787-798.

Zieger et al., "Role of Activating Fibroblast Growth Factor Receptor 3 Mutations in the Development of Bladder Tumors," Clin Cancer Res, Nov. 2005, 7709-7719.

Zingone et al., "Ectopic expression of wild-type FGFR3 cooperates with MYC to accelerate development of B-cell lineage neoplasms," Leukemia, 2010, 1171-1178.

Chinese Office Action in Chinese Application No. 2020800850230, dated Apr. 12, 2024, 12 pages (with English Translation).

Indonesian Office Action in Indonesian Application No. P00202205354, dated Nov. 30, 2023, 8 pages (with English Translation).

International Preliminary Report on Patentability in International Appln. No. PCT/US2022/032603, mailed on Dec. 21, 2023, 7 pages.

International Preliminary Report on Patentability in International Appln. No. PCT/US2022/032604, mailed on Dec. 21, 2023, 8 pages.

International Search Report and Written Opinion for International Appln. No. PCT/US2022/053582 mailed Jun. 2, 2023, 17 pages.

Office Action in Chilean Appln. No. 2022-000923, dated Aug. 21, 2023, 26 pages (with Machine Translation).

Office Action in Georgian Appln. No. 202015945, dated Aug. 31, 2023, 7 pages (with English Translation).

Petursson et al., "Protecting Groups in Carbohydrate Chemistry," J. Chem. Education, Nov. 1997, 74(11):1297-1303.

Saudi Arabian Office Action in Saudi Arabian Application No. 522432263, dated Mar. 17, 2024, 6 pages (with English Translation).

Shah et al., "The role of fluorine in medicinal chemistry," Journal of Enzyme Inhibition and Medicinal Chemistry, Oct. 2007, 22(5):527-540.

\* cited by examiner

TRICYCLIC HETEROCYCLES AS FGFR INHIBITORS

FIELD

The present disclosure relates to tricyclic heterocycles, and pharmaceutical compositions of the same, that are inhibitors of the enzyme FGFR and are useful in the treatment of FGFR-associated diseases such as cancer.

SEQUENCE LISTING

This application contains a Sequence Listing that has been submitted electronically as an ASCII text file named "Sequence_Listing.txt." The ASCII text file, created on Jun. 6, 2022, is 1 kilobyte in size. The material in the ASCII text file is hereby incorporated by reference in its entirety.

BACKGROUND

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005, 16, 139-149). Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described (Reviewed in Knights and Cook, Pharmacology & Therapeutics, 2010, 125, 105-117; Turner and Grose, Nature Reviews Cancer, 2010, 10, 116-129). Large scale DNA sequencing of thousands of tumor samples has revealed that FGFR genes are altered in many cancers (Helsten et al. Clin Cancer Res. 2016, 22, 259-267). Some of these activating mutations are identical to germline mutations that lead to skeletal dysplasia syndromes (Gallo et al. Cytokine & Growth Factor Reviews 2015, 26, 425-449). Mechanisms that lead to aberrant ligand-dependent signaling in human disease include overexpression of FGFs and changes in FGFR splicing that lead to receptors with more promiscuous ligand binding abilities. Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, colorectal, endometrial, gastric, head and neck, kidney, lung, ovarian, prostate); hematopoietic malignancies (e.g., multiple myeloma, acute myelogenous leukemia, and myeloproliferative neoplasms); and other neoplasms (e.g., glioblastoma and sarcomas). In addition to a role in oncogenic neoplasms, FGFR activation has also been implicated in skeletal and chondrocyte disorders including, but not limited to, achrondroplasia and craniosynostosis syndromes.

There is a continuing need for the development of new drugs for the treatment of cancer, and the FGFR inhibitors described herein help address this need.

SUMMARY

The present disclosure is directed to compounds having Formula I:

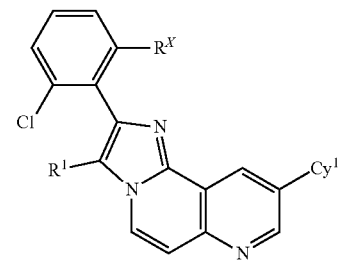

or pharmaceutically acceptable salts thereof, wherein constituent variables are defined herein.

The present disclosure is further directed to pharmaceutical compositions comprising a compound of Formula (I), or a pharmaceutically acceptable salt thereof, and at least one pharmaceutically acceptable carrier.

The present disclosure is further directed to methods of inhibiting an FGFR enzyme (e.g., an FGFR3 enzyme) comprising contacting the enzyme with a compound of Formula (I), or a pharmaceutically acceptable salt thereof.

The present disclosure is further directed to a method of treating a disease associated with abnormal activity or expression of an FGFR enzyme (e.g., an FGFR3 enzyme), comprising administering a compound of Formula (I), or a pharmaceutically acceptable salt thereof, to a patient in need thereof.

The present disclosure is further directed to compounds of Formula (I) for use in treating a disease associated with abnormal activity or expression of an FGFR enzyme (e.g., an FGFR3 enzyme). The present disclosure is further directed to the use of compounds of Formula (I) in the preparation of a medicament for use in therapy.

The present disclosure is further directed to a method for treating a disorder mediated by an FGFR enzyme (e.g., an FGFR3 enzyme), or a mutant thereof, in a patient in need thereof, comprising the step of administering to said patient a compound of Formula (I), or pharmaceutically acceptable composition thereof.

The present disclosure is further directed to a method for treating a disorder mediated by an FGFR enzyme (e.g., an FGFR3 enzyme), or a mutant thereof, in a patient in need thereof, comprising the step of administering to the patient a compound of Formula (I), or a pharmaceutically acceptable salt thereof, or a composition comprising a compound of Formula (I), or a pharmaceutically acceptable salt thereof, in combination with another therapy or therapeutic agent as described herein.

DETAILED DESCRIPTION

Compounds

In one aspect, the present disclosure provides compounds of Formula I:

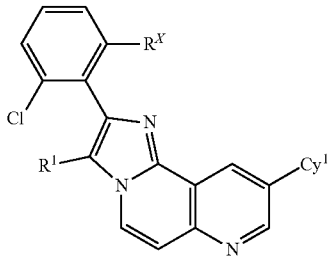

or a pharmaceutically acceptable salt thereof, wherein:
$R^X$ is selected from methyl and Cl;
$Cy^1$ is selected from

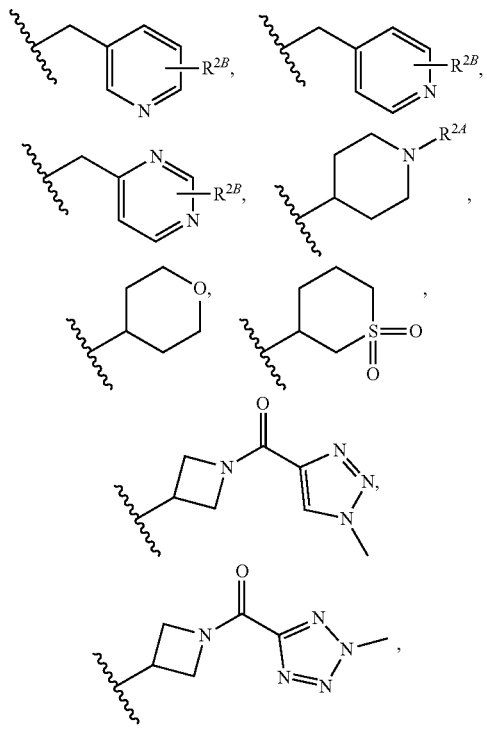

$R^1$ is selected from $CH_2OH$, $CH_2CH_2OH$, $CHF_2$, $NH_2$, and $CH_3$;
$R^2$ is selected from ethyl, —($C_{1-4}$ alkyl)-OH, —($C_{1-3}$ alkyl)-CN, ($C_{1-3}$ alkyl)-C(O)$NH_2$, —($C_{1-4}$ alkyl)-C(O)N($CH_3$)$_2$, $CH_2CH_2S(O)_2CH_3$, and the following groups:

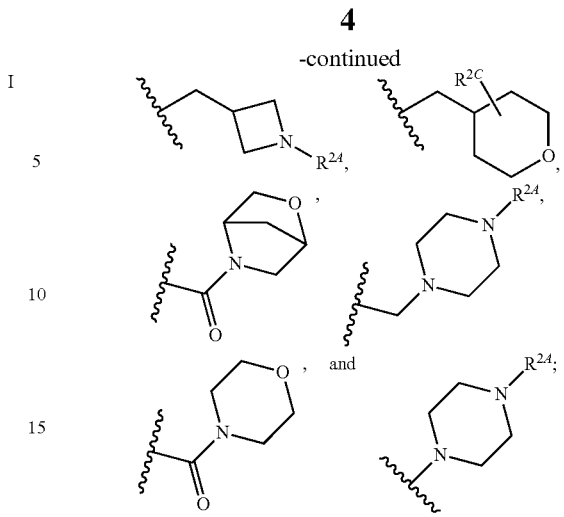

$R^{2A}$ is selected from $CH_3$, $C(O)CH_3$, $C(O)CH_2OCH_3$, and $C(O)CH_2OH$;
$R^{2B}$ is selected from H, CN, $CF_3$, and $C(O)N(CH_3)_2$; and
$R^{2C}$ is selected from H and F;
provided that the compound is not:
2-(2,6-Dichlorophenyl)-3-methyl-9-(1-(tetrahydro-2H-pyran-4-yl)-1H-pyrazol-4-yl)imidazo[2,1-f][1,6]naphthyridine,
3-(4-(2-(2,6-Dichlorophenyl)-3-(hydroxymethyl)imidazo[2,1-f][1,6]naphthyridin-9-yl)-1H-pyrazol-1-yl)propanenitrile,
1-(4-(2-(2,6-Dichlorophenyl)-3-(hydroxymethyl)imidazo[2,1-f][1,6]naphthyridin-9-yl)-1H-pyrazol-1-yl)-2-methylpropan-2-ol,
2-(4-(2-(2,6-Dichlorophenyl)-3-(hydroxymethyl)imidazo[2,1-f][1,6]naphthyridin-9-yl)-1H-pyrazol-1-yl)acetonitrile,
(2-(2,6-Dichlorophenyl)-9-(1-(1-methylpiperidin-4-yl)-1H-pyrazol-4-yl)imidazo[2,1-f][1,6]naphthyridin-3-yl)methanol,
2-(4-(2-(2,6-Dichlorophenyl)-3-(hydroxymethyl)imidazo[2,1-f][1,6]naphthyridin-9-yl)-1H-pyrazol-1-yl)-2-methylpropan-1-ol,
(2-(2,6-Dichlorophenyl)-9-(1-(2-(methylsulfonyl)ethyl)-1H-pyrazol-4-yl)imidazo[2,1-f][1,6]naphthyridin-3-yl)methanol, or
2-(4-(2-(2,6-Dichlorophenyl)-3-(hydroxymethyl)imidazo[2,1-f][1,6]naphthyridin-9-yl)-1H-pyrazol-1-yl)ethan-1-ol.

In some embodiments, $R^X$ is methyl.
In some embodiments, $R^X$ is Cl.
In some embodiments, $Cy^1$ is $Cy^1$-1:

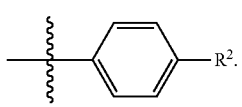

In some embodiments, $Cy^1$ is $Cy^1$-2:

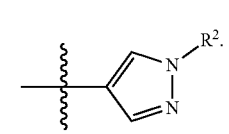

In some embodiments, R¹ is selected from CH₂CH₂OH, CHF₂, and NH₂.

In some embodiments, R¹ is selected from CH₂OH and CH₂CH₂OH.

In some embodiments, R¹ is CH₂OH. In some embodiments, R¹ is CH₂CH₂OH. In some embodiments, R¹ is CHF₂. In some embodiments, R¹ is NH₂. In some embodiments, R¹ is CH₃.

In some embodiments, R² is selected from ethyl, CH(CH₃)CH₂OH, CH₂CH(CH₃)OH, CH(CH₃)CH₂CN, C(CH₃)₂CN, CH(CH₃)CN, C(CH₃)₂C(O)NH₂, CH₂C(O)N(CH₃)₂, and the following groups:

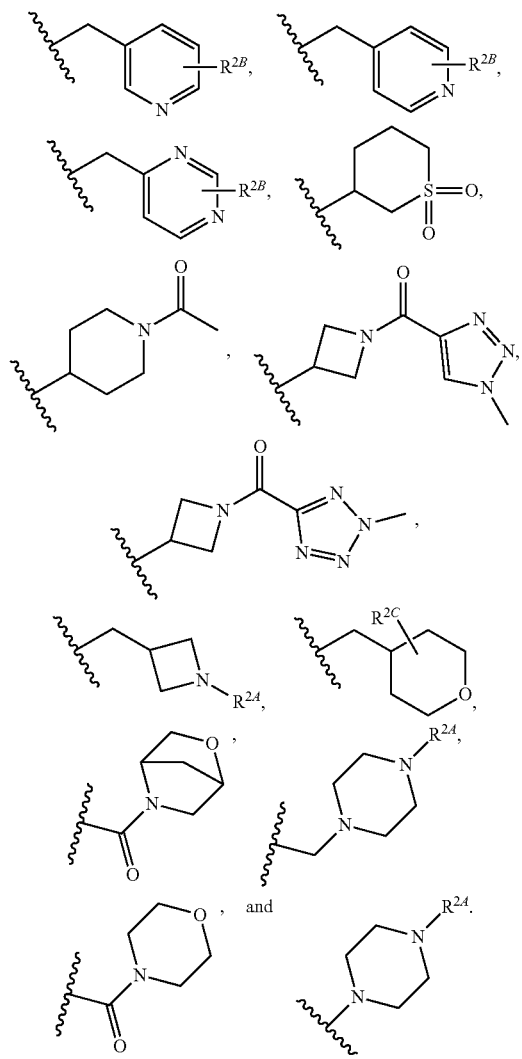

In some embodiments, R² is selected from ethyl, —(C₁₋₄ alkyl)-OH, —(C₁₋₃ alkyl)-CN, (C₁₋₃ alkyl)-C(O)NH₂, —(C₁₋₄ alkyl)-C(O)N(CH₃)₂, and CH₂CH₂S(O)₂CH₃.

In some embodiments, wherein R² is selected from ethyl, CH(CH₃)CH₂OH, CH₂CH(CH₃)OK, CH(CH₃)CH₂CN, C(CH₃)₂CN, CH(CH₃)CN, C(CH₃)₂C(O)NH₂, and CH₂C(O)N(CH₃)₂.

In some embodiments, R² is selected from the following groups:

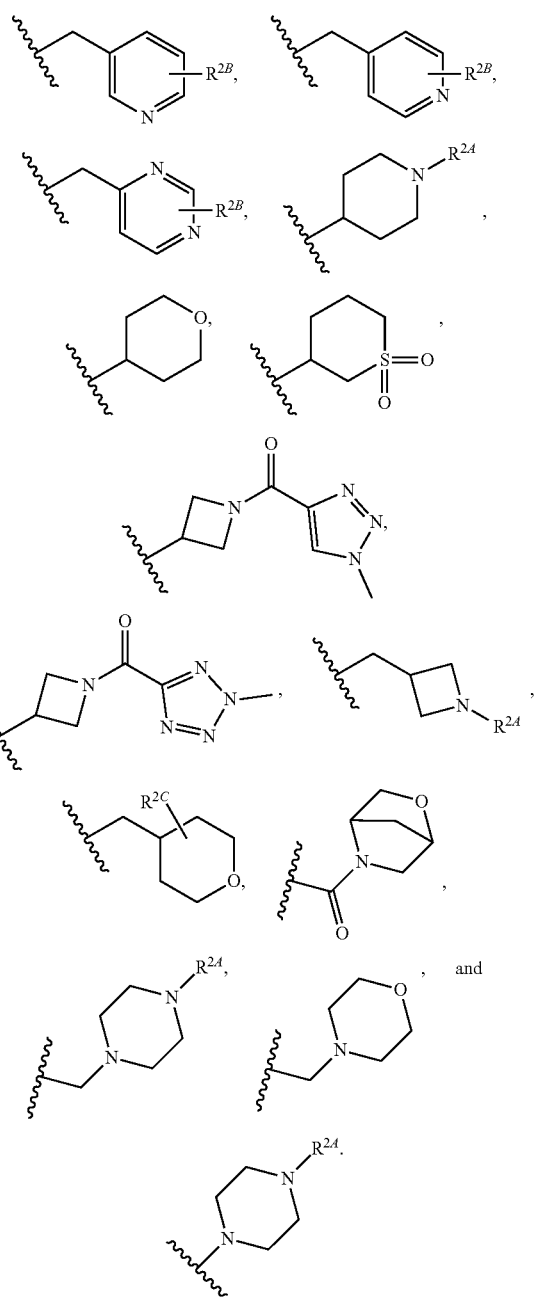

In some embodiments, R² is selected from the following groups:

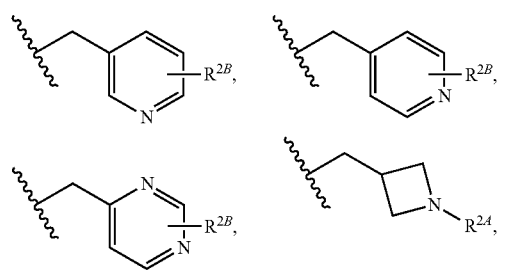

-continued

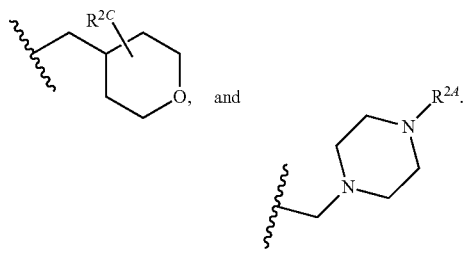

In some embodiments, R² is selected from the following groups:

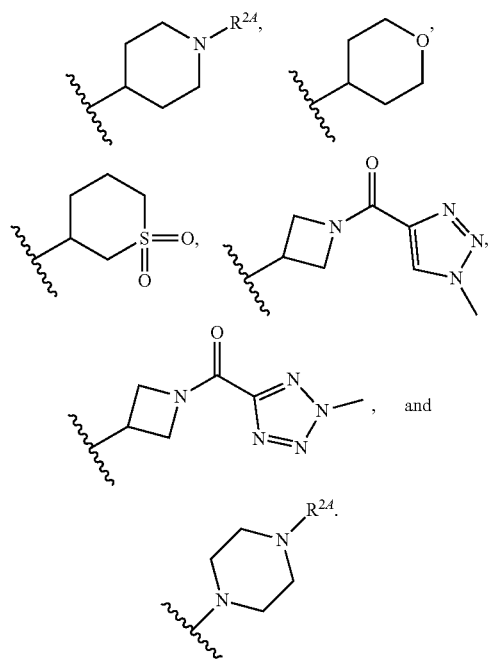

In some embodiments, R² is selected from the following groups:

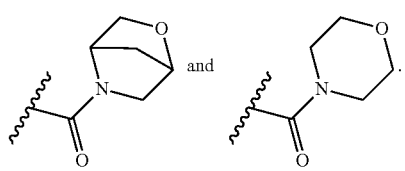 [SMILES: *C(=O)N1CC2CC1CO2 ; *C(=O)N1CCOCC1]

In some embodiments, $R^{2A}$ is CH₃.

In some embodiments, $R^{2A}$ is selected from C(O)CH₃, C(O)CH₂OCH₃, and C(O)CH₂OH.

In some embodiments, $R^{2B}$ is selected from CN, CF₃, and C(O)N(CH₃)₂.

In some embodiments, $R^{2B}$ is H.

In some embodiments, $R^{2C}$ is F.

In some embodiments, $R^{2C}$ is H.

In one aspect, the present disclosure provides compounds of Formula I:

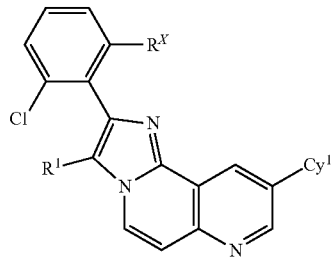

I or a pharmaceutically acceptable salt thereof, wherein:

$R^X$ is selected from methyl and Cl;

$Cy^1$ is selected from

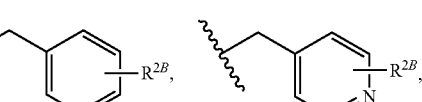

Cy¹-1

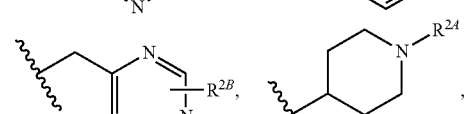

Cy¹-2

$R^1$ is selected from CH₂OH, CH₂CH₂OH, CHF₂, NH₂, and CH₃;

$R^2$ is selected from ethyl, —(C₁₋₄ alkyl)-OH, —(C₁₋₃ alkyl)-CN, (C₁₋₃ alkyl)-C(O)NH₂, —(C₁₋₄ alkyl)-C(O)N(CH₃)₂, CH₂CH₂S(O)₂CH₃, and the following groups:

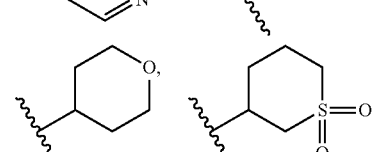

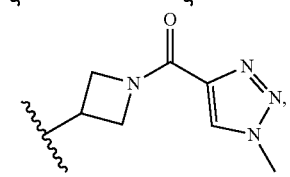

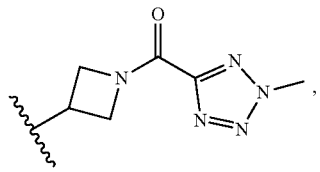

-continued

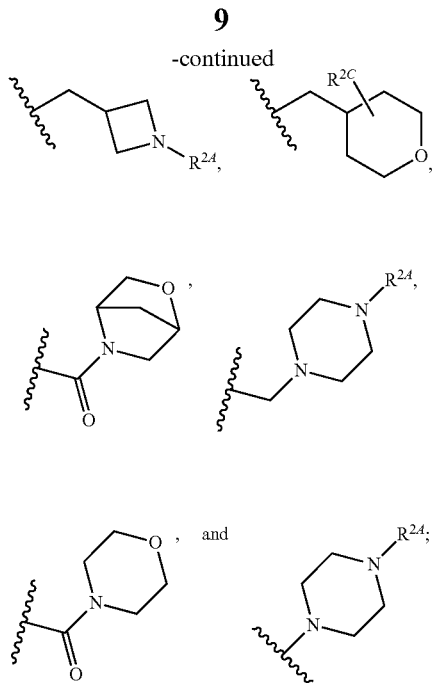

$R^{2A}$ is selected from $CH_3$, $C(O)CH_3$, $C(O)CH_2OCH_3$, and $C(O)CH_2OH$;

$R^{2B}$ is selected from H, CN, $CF_3$, and $C(O)N(CH_3)_2$; and $R^{2C}$ is selected from H and F;

provided that:

(a) when $R^1$ is $CH_3$, then $R^2$ is other than tetrahydro-2H-pyran-4-yl; and (b) when $R^1$ is $CH_2OH$ and $R^X$ is Cl, then $R^2$ is other than $CH_2CN$, $CH_2CH_2CN$, $CH_2C(CH_3)_2OH$, $C(CH_3)_2CH_2OH$, $CH_2CH_2OH$, $CH_2CH_2S(O)_2CH_3$, and

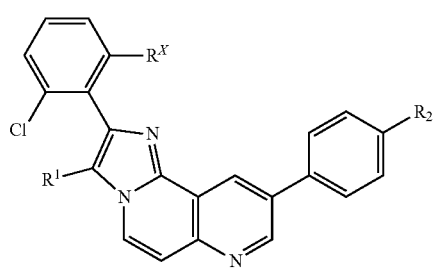

In one aspect, the present disclosure provides compounds of Formula IIa:

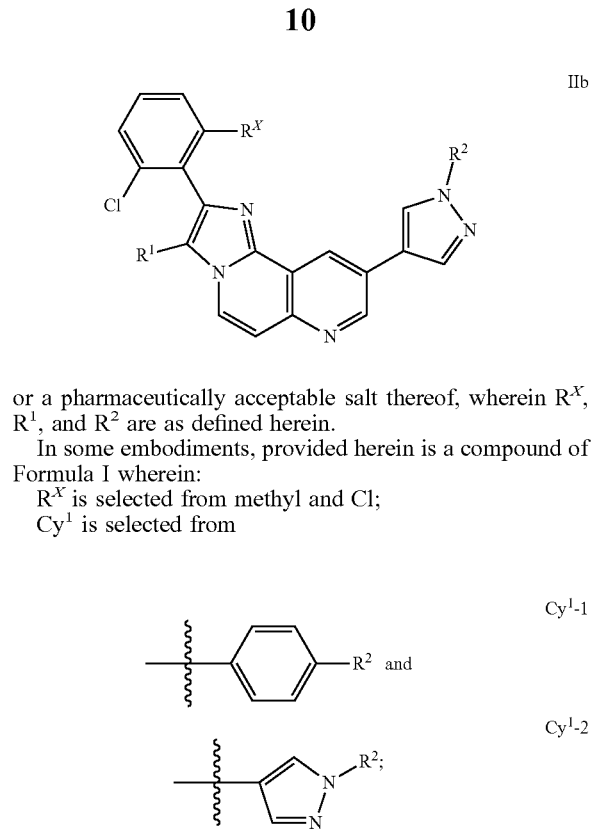

or a pharmaceutically acceptable salt thereof, wherein $R^X$, $R^1$, and $R^2$ are as defined herein.

In one aspect, the present disclosure provides compounds of Formula IIb:

or a pharmaceutically acceptable salt thereof, wherein $R^X$, $R^1$, and $R^2$ are as defined herein.

In some embodiments, provided herein is a compound of Formula I wherein:

$R^X$ is selected from methyl and Cl;

$Cy^1$ is selected from

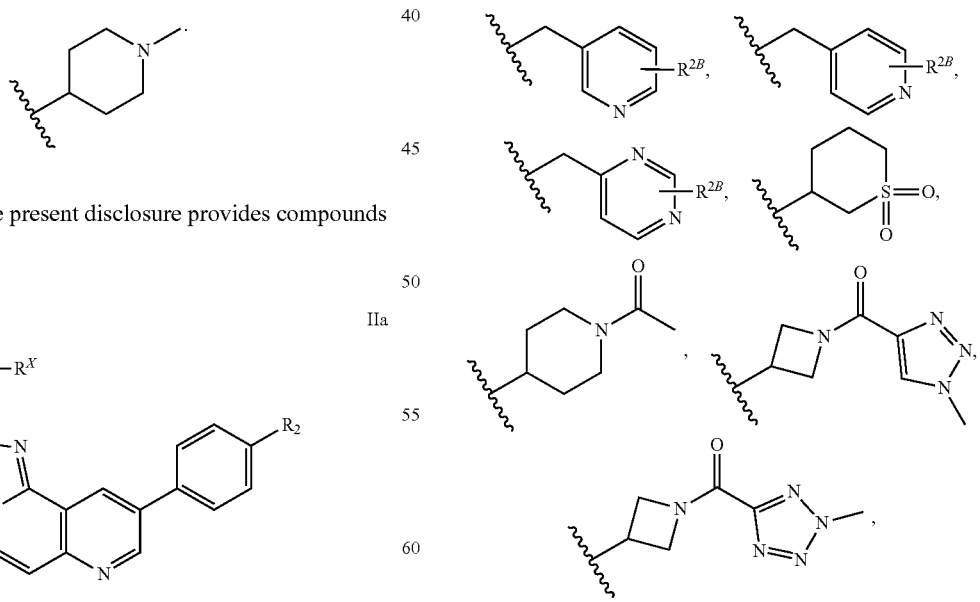

$R^1$ is selected from $CH_2OH$, $CH_2CH_2OH$, $CHF_2$, $NH_2$, and $CH_3$;

$R^2$ is selected from ethyl, $CH(CH_3)CH_2OH$, $CH_2CH(CH_3)OH$, $CH(CH_3)CH_2CN$, $C(CH_3)_2CN$, $CH(CH_3CN$, $C(CH_3)_2C(O)NH_2$, $CH_2C(O)N(CH_3)_2$ and the following groups:

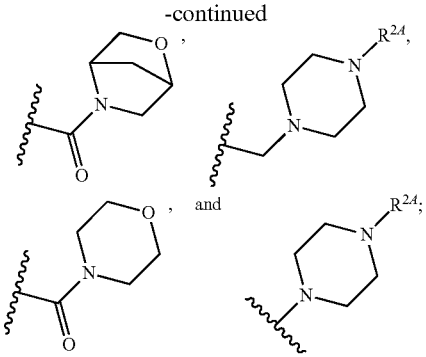

$R^{2A}$ is selected from $CH_3$, $C(O)CH_3$, $C(O)CH_2OCH_3$, and $C(O)CH_2OH$;

$R^{2B}$ is selected from H, CN, $CF_3$, and $C(O)N(CH_3)_2$; and $R^{2C}$ is selected from H and F.

In some embodiments, provided herein is a compound of Formula I wherein:

$R^X$ is selected from methyl and Cl;

$Cy^1$ is selected from

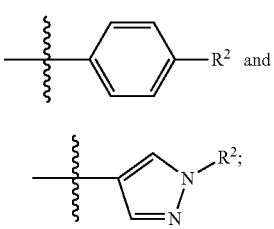

$R^1$ is selected from $CH_2CH_2OH$, $CHF_2$, and $NH_2$;

$R^2$ is selected from ethyl, —($C_{1-4}$ alkyl)-OH, —($C_{1-3}$ alkyl)-CN, ($C_{1-3}$ alkyl)-$C(O)NH_2$, —($C_{1-4}$ alkyl)-$C(O)N(CH_3)_2$, $CH_2CH_2S(O)_2CH_3$, and the following groups:

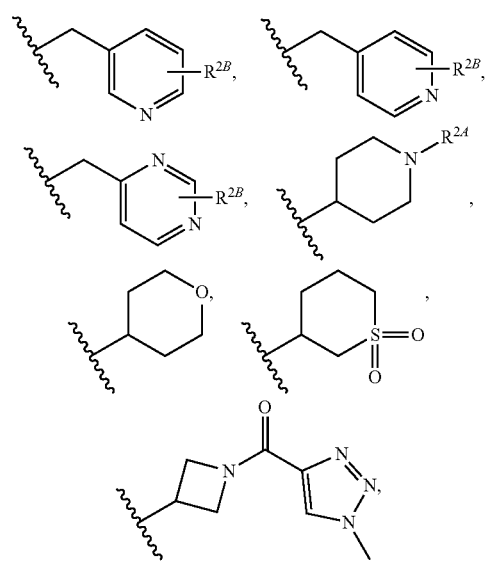

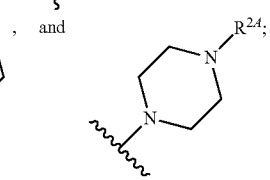

$R^{2A}$ is selected from $CH_3$, $C(O)CH_3$, $C(O)CH_2OCH_3$, and $C(O)CH_2OH$;

$R^{2B}$ is selected from H, CN, $CF_3$, and $C(O)N(CH_3)_2$; and $R^{2C}$ is selected from H and F.

In some embodiments, provided herein is a compound of Formula I wherein:

$R^X$ is $CH_3$;

$Cy^1$ is selected from

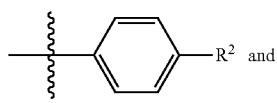

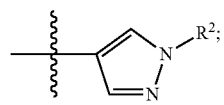

$R^1$ is selected from $CH_2OH$, $CH_2CH_2OH$, $CHF_2$, $NH_2$, and $CH_3$;

$R^2$ is selected from ethyl, —($C_{1-4}$ alkyl)-OH, —($C_{1-3}$ alkyl)-CN, ($C_{1-3}$ alkyl)-$C(O)NH_2$, —($C_{1-4}$ alkyl)-$C(O)N(CH_3)_2$, $CH_2CH_2S(O)_2CH_3$, and the following groups:

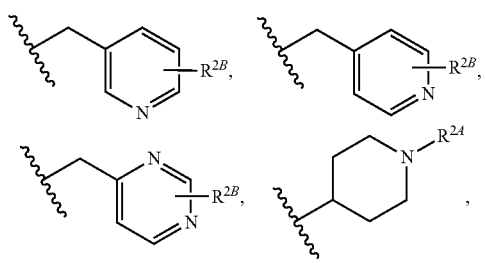

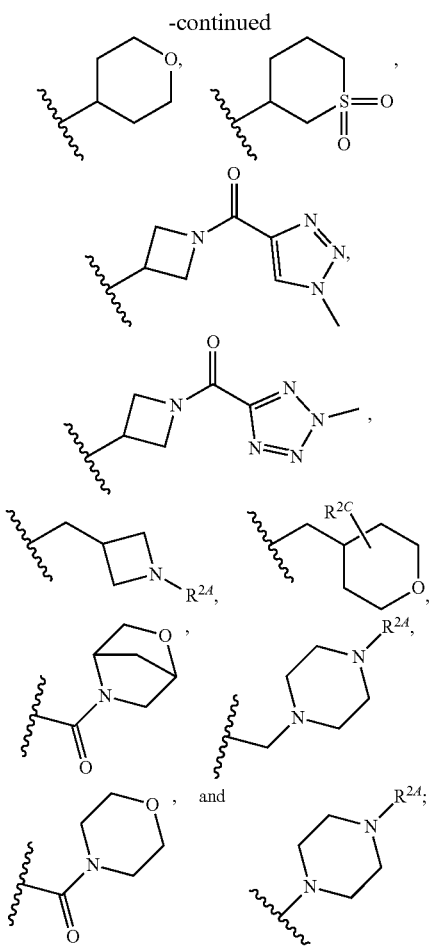

$R^{2A}$ is selected from CH$_3$, C(O)CH$_3$, C(O)CH$_2$OCH$_3$, and C(O)CH$_2$OH;
$R^{2B}$ is selected from H, CN, CF$_3$, and C(O)N(CH$_3$)$_2$; and
$R^{2C}$ is selected from H and F.

In some embodiments, provided herein is a compound of Formula I which is selected from:

(2-(2,6-Dichlorophenyl)-9-(1-(pyrimidin-4-ylmethyl)-1H-pyrazol-4-yl)imidazo[2,1-f][1,6]naphthyridin-3-yl)methanol;

5-((4-(2-(2,6-Dichlorophenyl)-3-(hydroxymethyl)imidazo[2,1-f][1,6]naphthyridin-9-yl)-1H-pyrazol-1-yl)methyl)nicotinonitrile;

5-((4-(2-(2,6-Dichlorophenyl)-3-(hydroxymethyl)imidazo[2,1-f][1,6]naphthyridin-9-yl)-1H-pyrazol-1-yl)methyl)picolinonitrile;

4-((4-(2-(2,6-Dichlorophenyl)-3-(hydroxymethyl)imidazo[2,1-f][1,6]naphthyridin-9-yl)-1H-pyrazol-1-yl)methyl)picolinonitrile;

(2-(2,6-Dichlorophenyl)-9-(1-((2-(trifluoromethyl)pyridin-4-yl)methyl)-1H-pyrazol-4-yl)imidazo[2,1-f][1,6]naphthyridin-3-yl)methanol;

(4-(2-(2,6-Dichlorophenyl)-3-(hydroxymethyl)imidazo[2,1-][1,6]naphthyridin-9-yl)phenyl)(morpholino)methanone;

((1S,4S)-2-Oxa-5-azabicyclo[2.2.1]heptan-5-yl)(4-(2-(2,6-dichlorophenyl)-3-(hydroxymethyl)imidazo[2,1-f][1,6]naphthyridin-9-yl)phenyl)methanone;

1-(4-(4-(2-(2,6-Dichlorophenyl)-3-(hydroxymethyl)imidazo[2,1-f][1,6]naphthyridin-9-yl)benzyl)piperazin-1-yl)-2-hydroxyethan-1-one;

1-(4-(4-(2-(2,6-Dichlorophenyl)-3-(hydroxymethyl)imidazo[2,1-f][1,6]naphthyridin-9-yl)benzyl)piperazin-1-yl)ethan-1-one;

1-(4-(4-(2-(2,6-Dichlorophenyl)-3-(hydroxymethyl)imidazo[2,1-f][1,6]naphthyridin-9-yl)phenyl)piperazin-1-yl)-2-hydroxyethan-1-one;

(2-(2-Chloro-6-methylphenyl)-9-(1-(1-methylpiperidin-4-yl)-1H-pyrazol-4-yl)imidazo[2,1-f][1,6]naphthyridin-3-yl)methanol;

5-((4-(2-(2,6-Dichlorophenyl)-3-(hydroxymethyl)imidazo[2,1-][1,6]naphthyridin-9-yl)-1H-pyrazol-1-yl)methyl)-N,N-dimethylpicolinamide;

(3-(4-(2-(2,6-Dichlorophenyl)-3-methylimidazo[2,1-][1,6]naphthyridin-9-yl)-1H-pyrazol-1-yl)azetidin-1-yl)(1-methyl-1H-1,2,3-triazol-4-yl)methanone;

(3-(4-(2-(2,6-Dichlorophenyl)-3-methylimidazo[2,1-f][1,6]naphthyridin-9-yl)-1H-pyrazol-1-yl)azetidin-1-yl)(2-methyl-2H-tetrazol-5-yl)methanone;

(2-(2,6-Dichlorophenyl)-9-(1-ethyl-1H-pyrazol-4-yl)imidazo[2,1-f][1,6]naphthyridin-3-yl)methanol;

2-(4-(2-(2,6-Dichlorophenyl)-3-(hydroxymethyl)imidazo[2,1-f][1,6]naphthyridin-9-yl)-1H-pyrazol-1-yl)-2-methylpropanenitrile;

2-(4-(2-(2,6-Dichlorophenyl)-3-(hydroxymethyl)imidazo[2,1-f][1,6]naphthyridin-9-yl)-1H-pyrazol-1-yl)propanenitrile;

1-(4-(2-(2,6-Dichlorophenyl)-3-(hydroxymethyl)imidazo[2,1-f][1,6]naphthyridin-9-yl)-1H-pyrazol-1-yl)propan-2-ol;

2-(4-(2-(2,6-Dichlorophenyl)-3-(hydroxymethyl)imidazo[2,1-][1,6]naphthyridin-9-yl)-1H-pyrazol-1-yl)-N,N-dimethylacetamide;

1-(4-(4-(2-(2,6-Dichlorophenyl)-3-(hydroxymethyl)imidazo[2,1-f][1,6]naphthyridin-9-yl)-1H-pyrazol-1-yl)piperidin-1-yl)ethan-1-one;

1-(4-(4-(2-(2-Chloro-6-methylphenyl)-3-(hydroxymethyl)imidazo[2,1-][A1,6]naphthyridin-9-yl)-1H-pyrazol-1-yl)piperidin-1-yl)-2-methoxyethan-1-one;

1-(4-(2-(2-Chloro-6-methylphenyl)-3-(hydroxymethyl)imidazo[2,1-f][1,6]naphthyridin-9-yl)-1H-pyrazol-1-yl)-2-methylpropan-2-ol;

3-(4-(2-(2,6-Dichlorophenyl)-3-(hydroxymethyl)imidazo[2,1-][1,6]naphthyridin-9-yl)-1H-pyrazol-1-yl)butanenitrile;

(R)-2-(4-(2-(2,6-Dichlorophenyl)-3-(hydroxymethyl)imidazo[2,1-][1,6]naphthyridin-9-yl)-1H-pyrazol-1-yl)propan-1-ol;

(2-(2,6-Dichlorophenyl)-9-(1-((4-fluorotetrahydro-2H-pyran-4-yl)methyl)-1H-pyrazol-4-yl)imidazo[2,1-][1,6]naphthyridin-3-yl)methanol;

3-(4-(2-(2,6-Dichlorophenyl)-3-(hydroxymethyl)imidazo[2,1-f][1,6]naphthyridin-9-yl)-1H-pyrazol-1-yl)tetrahydro-2H-thiopyran 1,1-dioxide;

1-(3-((4-(2-(2,6-Dichlorophenyl)-3-(hydroxymethyl)imidazo[2,1-f][1,6]naphthyridin-9-yl)-1H-pyrazol-1-yl)methyl)azetidin-1-yl)-2-methoxyethan-1-one;

2-(2,6-Dichlorophenyl)-3-(difluoromethyl)-9-(1-(2-(methylsulfonyl)ethyl)-1H-pyrazol-4-yl)imidazo[2,1-][1,6]naphthyridine;

2-(4-(2-(2,6-Dichlorophenyl)-3-(difluoromethyl)imidazo[2,1-][1,6]naphthyridin-9-yl)-1H-pyrazol-1-yl)acetonitrile;

2-(2,6-Dichlorophenyl)-3-(difluoromethyl)-9-(1-(tetrahydro-2H-pyran-4-yl)-1H-pyrazol-4-yl)imidazo[2,1-][1,6]naphthyridine;

2-(4-(2-(2,6-Dichlorophenyl)-3-(difluoromethyl)imidazo[2,1-f][1,6]naphthyridin-9-yl)-1H-pyrazol-1-yl)ethan-1-ol;

2-(4-(2-(2,6-Dichlorophenyl)-3-(difluoromethyl)imidazo[2,1-f][1,6]naphthyridin-9-yl)-1H-pyrazol-1-yl)propanenitrile;

2-(4-(2-(2,6-Dichlorophenyl)-3-(difluoromethyl)imidazo[2,1-][1,6]naphthyridin-9-yl)-1H-pyrazol-1-yl)-2-methyl-propanamide;

2-(2-(2,6-Dichlorophenyl)-9-(1-(1-methylpiperidin-4-yl)-1H-pyrazol-4-yl)imidazo[2,1-f][1,6]naphthyridin-3-yl)ethan-1-ol; and 2-(2,6-Dichlorophenyl)-9-(1-(tetrahydro-2H-pyran-4-yl)-1H-pyrazol-4-yl)imidazo[2,1-][1,6]naphthyridin-3-amine, or a pharmaceutically salt of any of the aforementioned.

It is further appreciated that certain features of the disclosure, which are, for clarity, described in the context of separate embodiments, can also be provided in combination in a single embodiment Conversely, various features of the disclosure which are, for brevity, described in the context of a single embodiment, can also be provided separately or in any suitable subcombination.

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

For compounds of the disclosure in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. A single divalent substituent, e.g., oxo, can replace two hydrogen atoms.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. An alkyl group formally corresponds to an alkane with one C—H bond replaced by the point of attachment of the alkyl group to the remainder of the compound. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, the term "$C_{i-j}$ alkylene," employed alone or in combination with other terms, means a saturated divalent linking hydrocarbon group that may be straight-chain or branched, having i to j carbons. In some embodiments, the alkylene group contains from 1 to 4 carbon atoms, from 1 to 3 carbon atoms, or from 1 to 2 carbon atoms. Examples of alkylene moieties include, but are not limited to, chemical groups such as methylene, ethylene, 1,1-ethylene, 1,2-ethylene, 1,3-propylene, 1,2-propylene, 1,1-propylene, isopropylene, and the like.

The term "cyano" or "nitrile" refers to a group of formula —C≡N, which also may be written as —CN.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

Resolution of racemic mixtures of compounds can be carried out by methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the disclosure have the (R)-configuration. In other embodiments, the compounds have the (S)-configuration. In compounds with more than one chiral centers, each of the chiral centers in the compound may be independently (R) or (S), unless otherwise indicated.

Compounds of the disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the disclosure also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the disclosure can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term, "compound," as used herein is meant to include all stereoisomers, geometric iosomers, tautomers, and isotopes of the structures depicted. The term is also meant to refer to compounds of the disclosure, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., in the form of hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the disclosure, or salts thereof, are substantially isolated. By "substantially isolated" is meant that the compound is at least partially or substantially separated from the environment in which it was formed or detected. Partial separation can include, for example, a composition enriched in the compounds of the disclosure. Substantial separation can include compositions containing at least about 50%, at least about 60%, at least about 70%, at least about 80%, at least about 90%, at least about 95%, at least about 97%, or at least about 99% by weight of the compounds of the disclosure, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography—mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); NIS (N-iodosuccinimide); nM (nanomolar); NMR (nuclear magnetic resonance spectroscopy); OTf (trifluoromethanesulfonate); Pd (palladium); Ph (phenyl); pM (picomolar); PMB (para-methoxybenzyl), POCl$_3$ (phosphoryl chloride); RP-HPLC (reverse phase high performance liquid chromatography); s (singlet); SEM (2-trimethylsilylethoxymethyl); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); µg (microgram(s)); µL (microliter(s)); µM (micromolar); wt % (weight percent).

Synthesis

As will be appreciated by those skilled in the art, the compounds provided herein, including salts and stereoisomers thereof, can be prepared using known organic synthesis techniques and can be synthesized according to any of numerous possible synthetic routes.

The reactions for preparing compounds of the disclosure can be carried out in suitable solvents which can be readily selected by one of skill in the art of organic synthesis.

Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of Formula I can be prepared via the synthetic route as outlined in Scheme 1.

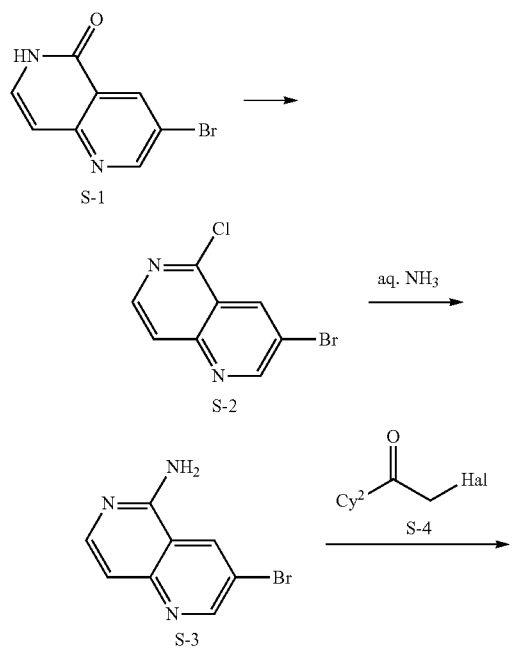

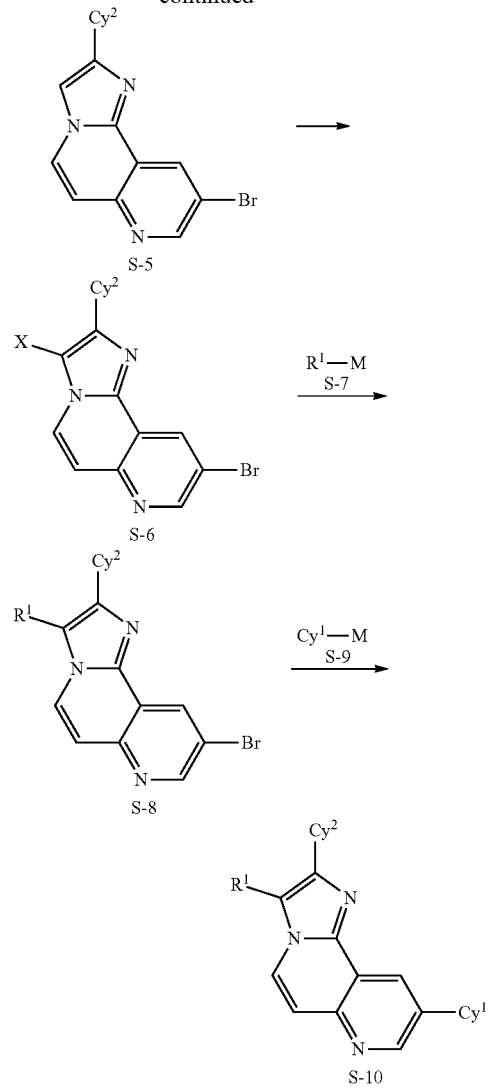

Compounds of formula S-10 can be prepared via the synthetic route as outlined in Scheme 1. Treatment of commercially available compound S-1 with an appropriate reagent, such as phosphoryl chloride (POCl$_3$), at elevated temperature can afford the compound S-2. Chloride displacement of compound S-2 via nucleophilic substitution with aqueous ammonia at elevated temperature can deliver compound S-3. Condensation of compound S-3 with compounds of formula S-4 (Hal is a halide, such as Cl, Br, or I) at elevated temperature can generate compounds S-5, which can undergo a reaction with an appropriate reagent, such as N-iodosuccinimide (NIS) or tert-butyl nitrite, to afford compounds S-6 (X is a substituted nitrogen, or a halide such as Cl, Br, or I). If X is a halide, compounds S-6 can undergo a coupling reaction to an adduct of formula S-7, in which M is a boronic acid, a boronic ester or an appropriate reagent [e.g., M is B(OR)$_2$, Sn(Alkyl)$_3$, Zn-Hal, etc.], under standard Suzuki cross-coupling conditions (e.g., in the presence of a palladium catalyst and a suitable base) (*Tetrahedron* 2002, 58, 9633-9695), or standard Stille cross-coupling conditions (e.g., in the presence of a palladium catalyst) (*ACS Catalysis* 2015, 5, 3040-3053), or standard Negishi cross-coupling conditions (e.g., in the presence of a palladium catalyst)

(*ACS Catalysis* 2016, 6, 1540-1552), to give a derivative of formula S-8. After coupling, if $R^1$ is a vinyl functional group it can be elaborated to a hydroxymethyl, hydroxyethyl, or difluoromethyl substituent using known organic synthesis techniques. Introduction of $Cy^1$ can then be achieved by the coupling of compounds S-8 with an adduct of formula S-9, using similar conditions as described for the preparation of compounds S-8 from compounds S-6, to afford compounds of formula S-10.

Methods of Use

Compounds of the present disclosure can inhibit the activity of the FGFR enzyme. For example, compounds of the present disclosure can be used to inhibit activity of an FGFR enzyme in a cell or in an individual or patient in need of inhibition of the enzyme by administering an inhibiting amount of one or more compounds of the present disclosure to the cell, individual, or patient. Compounds of the present disclosure can be used to inhibit activity of the FGFR3 enzyme in a cell or in an individual or patient in need of inhibition of the enzyme by administering an inhibiting amount of one or more compounds of the present disclosure to the cell, individual, or patient. Compounds of the present disclosure can be used to inhibit activity of the FGFR2 enzyme in a cell or in an individual or patient in need of inhibition of the enzyme by administering an inhibiting amount of one or more compounds of the present disclosure to the cell, individual, or patient. Compounds of the present disclosure can be used to inhibit the activity of an FGFR3 and an FGFR2 enzyme in a cell or in an individual or patient in need of inhibition of the enzyme by administering an inhibiting amount of a compound of the disclosure to the cell, individual, or patient.

As FGFR inhibitors, the compounds of the present disclosure are useful in the treatment of various diseases associated with abnormal expression or activity of the FGFR enzyme or FGFR ligands. Compounds which inhibit FGFR will be useful in providing a means of preventing the growth or inducing apoptosis in tumors, particularly by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In certain embodiments, the disclosure provides a method for treating a FGFR-mediated disorder in a patient in need thereof, comprising the step of administering to said patient a compound according to the invention, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

In some embodiments, cancers that are treatable using the compounds of the present disclosure are selected from adenocarcinoma, bladder cancer, breast cancer, cervical cancer, cholangiocarcinoma, colorectal cancer, endometrial cancer, esophageal cancer, gall bladder cancer, gastric cancer, glioma, head and neck cancer, hepatocellular cancer, kidney cancer, liver cancer, lung cancer, melanoma, ovarian cancer, pancreatic cancer, prostate cancer, rhabdomyosarcoma, skin cancer, thyroid cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, and Burkett's lymphoma.

In some embodiments, cancers that are treatable using the compounds of the present disclosure are selected from hepatocellular cancer, bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

In some embodiments, said cancer is selected from adenocarcinoma, bladder cancer, breast cancer, cervical cancer, cholangiocarcinoma, endometrial cancer, gastric cancer, glioma, head and neck cancer, lung cancer, ovarian cancer, leukemia, and multiple myeloma.

In some embodiments, cancers that are treatable using the compounds of the present disclosure are selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

A cancer characterized by an FGFR2 and/or FGFR3 alteration includes bladder cancers (FGFR3 mutation or fusion), cholangiocarcinoma (FGFR2 fusion) and gastric cancer (FGFR2 amplification).

Compounds of the invention can be used to treat cancer patients with FGFR2/3 alterations, including mutations, fusion, rearrangement, and amplification. FGFR2/3 alterations were found in a subset of cholangiocarcinoma, urothelial carcinoma, multiple myeloma, gastric adenocarcinoma, glioma, endometrial carcinoma, ovarian carcinoma, cervical cancer, lung cancer and breast cancer. Moreover, the compounds of the invention can be used to target patients progressing on pan-FGFR inhibitor treatment due to acquirement of gatekeeper mutations (V555M/U/F/I in FGFR3, V564M/U/F/I in FGFR2). Also Compounds of the invention can be used to treat cancer where FGFR2/3 signaling is involved in the resistance to other targeted therapies, for example, it has the potential to overcome resistance to CDK4/6 inhibitors in ER positive breast cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), 8p11 myeloproliferative syndrome), myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pretumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the invention are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound described herein includes the administration of a compound described herein to an individual or patient, such as a human, having FGFR, as well as, for example, introducing a compound described herein into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy.* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives.* 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with compounds described herein for treatment of FGFR-associated diseases, disorders or conditions, or diseases or conditions as described herein. The agents can be combined with the present compounds in a single dosage form, or the agents can be administered simultaneously or sequentially as separate dosage forms.

Compounds described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the solid forms of the FGFR inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, compounds described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, compounds described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, compounds described herein can be used in combination with targeted therapies, including JAK kinase inhibitors (Ruxolitinib, additional JAK1/2 and JAK1-selective, baricitinib or INCB39110), Pim kinase inhibitors (e.g., LGH447, INCB053914 and SGI-1776), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors (e.g., PLX3397 and LY3022855), TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors, such as OTX015, CPI-0610, INCB54329 or INCB57643), LSD1 inhibitors (e.g., GSK2979552, INCB59872 and INCB60003), arginase inhibitors (e.g., INCB1158), indoleamine 2,3-dioxygenase inhibitors (e.g., epacadostat, NLG919 or BMS-986205), PARP inhibitors (e.g., olaparib or rucaparib), inhibitors of BTK such as ibrutinib, c-MET inhibitors (e.g., capmatinib), an ALK2 inhibitor (e.g., INCB00928); or combinations thereof.

For treating cancer and other proliferative diseases, compounds described herein can be used in combination with chemotherapeutic agents, agonists or antagonists of nuclear receptors, or other anti-proliferative agents. Compounds described herein can also be used in combination with a medical therapy such as surgery or radiotherapy, e.g., gamma-radiation, neutron beam radiotherapy, electron beam radiotherapy, proton therapy, brachytherapy, and systemic radioactive isotopes.

Examples of suitable chemotherapeutic agents include any of: abarelix, abiraterone, afatinib, aflibercept, aldesleukin, alemtuzumab, alitretinoin, allopurinol, altretamine, amidox, amsacrine, anastrozole, aphidicolon, arsenic trioxide, asparaginase, axitinib, azacitidine, bevacizumab, bexarotene, baricitinib, bendamustine, bicalutamide, bleomycin, bortezombi, bortezomib, brivanib, buparlisib, busulfan intravenous, busulfan oral, calusterone, camptosar, capecitabine, carboplatin, carmustine, cediranib, cetuximab, chlorambucil, cisplatin, cladribine, clofarabine, crizotinib, cyclophosphamide, cytarabine, dacarbazine, dacomitinib, dactinomycin, dalteparin sodium, dasatinib, dactinomycin, daunorubicin, decitabine, degarelix, denileukin, denileukin diftitox, deoxycoformycin, dexrazoxane, didox, docetaxel, doxorubicin, droloxafine, dromostanolone propionate, eculizumab, enzalutamide, epidophyllotoxin, epirubicin, epothilones, erlotinib, estramustine, etoposide phosphate, etoposide, exemestane, fentanyl citrate, filgrastim, floxuridine, fludarabine, fluorouracil, flutamide, fulvestrant, gefitinib, gemcitabine, gemtuzumab ozogamicin, goserelin acetate, histrelin acetate, ibritumomab tiuxetan, idarubicin, idelalisib, ifosfamide, imatinib mesylate, interferon alfa 2a, irinotecan, lapatinib ditosylate, lenalidomide, letrozole, leucovorin, leuprolide acetate, levamisole, lonafamib, lomustine, meclorethamine, megestrol acetate, melphalan, mercaptopurine, methotrexate, methoxsalen, mithranycin, mitomycin C, mitotane, mitoxantrone, nandrolone phenpropionate, navelbene, necitumumab, nelarabine, neratinib, nilotinib, nilutamide, niraparib, nofetumomab, oserelin, oxaliplatin, paclitaxel, pamidronate, panitumumab, panobinostat, pazopanib, pegaspargase, pegfilgrastim, pemetrexed disodium, pentostatin, pilaralisib, pipobroman, plicamycin, ponatinib, porfimer, prednisone, procarbazine, quinacrine, ranibizumab, rasburicase, regorafenib, reloxafine, revlimid, rituximab, rucaparib, ruxolitinib, sorafenib, streptozocin, sunitinib, sunitinib maleate, tamoxifen, tegafur, temozolomide, teniposide, testolactone, tezacitabine, thalidomide, thioguanine, thiotepa, tipifamib, topotecan, toremifene, tositumomab, trastuzumab, tretinoin, triapine, trimidox, triptorelin, uracil mustard, valrubicin, vandetanib, vinblastine, vincristine, vindesine, vinorelbine, vorinostat, veliparib, talazoparib, and zoledronate.

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, CDK2, and CDK4/6 kinase inhibitors such as, for example, those described in WO 2006/056399 can be used in combination with the treatment methods and regimens of the present disclosure for treatment of cancers and solid tumors. Other agents such as therapeutic antibodies can be used in combination with the treatment methods and regimens of the present disclosure for treatment of cancers and solid tumors. The one or more additional pharmaceutical agents can be administered to a patient simultaneously or sequentially.

The treatment methods as disclosed herein can be used in combination with one or more other enzyme/protein/receptor inhibitors therapies for the treatment of diseases, such as cancer and other diseases or disorders described herein. For example, the treatment methods and regimens of the present disclosure can be combined with one or more inhibitors of the following kinases for the treatment of cancer: Akt1, Akt2, Akt3, BCL2, CDK2, CDK4/6, TGF-βR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Axl, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Non-limiting examples of inhibitors that can be combined with the treatment methods and regimens of the present disclosure for treatment of cancer include an FGFR inhibitor (FGFR1, FGFR2, FGFR3 or FGFR4, e.g., pemigatinib (INCB54828), INCB62079), an EGFR inhibitor (also known as ErB-1 or HER-1; e.g. erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g. olaparib, rucaparib, veliparib or niraparib), a JAK inhibitor (JAK1 and/or JAK2, e.g., ruxolitinib, baricitinib, itacitinib (INCB39110), an LSD1 inhibitor (e.g., INCB59872 and INCB60003), a TDO inhibitor, a PI3K-delta inhibitor (e.g., INCB50465 and INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Axl, and Mer), an adenosine receptor antagonist (e.g., A2a/A2b receptor antagonist), an HPK1 inhibitor, a chemokine receptor inhibitor (e.g. CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-MET inhibitors (e.g., capmatinib), an anti-CD19 antibody (e.g., tafasitamab), an ALK2 inhibitor (e.g., INCB00928); or combinations thereof.

In some embodiments, the treatment methods described herein are combined with administration of a PI3Kδ inhibitor. In some embodiments, the treatment methods described herein are combined with administration of a JAK inhibitor. In some embodiments, the treatment methods described herein are combined with administration of a JAK1 or JAK2 inhibitor (e.g., baricitinib or ruxolitinib). In some embodiments, the treatment methods described herein are combined with administration of a JAK1 inhibitor. In some embodiments, the treatment methods described herein are combined with administration of a JAK1 inhibitor, which is selective over JAK2.

Example antibodies that can be administered in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be administered to a patient in combination with the treatment methods of the present disclosure and are presented as a non-limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, lerozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sm11, fludarabine, pentostatin, triapine, didox, trimidox, amidox, 3-AP, and MDL-101,731.

The treatment methods and regimens of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-I agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epacadostat, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, BI853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharmaceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the treatment methods of the disclosure can be used in combination with a chemotherapeutic in the treatment of cancer, and may improve the treatment response as compared to the response to the chemotherapeutic agent alone, without exacerbation of its toxic effects. In some embodiments, the treatment methods of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining treatment methods of the present disclosure with an additional agent.

The agents can be combined with Compound 1 and/or antibody that binds to human PD-1 or human PD-L1, or antigen-binding fragment thereof, of the present treatment methods in a single or continuous dosage form, or the agents can be administered simultaneously or sequentially as separate dosage forms.

In some embodiments, a corticosteroid such as dexamethasone is administered to a patient in combination with the treatment methods of the disclosure where the dexamethasone is administered intermittently as opposed to continuously.

The treatment methods described herein can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The treatment methods described herein can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the treatment methods and regimens of the present disclosure can be used in combination with tumor specific antigen such as heat shock proteins isolated from tumor tissue itself. In some embodiments, the treatment methods described herein can be combined with dendritic cells immunization to activate potent anti-tumor responses.

The treatment methods and regimens of the present disclosure can be used in combination with bispecific macrocyclic peptides that target Fe alpha or Fe gamma receptor-expressing effectors cells to tumor cells. The treatment methods and regimens of the present disclosure can also be combined with macrocyclic peptides that activate host immune responsiveness.

In some further embodiments, the treatment methods of the disclosure are combined with administration of other therapeutic agents to a patient prior to, during, and/or after a bone marrow transplant or stem cell transplant. The treatment methods and regimens of the present disclosure can be used in combination with bone marrow transplant for the treatment of a variety of tumors of hematopoietic origin.

When more than one pharmaceutical agents is administered to a patient, as discussed in any of the above embodiments, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

In some embodiments, compounds described herein can be used in combination with immune checkpoint inhibitors. Exemplary immune checkpoint inhibitors include inhibitors against immune checkpoint molecules such as CD27, CD28, CD40, CD122, CD %, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3 (e.g., INCAGN2385), TIM3 (e.g., INCB2390), VISTA, PD-1, PD-L1 and PD-L2. In some embodiments, the immune checkpoint molecule is a stimulatory checkpoint molecule selected from CD27, CD28, CD40, ICOS, OX40 (e.g., INCAGN1949), GITR (e.g., INCAGN1876) and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is MGA012, nivolumab, pembrolizumab (also known as MK-3475), pidilizumab, SHR-1210, PDR001, ipilumimab or AMP-224. In some embodiments, the anti-PD-1 monoclonal antibody is nivolumab or pembrolizumab. In some embodiments, the anti-PD1 antibody is pembrolizumab. In some embodiments, the anti-PD1 antibody is nivolumab. In some embodiments, the anti-PD-1 monoclonal antibody is MGA012 (retifanlimab). In some embodiments, the anti-PD1 antibody is SHR-1210. Other anti-cancer agent(s) include antibody therapeutics such as 4-1BB (e.g. urelumab, utomilumab.

In some embodiments, the compounds of the disclosure can be used in combination with INCB086550.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the inhibitor of an immune checkpoint molecule is an inhibitor of CD19, e.g., an anti-CD19 antibody. In some embodiments, the anti-CD19 antibody is tafasitamab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196.

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR-1210), sintilimab (IBI308), AB122 (GLS-010), AMP-224, AMP-514/MEDI-0680, BMS936559, JTX-4014, BGB-108, SHR-1210, MEDI4736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217, 149, or 10,308,644; U.S. Publ. Nos. 2017/0145025, 2017/0174671, 2017/0174679, 2017/0320875, 2017/0342060, 2017/0362253, 2018/0016260, 2018/0057486, 2018/0177784, 2018/0177870, 2018/0179179, 2018/0179201, 2018/0179202, 2018/0273519, 2019/0040082, 2019/0062345, 2019/0071439, 2019/0127467, 2019/0144439, 2019/0202824, 2019/0225601, 2019/0300524, or 2019/0345170; or PCT Pub. Nos. WO 03042402, WO 2008156712, WO 2010089411, WO 2010036959, WO 2011066342, WO 2011159877, WO 2011082400, or WO 2011161699, which are each incorporated herein by reference in their entirety. In some embodiments, the inhibitor of PD-L1 is INCB086550.

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MEDI4736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MEDI9447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MEDI1873, or MEDI6469. In some embodiments, the agonist of an immune checkpoint molecule is an agonist of OX40, e.g., OX40 agonist antibody or OX40L fusion protein. In some embodiments, the anti-OX40 antibody is INCAGN01949, MEDI0562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. Inhibitors of arginase inhibitors include INCB1158.

As provided throughout, the additional compounds, inhibitors, agents, etc. can be combined with the present compound in a single or continuous dosage form, or they can be administered simultaneously or sequentially as separate dosage forms.

In some embodiments, the compounds described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with compounds described herein for the treatment of cancer include chemotherapeutic agents, targeted cancer therapies, immunotherapies or radiation therapy. Compounds described herein may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds described herein. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

The compounds described herein may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds described herein include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds described herein. In some embodiments, the JAK inhibitor is selective for JAK1 over JAK2 and JAK3.

Other suitable agents for use in combination with compounds described herein include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with compounds described herein include steroids including 17 alpha-ethinylestradiol, diethylstilbestrol, testosterone, prednisone, fluoxymesterone, methylprednisolone, methyltestosterone, prednisolone, triamcinolone, chlorotrianisene, hydroxyprogesterone, aminoglutethimide, and medroxyprogesteroneacetate.

Other suitable agents for use in combination with compounds described herein include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds described herein may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of the present disclosure can be used in combination with bone marrow transplant for the treatment of a variety of tumors of hematopoietic origin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

As provided throughout, the additional compounds, inhibitors, agents, etc. can be combined with the present compound in a single or continuous dosage form, or they can be administered simultaneously or sequentially as separate dosage forms.

Pharmaceutical Formulations and Dosage Forms

When employed as pharmaceuticals, compounds described herein can be administered in the form of pharmaceutical compositions which refers to a combination of one or more compounds described herein, and at least one pharmaceutically acceptable carrier or excipient. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, one or more compounds described herein in combination with one or more pharmaceutically acceptable carriers or excipients. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is suitable for topical administration.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from, for example, about 5 mg to about 1000 mg, about 5 mg to about 100 mg, about 100 mg to about 500 mg or about 10 to about 30 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid pre-formulation composition containing a homogeneous mixture of one or more compounds described herein. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds, or compositions as described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of the compounds in a pharmaceutical composition can vary depending upon a number of factors including dosage, chemical characteristics (e.g., hydrophobicity), and the route of administration. For example, compounds of the present disclosure can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Compounds described herein can also be formulated in combination with one or more additional active ingredients, which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating FGFR3 protein in tissue samples, including human, and for identifying FGFR3 ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes FGFR binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula (I) can be optionally substituted with deuterium atoms, such as —$CD_3$ being substituted for —$CH_3$). In some embodiments, alkyl groups in Formula (I) can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^3$H, $^{14}$C, $^{82}$Br, $^{125}$I, $^{131}$I or $^{35}$S can be useful. For radio-imaging applications $^{11}$C, $^{18}$F, $^{125}$I, $^{123}$I, $^{124}$I, $^{131}$I, $^{75}$Br, $^{76}$Br or $^{77}$Br can be useful.

It is understood that a "radio-labeled" or "labeled compound" is a compound that has incorporated at least one radionuclide. In some embodiments, the radionuclide is selected from the group consisting of $^3$H, $^{14}$C, $^{125}$I, $^{35}$S and $^{82}$Br.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind an FGFR3 protein by monitoring its concentration variation when contacting with the FGFR3, through tracking of the labeling. For example, a test compound (labeled) can be evaluated for its ability to reduce binding of another compound which is known to bind to a FGFR3 protein (i.e., standard compound). Accordingly, the ability of a test compound to compete with the standard compound for binding to the FGFR3 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of FGFR-associated diseases or disorders, such as cancer and other diseases referred to herein which include one or more containers containing a pharmaceutical composition comprising a therapeutically effective amount of a compound of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of FGFR3 as described below.

EXAMPLES

Experimental procedures for compounds of the invention are provided below. Preparatory LC-MS purifications of some of the compounds prepared were performed on Waters mass-directed fractionation systems. The basic equipment setup, protocols, and control software for the operation of these systems have been described in detail in the literature. See e.g., "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity analysis under the following conditions: Instrument; Agilent 1100 series, LC/MSD, Column: Waters Sunfire™ $C_{18}$ 5 µm, 2.1×50 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 µm, 19×100 mm column, eluting with mobile phase A: 0.15% NH$_4$OH in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Intermediate 1. (9-Bromo-2-(2,6-dichlorophenyl)imidazo[2,1-J][1,6]naphthyridin-3-yl)methanol

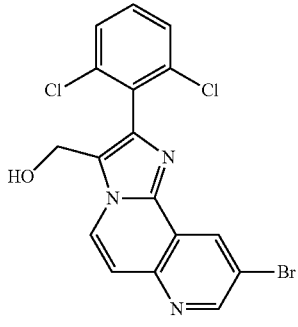 [SMILES: OCc1c(-c2c(Cl)cccc2Cl)nc2c3cc(Br)cnc3ccn12]

Step 1. 3-Bromo-5-chloro-1,6-naphthyridine

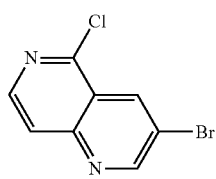

A flask containing a mixture of phosphoryl chloride (41.4 mL, 444 mmol) and 3-bromo-1,6-naphthyridin-5(6H)-one (5.0 g, 22.2 mmol) was stirred at 100° C. for 3 h. The reaction mixture was cooled to room temperature and the reaction mixture was concentrated in vacuo. The resulting residue was cooled down to 0° C. and treated with saturated aqueous NaHCO$_3$ and the mixture was extracted with EtOAc. The organic phase was washed with brine, dried over MgSO$_4$, filtered and the solvent was evaporated in vacuo. The obtained crude product was used in the next step without further purification. LCMS calculated for C$_8$H$_5$BrClN$_2$ (M+H)$^+$: m/z=242.9/244.9; found: 243.0/244.9.

Step 2. 3-Bromo-1,6-naphthyridin-5-amine

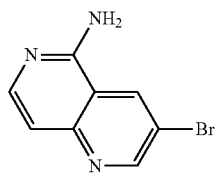 [SMILES: Nc1nccc2ncc(Br)cc12]

A mixture of 3-bromo-5-chloro-1,6-naphthyridine (2.68 g, 11.0 mmol), 1,4-dioxane (9 mL), and ammonium hydroxide solution (9 mL) in a sealed microwave vessel was irradiated at 150° C. for 3 h using a Biotage Initator+ Microwave Synthesizer. The reaction mixture was cooled to room temperature and the solvent was evaporated in vacuo. The obtained crude product was used in the next step without further purification. LCMS calculated for C$_8$H$_7$BrN$_3$ (M+H)$^+$: m/z=224.0/226.0; found: 224.2/226.2.

Step 3. 9-Bromo-2-(2,6-dichlorophenyl)imidazo[2,1-f][1,6]naphthyridine

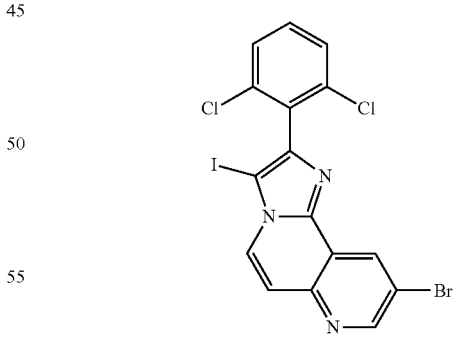

A microwave vessel containing a mixture of 3-bromo-1,6-naphthyridin-5-amine (1.32 g, 5.89 mmol), sodium bicarbonate (742 mg, 8.84 mmol), 2-bromo-1-(2,6-dichlorophenyl)ethan-1-one (1.89 g, 7.07 mmol) and tert-butanol (8 mL) was irradiated at 150° C. for 9 h using a Biotage Initator+ Microwave Synthesizer. After cooling to room temperature, the solid was filtered and washed with CH$_2$Cl$_2$, followed by concentration of the filtrate in vacuo. The resulting residue was purified by Biotage Isolera to give the desired product as an orange solid. LCMS calculated for C$_{16}$H$_9$BrCl$_2$N$_3$(M+H)$^+$: m/z=391.9/393.9/395.9; found 392.1/394.1/396.1.

Step 4. 9-Bromo-2-(2,6-dichlorophenyl)-3-iodoimidazo[2,1-f][1,6]naphthyridine

A vial containing 9-bromo-2-(2,6-dichlorophenyl)imidazo[2,1-f][1,6]naphthyridine (200 mg, 0.509 mmol), NIS (114 mg, 0.509 mmol) in acetonitrile (2 mL) was stirred at 60° C. for 4 h. The solution was subsequently cooled to room temperature, concentrated in vacuo and purified by Biotage Isolera to give the desired product as a brown solid. LCMS calculated for C$_{16}$H$_8$BrCl$_2$IN$_3$ (M+H)$^+$: m/z=517.8/519.8; found 517.9/519.7.

Step 5. 9-Bromo-2-(2,6-dichlorophenyl)-3-vinylimidazo[2,1-f][1,6]naphthyridine

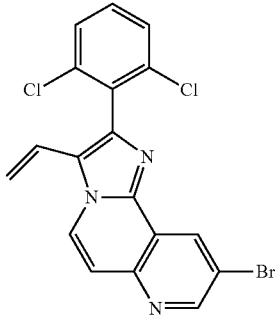 [SMILES: C=Cc1c(-c2c(Cl)cccc2Cl)nc2c3cc(Br)cnc3ccn12]

A mixture of 9-bromo-2-(2,6-dichlorophenyl)-3-iodoimidazo[2,1-f][1,6]naphthyridine (150 mg, 0.289 mmol), potassium phosphate, tribasic (123 mg, 0.578 mmol), tetrakis(triphenylphosphine)palladium(0) (33 mg, 0.029 mmol) and 4,4,5,5-tetramethyl-2-vinyl-1,3,2-dioxaborolane (49 µL, 0.289 mmol) was suspended in 1,4-dioxane (2 mL), and water (200 µL). The reaction mixture was purged with nitrogen for 30 sec and heated to 70° C. for 2 h. Upon cooling to room temperature, the solution was diluted with $CH_2Cl_2$, filtered through Celite and the filtrate was concentrated in vacuo. The resulting residue was purified by Biotage Isolera to give the desired product as a brown solid. LCMS calculated for $C_{18}H_{11}BrCl_2N_3$ $(M+H)^+$: m/z=418.0/419.9; found 418.1/420.1.

Step 6. (9-Bromo-2-(2,6-dichlorophenyl)imidazo[2,1-f][1,6]naphthyridin-3-yl)methanol To a vial was added 9-bromo-2-(2,6-dichlorophenyl)-3-vinylimidazo[2,1-f][1,6]naphthyridine (80 mg, 0.191 mmol), THF (3 mL), water (1 mL) and osmium tetroxide (4 wt. % in $H_2O$, 75 µL, 9.54 µmol), followed by sodium periodate (204 mg, 0.954 mmol). The reaction mixture was stirred at room temperature for 3 h, and upon completion the reaction was quenched with saturated aqueous $Na_2S_2O_3$ and extracted into EtOAc. The combined organic layers were concentrated in vacuo and the residue was dissolved in isopropanol (4 mL), cooled to 0° C., and $NaBH_4$ (7.22 mg, 0.191 mmol) was added with stirring while allowing the reaction to slowly warm to room temperature. The reaction was then cooled to 0° C. and quenched by addition of saturated aqueous $NH_4Cl$. The volatiles were removed in vacuo and the residue was extracted into 20:1 $CH_2Cl_2$/MeOH. The resulting organic layers were combined and concentrated in vacuo. The obtained product was used in the next step without further purification. LCMS calculated for $C_{17}H_{11}BrCl_2N_3O$ $(M+H)^+$: m/z=421.9/423.9; found 421.9/424.0.

Example 1. (2-(2,6-Dichlorophenyl)-9-(1-(pyrimidin-4-ylmethyl)-1H-pyrazol-4-yl)imidazo[2,1-J][1,6]naphthyridin-3-yl)methanol

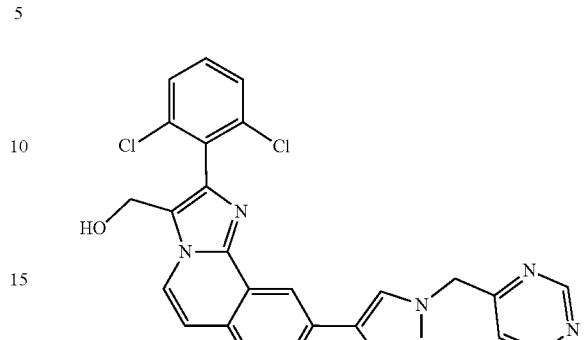

Step 1. (2-(2,6-Dichlorophenyl)-9-(1H-pyrazol-4-yl)imidazo[2,1-f][1,6]naphthyridin-3-yl)methanol A flask containing (9-bromo-2-(2,6-dichlorophenyl)imidazo[2,1-f][1,6]naphthyridin-3-yl)methanol (Intermediate 1, 1.5 g, 3.55 mmol), 4-(4,4,5,5-tetramethyl-1,3,2-dioxaborolan-2-yl)-1-((2-(trimethylsilyl)ethoxy)methyl)-1H-pyrazole (1.26 g, 3.90 mmol), potassium phosphate, tribasic (2.26 g, 10.64 mmol), and (1,1'-bis(diphenylphosphino)ferrocene)dichloropalladium(II) (290 mg, 0.355 mmol) was evacuated and backfilled with nitrogen three times, followed by the addition of 1,4-dioxane (28 mL) and water (7 mL). The vial was sealed and heated to 80° C. for 30 min. After cooling to room temperature, the mixture was filtered through Celite and washed with $CH_2Cl_2$, followed by concentration of the filtrate in vacuo. The obtained crude product was then dissolved in $CH_2Cl_2$ (5 mL) and TFA (5 mL) and left to stir at r.t. for 1 h. The reaction mixture was concentrated in vacuo, then redissolved in MeOH (5 mL) and added to a stirring solution of saturated aqueous $NaHCO_3$ (50 mL). The resulting precipitate was filtered and collected, followed by drying under vacuum. LCMS calculated $C_{20}H_{14}Cl_2N_5O$ $(M+H)^+$: m/z=410.1/412.1; found 410.0/412.1.

Step 2. (2-(2,6-Dichlorophenyl)-9-(1-(pyrimidin-4-ylmethyl)-1H-pyrazol-4-yl)imidazo[2,1-f][1,6]naphthyridin-3-yl)methanol To a vial containing a mixture of (2-(2,6-dichlorophenyl)-9-(1H-pyrazol-4-yl)imidazo[2,1-f][1,6]naphthyridin-3-yl)

methanol (10 mg, 0.024 mmol) and cesium carbonate (24 mg, 0.073 mmol) as a solution in DMF (500 μL) was added 4-(bromomethyl)pyrimidine hydrobromide (9 mg, 0.037 mmol). The vial was sealed and heated to 50° C. for 2 h. After cooling to room temperature, the mixture was then diluted with CH$_3$CN and purified with prep-LCMS (XBridge C18 column, eluting with a gradient of acetonitrile/water containing 0.1% TFA, at flow rate of 60 mL/min) to provide the title compound as the TFA salt. LCMS calculated for C$_{25}$H$_{18}$Cl$_2$N$_7$O (M+H)$^+$: m/z=502.1/504.1; found 502.1/504.1. $^1$H NMR (500 MHz, DMSO-d$_6$) δ 9.29 (d, J=2.3 Hz, 1H), 9.17 (d, J=1.4 Hz, 1H), 8.97 (d, J=2.2 Hz, 1H), 8.79 (d, J=5.2 Hz, 1H), 8.76 (s, 1H), 8.55 (d, J=7.5 Hz, 1H), 8.36 (s, 1H), 7.69-7.60 (m, 2H), 7.55 (dd, J=8.8, 7.4 Hz, 1H), 7.46 (d, J=7.5 Hz, 1H), 7.21 (dd, J=5.2, 1.4 Hz, 1H), 5.56 (s, 2H), 4.68 (s, 2H).

Example 2. 5-((4-(2-(2,6-Dichlorophenyl)-3-(hydroxymethyl)imidazo[2,1-f][1,6]naphthyridin-9-yl)-1H-pyrazol-1-yl)methyl)nicotinonitrile

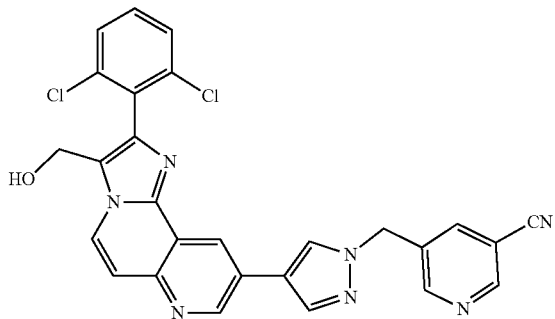 [SMILES: N#Cc1cncc(Cn2cc(-c3cnc4ccn5c(CO)c(-c6c(Cl)cccc6Cl)nc5c4c3)cn2)c1]

This compound was prepared according to the procedures described in Example 1, with 5-(bromomethyl)nicotinonitrile replacing 4-(bromomethyl)pyrimidine hydrobromide in Step 2 to provide the title compound as the TFA salt. LCMS calculated for C$_{27}$H$_{18}$Cl$_2$N$_7$O (M+H)$^+$: m/z=526.1/528.1; found: 526.0/528.0.

Example 3. 5-((4-(2-(2,6-Dichlorophenyl)-3-(hydroxymethyl)imidazo[2,1-f][1,6]naphthyridin-9-yl)-1H-pyrazol-1-yl)methyl)picolinonitrile

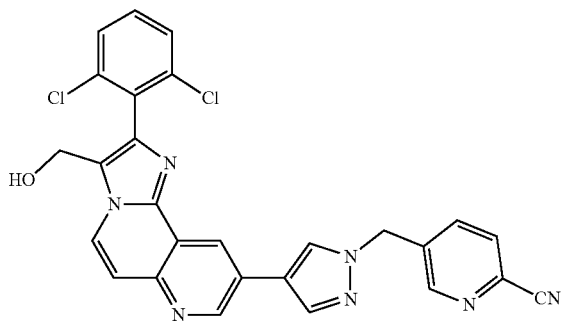 [SMILES: N#Cc1ccc(Cn2cc(-c3cnc4ccn5c(CO)c(-c6c(Cl)cccc6Cl)nc5c4c3)cn2)cn1]

This compound was prepared according to the procedures described in Example 1, with 5-(bromomethyl)picolinonitrile replacing 4-(bromomethyl)pyrimidine hydrobromide in Step 2 to provide the title compound as the TFA salt. LCMS calculated for C$_{27}$H$_{18}$Cl$_2$N$_7$O (M+H)$^+$: m/z=526.1/528.1; found: 526.2/528.2.

Example 4. 4-((4-(2-(2,6-Dichlorophenyl)-3-(hydroxymethyl)imidazo[2,1-f][1,6]naphthyridin-9-yl)-1H-pyrazol-1-yl)methyl)picolinonitrile

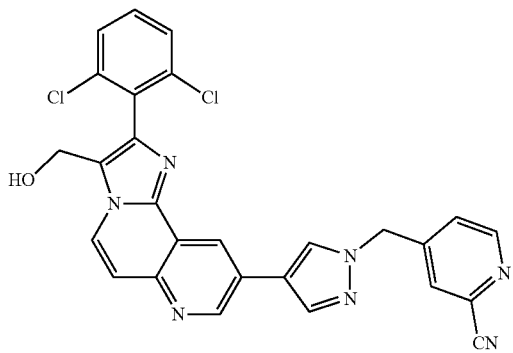 [SMILES: N#Cc1cc(Cn2cc(-c3cnc4ccn5c(CO)c(-c6c(Cl)cccc6Cl)nc5c4c3)cn2)ccn1]

This compound was prepared according to the procedures described in Example 1, with 4-(bromomethyl)picolinonitrile replacing 4-(bromomethyl)pyrimidine hydrobromide in Step 2 to provide the title compound as the TFA salt. LCMS calculated for C$_{27}$H$_{18}$Cl$_2$N$_7$O (M+H)$^+$: m/z=526.1/528.1; found: 526.1/528.1. $^1$H NMR (500 MHz, DMSO-d$_6$) δ 9.28 (d, J=2.2 Hz, 1H), 8.98 (d, J=2.2 Hz, 1H), 8.77-8.72 (m, 2H), 8.56 (d, J=7.5 Hz, 1H), 8.36 (s, 1H), 7.95-7.91 (m, 1H), 7.66-7.62 (m, 2H), 7.58-7.52 (m, 2H), 7.47 (d, J=7.5 Hz, 1H), 5.57 (s, 2H), 4.68 (s, 2H).

Example 5. (2-(2,6-Dichlorophenyl)-9-(1-((2-(trifluoromethyl)pyridin-4-yl)methyl)-1H-pyrazol-4-yl)imidazo[2,1-f][1,6]naphthyridin-3-yl)methanol

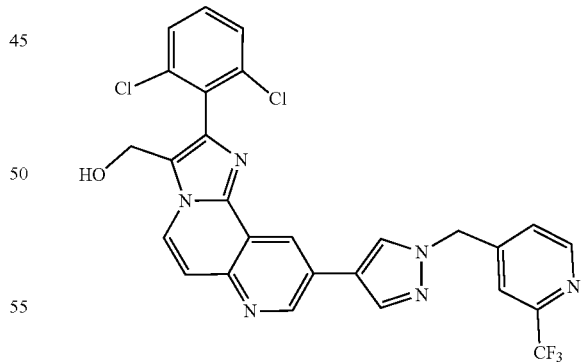

This compound was prepared according to the procedures described in Example 1, with 4-(bromomethyl)-2-(trifluoromethyl)pyridine replacing 4-(bromomethyl)pyrimidine hydrobromide in Step 2 to provide the title compound as the TFA salt. LCMS calculated for C$_{27}$H$_{18}$Cl$_2$F$_3$N$_6$O (M+H)$^+$: m/z=569.1/571.1; found: 569.0/571.0.

Example 6. (4-(2-(2,6-Dichlorophenyl)-3-(hydroxymethyl)imidazo[2,1-f][1,6]naphthyridin-9-yl)phenyl)(morpholino)methanone

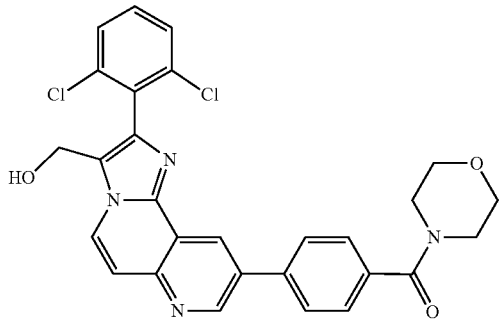 [SMILES: O=C(c1ccc(-c2cnc3ccn4c(CO)c(-c5c(Cl)cccc5Cl)nc4c3c2)cc1)N1CCOCC1]

A vial containing (9-bromo-2-(2,6-dichlorophenyl)imidazo[2,1-f][1,6]naphthyridin-3-yl)methanol (Intermediate 1, 15 mg, 0.035 mmol), (4-(morpholine-4-carbonyl)phenyl)boronic acid (17 mg, 0.071 mmol), potassium phosphate, tribasic (23 mg, 0.11 mmol), and (1,1'-bis(diphenylphosphino)ferrocene)dichloropalladium(II) (4 mg, 5.3 µmol) was evacuated and backfilled with nitrogen three times, followed by the addition of 1,4-dioxane (1 mL) and water (250 µL). The vial was sealed and heated to 80° C. for 30 minutes. After cooling to room temperature, the mixture was then diluted with CH$_3$CN and purified with prep-LCMS (XBridge C18 column, eluting with a gradient of acetonitrile/water containing 0.1% TFA, at flow rate of 60 mL/min) to provide the title compound as the TFA salt. LCMS calculated for C$_{28}$H$_{23}$Cl$_2$N$_4$O$_3$ (M+H)$^+$: m/z=533.1/535.1; found 533.1/535.1.

Example 7. ((1S,4S)-2-Oxa-5-azabicyclo[2.2.1]heptan-5-yl)(4-(2-(2,6-dichlorophenyl)-3-(hydroxymethyl)imidazo[2,1-f][1,6]naphthyridin-9-yl)phenyl)methanone

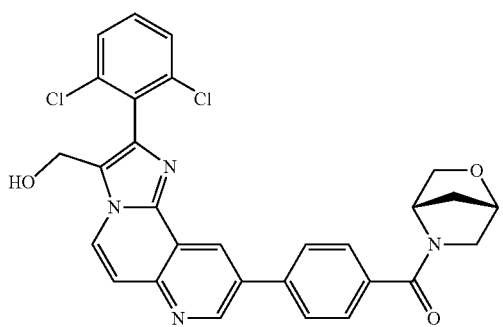 [SMILES: O=C(c1ccc(-c2cnc3ccn4c(CO)c(-c5c(Cl)cccc5Cl)nc4c3c2)cc1)N1C[C@@H]2C[C@H]1CO2]

Step 1. 4-(2-(2,6-Dichlorophenyl)-3-(hydroxymethyl)imidazo[2,1-f][1,6]naphthyridin-9-yl)benzoic acid

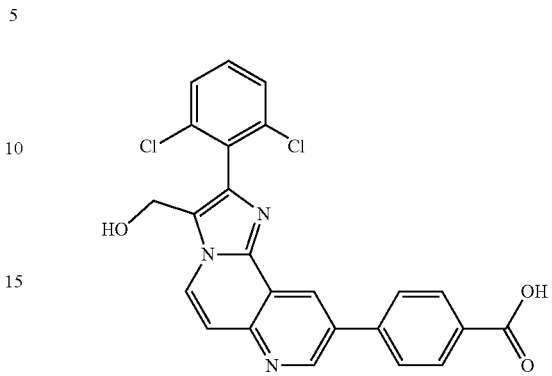

A vial containing (9-bromo-2-(2,6-dichlorophenyl)imidazo[2,1-f][1,6]naphthyridin-3-yl)methanol (Intermediate 1, 100 mg, 0.236 mmol), (4-(tert-butoxycarbonyl)phenyl)boronic acid (79 mg, 0.355 mmol), potassium phosphate, tribasic (151 mg, 0.709 mmol), and (1,1'-bis(diphenylphosphino)ferrocene)dichloropalladium(II) (29 mg, 0.035 mmol) was evacuated and backfilled with nitrogen three times, followed by the addition of 1,4-dioxane (1 mL) and water (250 µL). The vial was sealed and heated to 80° C. for 30 minutes. After cooling to room temperature, the mixture was filtered through Celite and washed with CH$_2$Cl$_2$, followed by concentration of the filtrate in vacuo. The resulting residue was purified by Biotage Isolera to give the desired product as a white solid. The purified product was then dissolved in CH$_2$Cl$_2$ (2 mL) and TFA (1 mL) and left to stir at r.t. for 1 h. The reaction mixture was concentrated in vacuo, then dissolved in MeOH (1 mL) and added to a stirring solution of saturated aqueous NaHCO$_3$ (10 mL). The resulting precipitate was filtered and collected, followed by drying under vacuum. LCMS calculated C$_{24}$H$_{16}$Cl$_2$N$_3$O$_3$ (M+H)$^+$: m/z=464.1/466.1; found 464.0/466.0.

Step 2. ((1S,4S)-2-Oxa-5-azabicyclo[2.2.1]heptan-5-yl)(4-(2-(2,6-dichlorophenyl)-3-(hydroxymethyl)imidazo[2,1-f][1,6]naphthyridin-9-yl)phenyl)methanone To a vial containing 4-(2-(2,6-dichlorophenyl)-3-(hydroxymethyl)imidazo[2,1-f][1,6]naphthyridin-9-yl)benzoic acid (10 mg, 0.022 mmol), (1S,4S)-2-oxa-5-azabicyclo[2.2.1]heptane hydrochloride (4.4 mg, 0.032 mmol), DMF (500 µL) and DIPEA (11 µL, 0.061 mmol) was added HATU (12 mg, 0.032 mmol). The reaction mixture was left to stir at r.t. for 1 h, upon which time water was added and the resulting solid was collected by filtration and washed with water. The solid was then dissolved with TFA and purified with prep-LCMS (XBridge C18 column, eluting with a gradient of acetonitrile/water containing 0.1% TFA, at flow rate of 60 mL/min) to provide the title compound as the TFA salt. LCMS calculated for C$_{29}$H$_{23}$Cl$_2$N$_4$O$_3$ (M+H)$^+$: m/z=545.1/547.1; found 545.1/547.3.

Example 8. 1-(4-(4-(2-(2,6-Dichlorophenyl)-3-(hydroxymethyl)imidazo[2,1-f][1,6]naphthyridin-9-yl)benzyl)piperazin-1-yl)-2-hydroxyethan-1-one

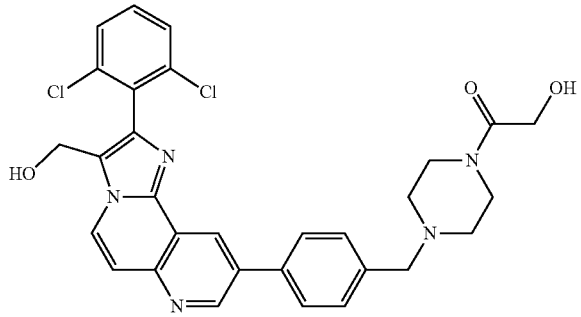 [SMILES: O=C(CO)N1CCN(Cc2ccc(-c3cnc4ccn5c(CO)c(-c6c(Cl)cccc6Cl)nc5c4c3)cc2)CC1]

Step 1. (2-(2,6-Dichlorophenyl)-9-(4-(piperazin-1-ylmethyl)phenyl)imidazo[2,1-f][1.6]naphthyridin-3-yl)methanol

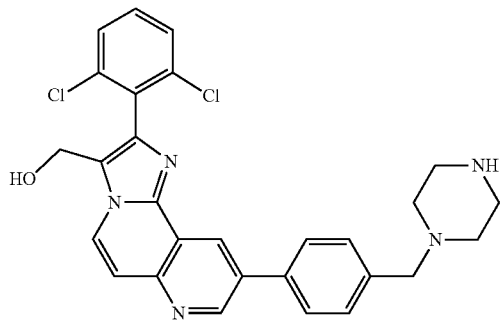 [SMILES: OCc1c(-c2c(Cl)cccc2Cl)nc2c3cc(-c4ccc(CN5CCNCC5)cc4)cnc3ccn12]

A vial containing (9-bromo-2-(2,6-dichlorophenyl)imidazo[2,1-f][1,6]naphthyridin-3-yl)methanol (Intermediate 1, 100 mg, 0.236 mmol), tert-butyl 4-(4-(4,4,5,5-tetramethyl-1,3,2-dioxaborolan-2-yl)benzyl)piperazine-1-carboxylate (105 mg, 0.260 mmol), potassium phosphate, tribasic (151 mg, 0.709 mmol), and (1,1'-bis(diphenylphosphino)ferrocene)dichloropalladium(II) (19 mg, 0.024 mmol) was evacuated and backfilled with nitrogen three times, followed by the addition of 1,4-dioxane (2 mL) and water (500 μL). The vial was sealed and heated to 80° C. for 30 minutes. After cooling to room temperature, the mixture was filtered through Celite and washed with $CH_2Cl_2$, followed by concentration of the filtrate in vacuo. The resulting residue was purified by Biotage Isolera to give the desired product as a yellow solid. The purified product was then dissolved in $CH_2Cl_2$ (5 mL) and TFA (1 mL) and left to stir at r.t. for 1 h. The reaction mixture was concentrated in vacuo, then dissolved in MeOH (1 mL) and added to a stirring solution of saturated aqueous $NaHCO_3$ (10 mL). The resulting precipitate was filtered and collected, followed by drying under vacuum. LCMS calculated $C_{28}H_{26}Cl_2N_5O$ $(M+H)^+$: m/z=518.2/520.1; found 518.2/520.2.

Step 2. 1-(4-(4-(2-(2,6-Dichlorophenyl)-3-(hydroxymethyl)imidazo[2,1-f][1,6]naphthyridin-9-yl)benzyl)piperazin-1-yl)-2-hydroxyethan-1-one To a vial containing (2-(2,6-dichlorophenyl)-9-(4-(piperazin-1-ylmethyl)phenyl)imidazo[2,1-f][1,6]naphthyridin-3-yl)methanol (10 mg, 0.019 mmol), 2-hydroxyacetic acid (2 mg, 0.029 mmol), DMF (500 μL) and DIPEA (7 μL, 0.039 mmol) was added HATU (11 mg, 0.029 mmol). The reaction mixture was left to stir at r.t. for 1 h, upon which time water was added and the resulting solid was collected by filtration and washed with water. The solid was then dissolved with TFA and purified with prep-LCMS (XBridge C18 column, eluting with a gradient of acetonitrile/water containing 0.1% TFA, at flow rate of 60 mL/min) to provide the title compound as the TFA salt. LCMS calculated for $C_{30}H_{28}Cl_2N_5O_3$ $(M+H)^+$: m/z=576.2/578.2; found 576.2/578.2.

Example 9. 1-(4-(4-(2-(2,6-Dichlorophenyl)-3-(hydroxymethyl)imidazo[2,1-f][1,6]naphthyridin-9-yl)benzyl)piperazin-1-yl)ethan-1-one

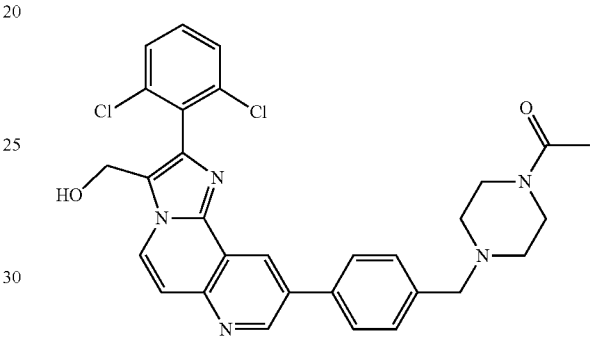

This compound was prepared according to the procedures described in Example 8, with acetic acid replacing 2-hydroxyacetic acid in Step 2 to provide the title compound as the TFA salt. LCMS calculated for $C_{30}H_{28}Cl_2N_5O_2$ $(M+H)^+$: m/z=560.2/562.2; found: 560.3/562.3.

Example 10. 1-(4-(4-(2-(2,6-Dichlorophenyl)-3-(hydroxymethyl)imidazo[2,1-f][1,6]naphthyridin-9-yl)phenyl)piperazin-1-yl)-2-hydroxyethan-1-one

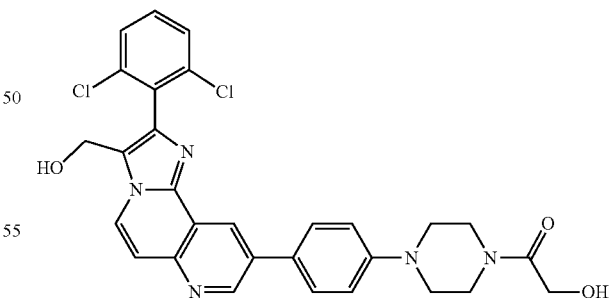

This compound was prepared according to the procedures described in Example 8, with tert-butyl 4-(4-(4,4,5,5-tetramethyl-1,3,2-dioxaborolan-2-yl)phenyl)piperazine-1-carboxylate replacing tert-butyl 4-(4-(4,4,5,5-tetramethyl-1,3,2-dioxaborolan-2-yl)benzyl)piperazine-1-carboxylate in Step 1 to provide the title compound as the TFA salt. LCMS calculated for $C_{29}H_{26}Cl_2N_5O_3$ $(M+H)^+$: m/z=562.1/564.1; found: 562.2/564.1.

Example 11. (2-(2-Chloro-6-methylphenyl)-9-(1-(1-methylpiperidin-4-yl)-1H-pyrazol-4-yl)imidazo[2,1-J][1,6]naphthyridin-3-yl)methanol

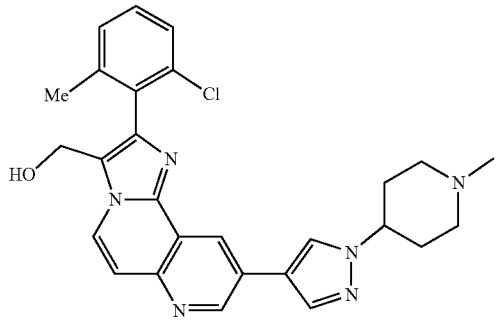 [SMILES: Cc1cccc(Cl)c1-c1nc2c3cc(-c4cnn(C5CCN(C)CC5)c4)cnc3ccn2c1CO]

Step 1. (2-(2,6-Dichlorophenyl)-9-(1-(1-methylpiperidin-4-yl)-1H-pyrazol-4-yl)imidazo[2,1-f][1,6]naphthyridin-3-yl)methanol

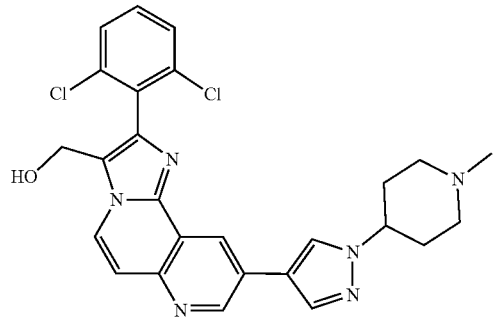 [SMILES: CN1CCC(n2cc(-c3cnc4ccn5c(CO)c(-c6c(Cl)cccc6Cl)nc5c4c3)cn2)CC1]

A vial containing (9-bromo-2-(2,6-dichlorophenyl)imidazo[2,1-f][1,6]naphthyridin-3-yl)methanol (Intermediate 1, 50 mg, 0.118 mmol), 1-methyl-4-(4-(4,4,5,5-tetramethyl-1,3,2-dioxaborolan-2-yl)-1H-pyrazol-1-yl)piperidine (105 mg, 0.260 mmol), potassium phosphate, tribasic (75 mg, 0.355 mmol), and (1,1'-bis(diphenylphosphino)ferrocene)dichloropalladium(II) (15 mg, 0.018 mmol) was evacuated and backfilled with nitrogen three times, followed by the addition of 1,4-dioxane (1 mL) and water (250 µL). The vial was sealed and heated to 80° C. for 30 minutes. After cooling to room temperature, the mixture was filtered through Celite and washed with CH$_2$Cl$_2$, followed by concentration of the filtrate in vacuo. The resulting residue was purified by Biotage Isolera to give the desired product as a yellow solid. LCMS calculated C$_{26}$H$_{25}$Cl$_2$N$_6$O (M+H)$^+$: m/z=507.1/509.1; found 507.1/509.1.

Step 2. (2-(2-Chloro-6-methylphenyl)-9-(1-(1-methylpiperidin-4-yl)-1H-pyrazol-4-yl)imidazo[2,1-f][1,6]naphthyridin-3-yl)methanol A microwave vial containing a mixture of (2-(2,6-dichlorophenyl)-9-(1-(1-methylpiperidin-4-yl)-1H-pyrazol-4-yl)imidazo[2,1-f][1,6]naphthyridin-3-yl)methanol (84 mg, 0.166 mmol), Pd$_2$(dba)$_3$ (15 mg, 0.017 mmol), 9,9-dimethyl-4,5-bis(diphenylphosphino)xanthene (29 mg, 0.050 mmol), and potassium carbonate (46 mg, 0.331 mmol) was evacuated and backfilled with nitrogen three times, followed by the addition of 1,4-dioxane (12 mL) and trimethylboroxine (26 µL, 0.182 mmol). The vial was irradiated at 130° C. for 2 h using a Biotage Initator+ Microwave Synthesizer. After cooling to room temperature, the mixture was filtered through Celite and washed with CH$_2$Cl$_2$, followed by concentration of the filtrate in vacuo. The residue was then dissolved with CH$_3$CN and purified with prep-LCMS (XBridge C18 column, eluting with a gradient of acetonitrile/water containing 0.1% TFA, at flow rate of 60 mL/min) to provide the title compound as the TFA salt. LCMS calculated for C$_{27}$H$_{28}$ClN$_6$O (M+H)$^+$: m/z=487.2; found 487.2.

Example 12. 5-((4-(2-(2,6-Dichlorophenyl)-3-(hydroxymethyl)imidazo[2,1-f][1,6]naphthyridin-9-yl)-1H-pyrazol-1-yl)methyl)-N,N-dimethylpicolinamide

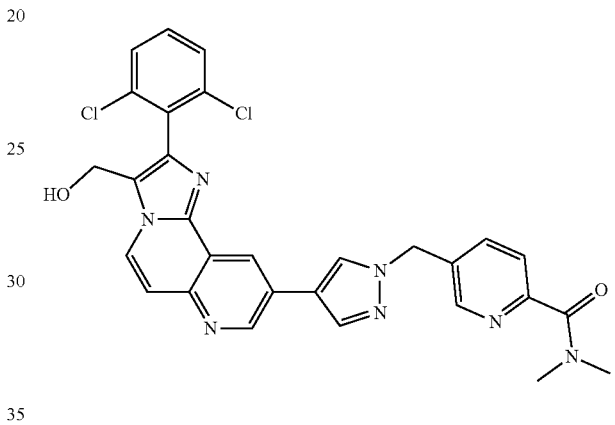

Step 1. 5-((4-(2-(2,6-Dichlorophenyl)-3-(hydroxymethyl)imidazo[2,1-f][1,6]naphthyridin-9-yl)-1H-pyrazol-1-yl)methyl)picolinic acid

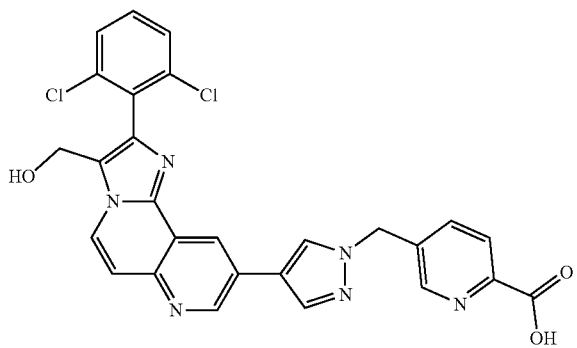 [SMILES: O=C(O)c1ccc(Cn2cc(-c3cnc4ccn5c(CO)c(-c6c(Cl)cccc6Cl)nc5c4c3)cn2)cn1]

To a vial containing a mixture of (2-(2,6-dichlorophenyl)-9-(1H-pyrazol-4-yl)imidazo[2,1-f][1,6]naphthyridin-3-yl)methanol (100 mg, 0.244 mmol) and cesium carbonate (159 mg, 0.487 mmol) as a solution in DMF (1 mL) was added methyl 5-(bromomethyl)picolinate (84 mg, 0.366 mmol). The reaction mixture was left to stir at r.t. for 1 h, upon which time water was added and the resulting solid was collected by filtration. The crude solid was dissolved in THF (2 mL) and 2M aq. LiOH (500 µL, 1.0 mmol) and left to stir at r.t. for 1 h, after which time the pH was adjusted to ~7 by addition of 1M aq. HCl. The resulting solid was collected by filtration and washed with water, then left to dry under vacuum. The obtained crude product was used in the next step without further purification. LCMS calculated for $C_{27}H_{19}Cl_2N_6O_3$ (M+H)$^+$: m/z=545.1/547.1; found: 545.1/547.1.

Step 2. 5-((4-(2-(2,6-Dichlorophenyl)-3-(hydroxymethyl)imidazo[2,1-f][1,6]naphthyridin-9-yl)-1H-pyrazol-1-yl)methyl)-N,N-dimethylpicolinamide To a vial containing 5-((4-(2-(2,6-dichlorophenyl)-3-(hydroxymethyl)imidazo[2,1-f][1,6]naphthyridin-9-yl)-1H-pyrazol-1-yl)methyl)picolinic acid (10 mg, 0.018 mmol), dimethylamine (2M in EtOH, 14 μL, 0.028 mmol), DMF (0.5 mL) and DIPEA (6 μL, 0.037 mmol) was added HATU (10 mg, 0.028 mmol). The reaction mixture was left to stir at r.t. for 1 h, upon which time water was added and the resulting solid was collected by filtration and washed with water. The solid was then dissolved with TFA and purified with prep-LCMS (XBridge C18 column, eluting with a gradient of acetonitrile/water containing 0.1% TFA, at flow rate of 60 mL/min) to provide the title compound as the TFA salt. LCMS calculated for $C_{29}H_{24}Cl_2N_7O_2$ (M+H)$^+$: m/z=572.1/574.1; found 572.2/574.2.

Example 13. (3-(4-(2-(2,6-Dichlorophenyl)-3-methylimidazo[2,1-J][1,6]naphthyridin-9-yl)-1H-pyrazol-1-yl)azetidin-1-yl)(1-methyl-1H-1,2,3-triazol-4-yl)methanone

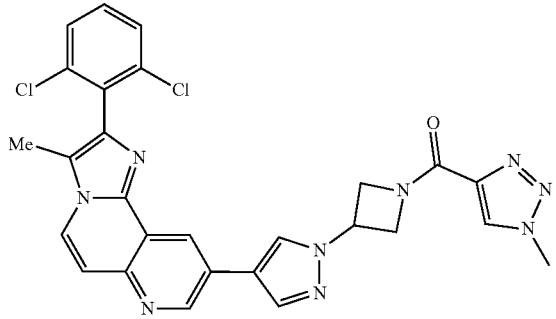 [SMILES: Cc1c(-c2c(Cl)cccc2Cl)nc2c3cc(-c4cnn(C5CN(C(=O)c6cn(C)nn6)C5)c4)cnc3ccn12]

Step 1. 2-(2,6-Dichlorophenyl)-9-(1-((2-(trimethylsilyl)ethoxy)methyl)-1H-pyrazol-4-yl)imidazo[2,1-f][1,6]naphthyridine

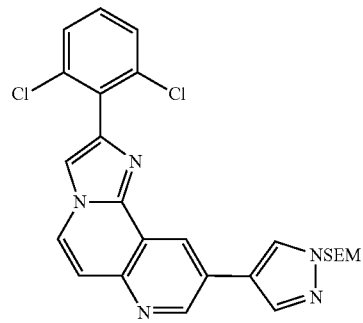 [SMILES: C[Si](C)(C)CCOCn1cc(-c2cnc3ccn4cc(-c5c(Cl)cccc5Cl)nc4c3c2)cn1]

A vial containing a mixture of 9-bromo-2-(2,6-dichlorophenyl)imidazo[2,1-f][1,6]naphthyridine (Intermediate 1, Step 3, 1.0 g, 2.54 mmol), 4-(4,4,5,5-tetramethyl-1,3,2-dioxaborolan-2-yl)-1-((2-(trimethylsilyl)ethoxy)methyl)-1H-pyrazole (866 mg, 2.67 mmol), (1,1'-bis(diphenylphosphino)ferrocene)-dichloropalladium(II) (208 mg, 0.254 mmol), and potassium phosphate, tribasic (1.62 g, 7.63 mmol) was evacuated and backfilled with nitrogen three times, followed by the addition of 1,4-dioxane (13.5 mL) and water (3.5 mL). The vial was sealed and heated to 80° C. for 30 min. After cooling to room temperature, the mixture was filtered through Celite and washed with $CH_2Cl_2$, followed by concentration of the filtrate in vacuo. The obtained crude residue was purified by Biotage Isolera to give the desired product. LCMS calculated for $C_{25}H_{26}Cl_2N_5OSi$ (M+H)$^+$: m/z=510.1/512.1; found 510.1/512.1.

Step 2. 3-Bromo-2-(2,6-dichlorophenyl)-9-(1-((2-(trimethylsilyl)ethoxy)methyl)-1H-pyrazol-4-yl)imidazo[2,1-f][1,6]naphthyridine

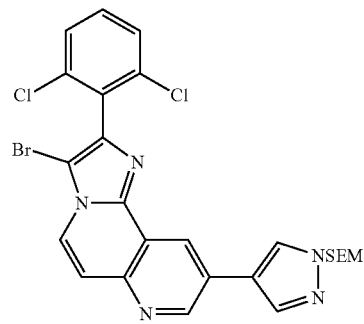 [SMILES: C[Si](C)(C)CCOCn1cc(-c2cnc3ccn4c(Br)c(-c5c(Cl)cccc5Cl)nc4c3c2)cn1]

To a flask containing 2-(2,6-dichlorophenyl)-9-(1-((2-(trimethylsilyl)ethoxy)methyl)-1H-pyrazol-4-yl)imidazo[2,1-f][1,6]naphthyridine (1.30 g, 2.54 mmol) as a solution in $CH_2Cl_2$ (25 mL) was added NBS (542 mg, 3.05 mmol) and left to stir at r.t. for 10 min. The volatiles were removed under reduced pressure and the obtained crude product was purified by Biotage Isolera to give the desired product. LCMS calculated for $C_{25}H_{25}BrCl_2N_5OSi$ (M+H)$^+$: m/z=588.0/590.0/592.0; found: 588.2/590.2/592.2.

Step 3. 2-(2,6-Dichlorophenyl)-3-methyl-9-(1H-pyrazol-4-yl)imidazo[2,1-f][1,6]naphthyridine

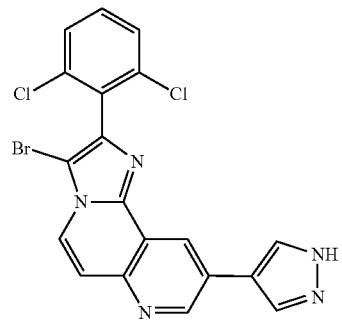 [SMILES: Clc1cccc(Cl)c1-c1nc2c3cc(-c4cn[nH]c4)cnc3ccn2c1Br]

A vial containing a mixture of 3-bromo-9-(1-((2-(trimethylsilyl)ethoxy)methyl)-1H-pyrazol-4-yl)imidazo[2,1-f][1,6]naphthyridine (1.97 g, 4.43 mmol), tetrakis(triphenylphosphine)palladium(0) (294 mg, 0.254 mmol), and sodium carbonate (808 mg, 7.62 mmol) was evacuated and backfilled with nitrogen three times, followed by the addition of 1,4-dioxane (13 mL), water (3.5 mL), and trimethylboroxine (426 μL, 3.05 mmol). The vial was sealed and heated to 100° C. overnight. After cooling to room temperature, the mixture was filtered through Celite and washed with $CH_2Cl_2$, followed by concentration of the filtrate in vacuo. The obtained crude product was purified by Biotage Isolera to give the desired product. The purified material was then dissolved in $CH_2Cl_2$ (10 mL) and TFA (2 mL) and left to stir at r.t. for 2 h. The reaction mixture was concentrated in vacuo, then dissolved in MeOH (2 mL) and added to a stirring solution of saturated aqueous $NaHCO_3$ (50 mL). The resulting solid precipitate was filtered and collected, followed by drying under vacuum overnight. LCMS calculated for $C_{20}H_{14}Cl_2N_5$ $(M+H)^+$: m/z=394.1/396.1; found 394.0/396.0.

Step 4. 9-(1-(Azetidin-3-yl)-1H-pyrazol-4-yl)-2-(2,6-dichlorophenyl)-3-methylimidazo[2,1-f][1,6]naphthyridine

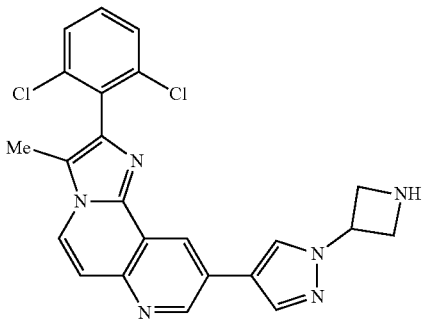 [SMILES: Cc1c(-c2c(Cl)cccc2Cl)nc2c3cc(-c4cnn(C5CNC5)c4)cnc3ccn12]

To a vial containing a mixture of 2-(2,6-dichlorophenyl)-3-methyl-9-(1H-pyrazol-4-yl)imidazo[2,1-f][1,6]naphthyridine (250 mg, 0.634 mmol), tert-butyl 3-((methylsulfonyl)oxy)azetidine-1-carboxylate (319 mg, 1.27 mmol), cesium carbonate (620 mg, 1.90 mmol) was added acetonitrile (6.3 mL). The vial was sealed and heated to 80° C. for 16 h. After cooling to room temperature, the mixture was filtered through Celite and washed with acetonitrile, followed by concentration of the filtrate in vacuo. The resulting residue was purified by Biotage Isolera to give the desired product as a tan solid. The purified material was then dissolved in $CH_2Cl_2$ (3 mL) and TFA (1 mL) and left to stir at r.t. for 1 h. The reaction mixture was concentrated in vacuo, then dissolved in MeOH (3 mL) and added to a stirring solution of saturated aqueous $NaHCO_3$ (15 mL). The resulting solid precipitate was filtered and collected, followed by drying under vacuum overnight. LCMS calculated for $C_{23}H_{19}Cl_2N_6$ $(M+H)^+$: m/z=449.1/451.1; found: 449.1/451.1.

Step 5. (3-(4-(2-(2,6-Dichlorophenyl)-3-methylimidazo[2,1-f][1,6]naphthyridin-9-yl)-1H-pyrazol-1-yl)azetidin-1-yl)(1-methyl-1H-1,2,3-triazol-4-yl)methanone To a vial containing 9-(1-(azetidin-3-yl)-1H-pyrazol-4-yl)-2-(2,6-dichlorophenyl)-3-methylimidazo[2,1-f][1,6]naphthyridine (230 mg, 0.512 mmol) as a solution in DMF (2 mL) was added 1-methyl-1H-1,2,3-triazole-4-carboxylic acid (98 mg, 0.768 mmol), diisopropylethylamine (358 μL, 2.05 mmol), and BOP (340 mg, 0.768 mmol). The reaction mixture was left to stir at r.t. for 1 h. Water was then added and the resulting solid was collected by filtration and washed with water. The solid was then dissolved with TFA and purified with prep-LCMS (XBridge C18 column, eluting with a gradient of acetonitrile/water containing 0.1% TFA, at flow rate of 60 mL/min) to provide the title compound as the TFA salt. LCMS calculated for $C_{27}H_{22}Cl_2N_9O$ $(M+H)^+$: m/z=558.1/560.1; found 558.1/560.1. $^1H$ NMR (500 MHz, DMSO-$d_6$) δ 9.30 (d, J=2.2 Hz, 1H), 8.99 (d, J=2.2 Hz, 1H), 8.88 (d, J=0.7 Hz, 1H), 8.60 (s, 1H), 8.49 (d, J=7.5 Hz, 1H), 8.38 (d, J=0.7 Hz, 1H), 7.69-7.64 (m, 2H), 7.57 (dd, J=8.7, 7.5 Hz, 1H), 7.46 (d, J=7.5 Hz, 1H), 5.42 (tt, J=8.0, 5.2 Hz, 1H), 5.09 (ddd, J=10.4, 7.9, 1.2 Hz, 1H), 4.87 (dd, J=10.4, 5.2 Hz, 1H), 4.59 (ddd, J=10.5, 8.1, 1.2 Hz, 1H), 4.38 (dd, J=10.5, 5.2 Hz, 1H), 4.10 (s, 3H), 2.41 (s, 3H).

Example 14. (3-(4-(2-(2,6-Dichlorophenyl)-3-methylimidazo[2,1-J][1,6]naphthyridin-9-yl)-1H-pyrazol-1-yl)azetidin-1-yl)(2-methyl-2H-tetrazol-5-yl)methanone

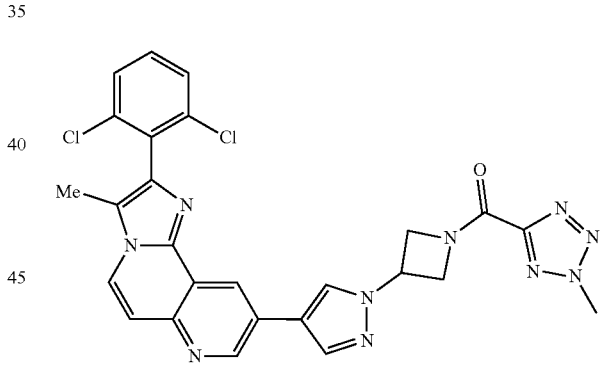

This compound was prepared according to the procedures described in Example 13, with 2-methyl-2H-tetrazole-5-carboxylic acid replacing 1-methyl-1H-1,2,3-triazole-4-carboxylic acid in Step 5 to provide the title compound as the TFA salt. LCMS calculated for $C_{26}H_{21}Cl_2N_{10}O$ $(M+H)^+$: m/z=559.1/561.1; found: 559.2/561.2. $^1H$ NMR (500 MHz, DMSO-$d_6$) δ 9.28 (d, J=2.3 Hz, 1H), 8.98 (d, J=2.2 Hz, 1H), 8.90 (s, 1H), 8.47 (d, J=7.5 Hz, 1H), 8.39 (s, 1H), 7.66 (d, J=8.1 Hz, 2H), 7.56 (dd, J=8.7, 7.5 Hz, 1H), 7.43 (d, J=7.5 Hz, 1H), 5.43 (tt, J=8.0, 5.2 Hz, 1H), 5.10-5.03 (m, 1H), 4.86 (ddd, J=10.5, 5.1, 1.3 Hz, 1H), 4.67 (ddd, J=10.8, 8.1, 1.4 Hz, 1H), 4.47-4.41 (m, 4H), 2.40 (s, 3H).

Example 15. (2-(2,6-Dichlorophenyl)-9-(1-ethyl-1H-pyrazol-4-yl)imidazo[2,1-f][1,6]naphthyridin-3-yl)methanol

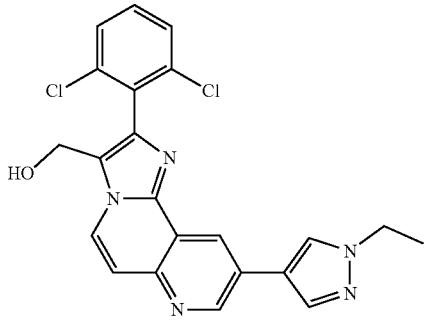 [SMILES: CCn1cc(-c2cnc3ccn4c(CO)c(-c5c(Cl)cccc5Cl)nc4c3c2)cn1]

A vial containing (9-bromo-2-(2,6-dichlorophenyl)imidazo[2,1-f][1,6]naphthyridin-3-yl)methanol (Intermediate 1, 15 mg, 0.035 mmol), (1-ethyl-1H-pyrazol-4-yl)boronic acid (5 mg, 0.035 mmol), potassium phosphate, tribasic (23 mg, 0.106 mmol), and (1,1'-bis(diphenylphosphino)ferrocene)dichloropalladium(II) (2.6 mg, 3.55 µmol) was evacuated and backfilled with nitrogen three times, followed by the addition of 1,4-dioxane (1 mL) and water (100 µL). The vial was sealed and heated to 80° C. for 30 minutes. Upon completion the reaction mixture was flushed through a SiliaPrep SPE thiol cartridge (SPE-R51030B-06P), diluted with acetonitrile/methanol and purified with prep-LCMS (XBridge C18 column, eluting with a gradient of acetonitrile/water containing 0.1% TFA, at flow rate of 60 mL/min) to provide the title compound as the TFA salt. LCMS calculated for $C_{22}H_{18}Cl_2N_5O$ (M+H)$^+$: m/z=438.1/440.1; found 438.1/440.1.

Example 16. 2-(4-(2-(2,6-Dichlorophenyl)-3-(hydroxymethyl)imidazo[2,1-f][1,6]naphthyridin-9-yl)-1H-pyrazol-1-yl)-2-methylpropanenitrile

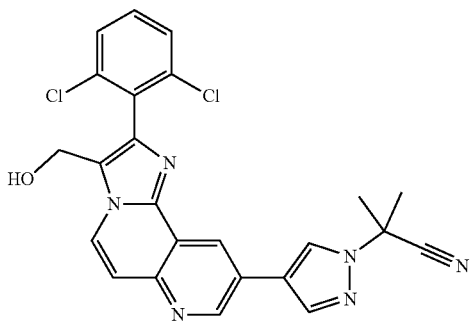 [SMILES: CC(C)(C#N)n1cc(-c2cnc3ccn4c(CO)c(-c5c(Cl)cccc5Cl)nc4c3c2)cn1]

This compound was prepared according to the procedures described in Example 15, with 2-methyl-2-(4-(4,4,5,5-tetramethyl-1,3,2-dioxaborolan-2-yl)-1H-pyrazol-1-yl)propanenitrile replacing (1-ethyl-1H-pyrazol-4-yl)boronic acid to provide the title compound as the TFA salt. LCMS calculated for $C_{24}H_{19}Cl_2N_6O$ (M+H)$^+$: m/z=477.1/479.1; found: 477.1/479.1.

Example 17. 2-(4-(2-(2,6-Dichlorophenyl)-3-(hydroxymethyl)imidazo[2,1-f][1,6]naphthyridin-9-yl)-1H-pyrazol-1-yl)propanenitrile

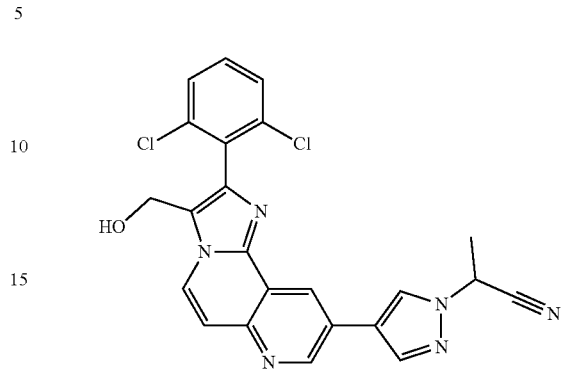

This compound was prepared according to the procedures described in Example 15, with 2-(4-(4,4,5,5-tetramethyl-1,3,2-dioxaborolan-2-yl)-1H-pyrazol-1-yl)propanenitrile replacing (1-ethyl-1H-pyrazol-4-yl)boronic acid. LCMS calculated for $C_{23}H_{17}Cl_2N_6O$ (M+H)$^+$: m/z=463.1/465.1; found: 463.2/465.2. This racemate was separated into pure enantiomers by subjecting to chiral SFC (Phenomenex Lux Sum Cellulose-21.1×250 mm column, eluting with an isocratic solution of 35% MeOH in $CO_2$, at a flow rate of 65 mL/min, $t_{R,\ peak\ 1}$=2.8 min, $t_{R,\ peak\ 2}$=3.9 min). After the solvent was evaporated in vacuo, each enantiomer was purified by prep-LCMS (XBridge C18 column, eluting with a gradient of acetonitrile/water containing 0.1% TFA, at flow rate of 60 mL/min) to provide each enantiomer of the title compound as the TFA salt. $^1$H NMR (600 MHz, DMSO-d$_6$) δ 9.30 (d, J=2.3 Hz, 1H), 9.02 (dd, J=2.3, 0.7 Hz, 1H), 8.83 (d, J=0.8 Hz, 1H), 8.57 (d, J=7.5 Hz, 1H), 8.44 (d, J=0.8 Hz, 1H), 7.72-7.60 (m, 2H), 7.56 (dd, J=8.7, 7.6 Hz, 1H), 7.48 (dd, J=7.5, 0.7 Hz, 1H), 5.91 (q, J=7.1 Hz, 1H), 4.69 (s, 2H), 1.88 (d, J=7.1 Hz, 3H).

Example 18. 1-(4-(2-(2,6-Dichlorophenyl)-3-(hydroxymethyl)imidazo[2,1-f][1,6]naphthyridin-9-yl)-1H-pyrazol-1-yl)propan-2-ol

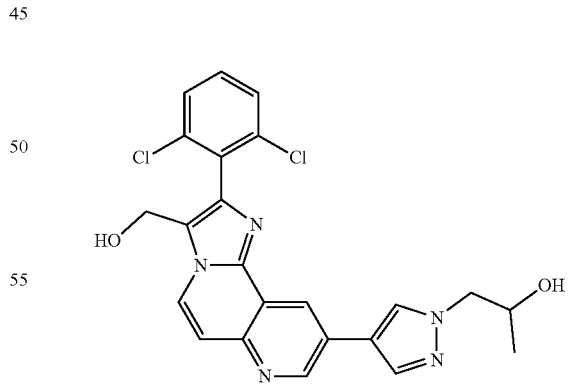

This compound was prepared according to the procedures described in Example 15, with 1-(4-(4,4,5,5-tetramethyl-1,3,2-dioxaborolan-2-yl)-1H-pyrazol-1-yl)propan-2-ol replacing (1-ethyl-1H-pyrazol-4-yl)boronic acid. LCMS calculated for $C_{23}H_{20}Cl_2N_5O_2$ (M+H)$^+$: m/z=468.1/470.1; found: 468.1/470.1. This racemate was separated into pure enantiomers by subjecting to chiral SFC (Phenomenex Lux Sum Cellulose-21.1×250 mm column, eluting with an isocratic solution of 35% MeOH in $CO_2$, at a flow rate of 60 mL/min $t_{R,\,peak\,1}$=6.6 min, $t_{R,\,peak\,2}$=7.6 min). After the solvent was evaporated in vacuo, each enantiomer was purified by prep-LCMS (XBridge C18 column, eluting with a gradient of acetonitrile/water containing 0.1% TFA, at flow rate of 60 mL/min) to provide each enantiomer of the title compound as the TFA salt.

Example 19. 2-(4-(2-(2,6-Dichlorophenyl)-3-(hydroxymethyl)imidazo[2,1-f][1,6]naphthyridin-9-yl)-1H-pyrazol-1-yl)-N,N-dimethylacetamide

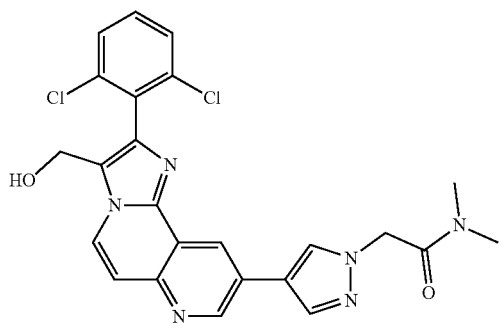 [SMILES: CN(C)C(=O)Cn1cc(-c2cnc3ccn4c(CO)c(-c5c(Cl)cccc5Cl)nc4c3c2)cn1]

Step 1. 2-(4-(2-(2,6-Dichlorophenyl)-3-(hydroxymethyl)imidazo[2,1-f][1,6]naphthyridin-9-yl)-1H-pyrazol-1-yl)acetic acid

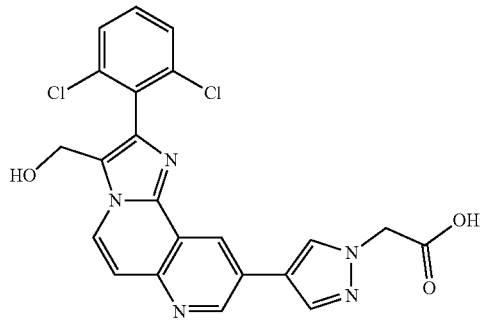 [SMILES: O=C(O)Cn1cc(-c2cnc3ccn4c(CO)c(-c5c(Cl)cccc5Cl)nc4c3c2)cn1]

A vial containing (9-bromo-2-(2,6-dichlorophenyl)imidazo[2,1-f][1,6]naphthyridin-3-yl)methanol (Intermediate 1, 15 mg, 0.035 mmol), methyl 2-(4-(4,4,5,5-tetramethyl-1,3,2-dioxaborolan-2-yl)-1H-pyrazol-1-yl)acetate (10 mg, 0.035 mmol), potassium phosphate, tribasic (23 mg, 0.106 mmol), and (1,1'-bis(diphenylphosphino)ferrocene)dichloropalladium(II) (2.6 mg, 3.55 μmol) was evacuated and backfilled with nitrogen three times, followed by the addition of 1,4-dioxane (1 mL) and water (100 μL). The vial was sealed and heated to 80° C. for 30 minutes. Upon completion the reaction mixture was flushed through a SiliaPrep SPE thiol cartridge (SPE-R51030B-06P). To the filtrate was added lithium hydroxide (15 mg, 0.6 mmol) in 1 mL water, and the reaction mixture was left to stir for 20 min. Upon completion, all volatiles were removed and the crude residue was used directly for the next step. LCMS calculated for $C_{22}H_{16}Cl_2N_5O_3$ (M+H)$^+$: m/z=468.1/470.1; found 468.1/470.0.

Step 2. 2-(4-(2-(2,6-Dichlorophenyl)-3-(hydroxymethyl)imidazo[2,1-f][1,6]naphthyridin-9-yl)-1H-pyrazol-1-yl)-N,N-dimethylacetamide To a vial containing 2-(4-(2-(2,6-dichlorophenyl)-3-(hydroxymethyl)imidazo[2,1-f][1,6]naphthyridin-9-yl)-1H-pyrazol-1-yl)acetic acid (15 mg, 0.032 mmol) was added dimethylamine hydrochloride (3 mg, 0.032 mmol), DMF (0.5 ml) and DIPEA (11 μL, 0.064 mmol). The solution was stirred for 1 min before adding HATU (18 mg, 0.048 mmol) and leaving to stir for 1 h. Upon completion, the reaction mixture was diluted with acetonitrile/methanol and purified with prep-LCMS (XBridge C18 column, eluting with a gradient of acetonitrile/water containing 0.1% TFA, at flow rate of 60 mL/min) to provide the title compound as the TFA salt. LCMS calculated for $C_{24}H_{21}Cl_2N_6O_2$ (M+H)$^+$: m/z=495.1/497.1; found 495.1/497.0.

Example 20. 1-(4-(4-(2-(2,6-Dichlorophenyl)-3-(hydroxymethyl)imidazo[2,1-f][1,6]naphthyridin-9-yl)-1H-pyrazol-1-yl)piperidin-1-yl)ethan-1-one

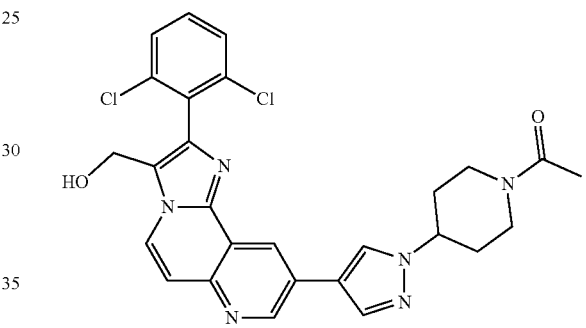

Step 1. (2-(2,6-Dichlorophenyl)-9-(1-(piperidin-4-yl)-1H-pyrazol-4-yl)imidazo[2,1-f][1,6]naphthyridin-3-yl)methanol

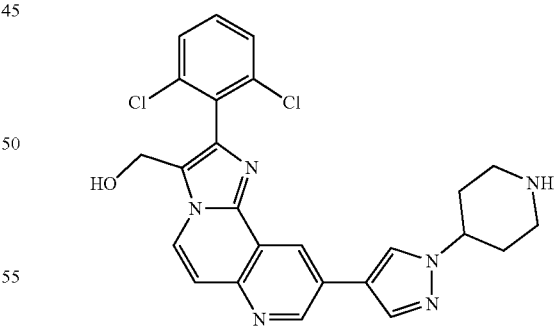

A vial containing (9-bromo-2-(2,6-dichlorophenyl)imidazo[2,1-][1,6]naphthyridin-3-yl)methanol (Intermediate 1, 50 mg, 0.118 mmol), tert-butyl 4-(4-(4,4,5,5-tetramethyl-1,3,2-dioxaborolan-2-yl)-1H-pyrazol-1-yl)piperidine-1-carboxylate (45 mg, 0.118 mmol), potassium phosphate, tribasic (75 mg, 0.355 mmol), and (1,1'-bis(diphenylphosphino) ferrocene) dichloropalladium(II) (9 mg, 0.012 mmol) was evacuated and backfilled with nitrogen three times, followed by the addition of 1,4-dioxane (1 mL) and water (100 μL).

The vial was sealed and heated to 80° C. for 30 minutes. Upon completion the reaction was diluted with CH$_2$Cl$_2$, and flushed through celite. The filtrate was concentrated in vacuo, and taken up in 1 mL CH$_2$Cl$_2$ and 0.5 mL TFA. Upon reaction completion, the volatiles were removed and the residue was suspended in MeOH (1 mL) and poured into sat aq. NaHCO$_3$. The resulting precipitate was filtered, dried under vacuum and used directly for the next step. LCMS calculated for C$_{25}$H$_{23}$Cl$_2$N$_6$O(M+H)$^+$: m/z=493.1/495.1; found 493.1/495.0.

Step 2. 1-(4-(4-(2-(2,6-Dichlorophenyl)-3-(hydroxymethyl)imidazo[2,1-f][1,6]naphthyridin-9-yl)-1H-pyrazol-1-yl)piperidin-1-yl)ethan-1-one To a vial containing (2-(2,6-dichlorophenyl)-9-(1-(piperidin-4-yl)-1H-pyrazol-4-yl)imidazo[2,1-f][1,6]naphthyridin-3-yl)methanol (10 mg, 0.020 mmol) was added acetic acid (1.2 µL, 0.020 mmol), DMF (0.5 mL) and DIPEA (7 µL, 0.04 mmol). The solution was stirred for 1 min before adding HATU (12 mg, 0.03 mmol) and leaving to stir for 1 h. Upon completion the reaction mixture was diluted with acetonitrile/methanol and purified with prep-LCMS (XBridge C18 column, eluting with a gradient of acetonitrile/water containing 0.1% TFA, at flow rate of 60 mL/min) to provide the title compound as the TFA salt. LCMS calculated for C$_{27}$H$_{25}$Cl$_2$N$_6$O$_2$(M+H)$^+$: m/z=535.1/537.1; found 535.1/537.1.

Example 21. 1-(4-(4-(2-(2-Chloro-6-methylphenyl)-3-(hydroxymethyl)imidazo[2,1-f][1,6]naphthyridin-9-yl)-1H-pyrazol-1-yl)piperidin-1-yl)-2-methoxyethan-1-one

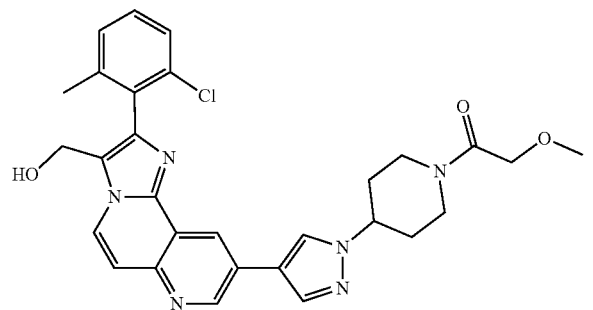 [SMILES: COCC(=O)N1CCC(n2cc(-c3cnc4ccn5c(CO)c(-c6c(C)cccc6Cl)nc5c4c3)cn2)CC1]

Step 1. 1-(4-(4-(2-(2,6-Dichlorophenyl)-3-(hydroxymethyl)imidazo[2,1-f][1,6]naphthyridin-9-yl)-1H-pyrazol-1-yl)piperidin-1-yl)-2-methoxyethan-1-one

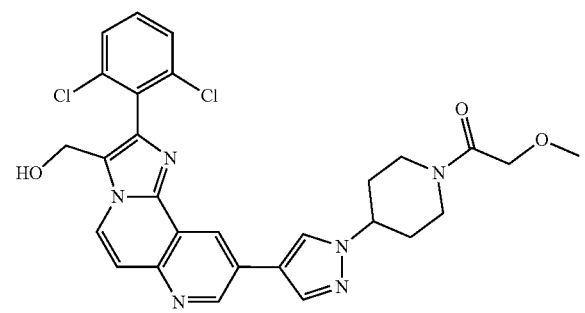 [SMILES: COCC(=O)N1CCC(n2cc(-c3cnc4ccn5c(CO)c(-c6c(Cl)cccc6Cl)nc5c4c3)cn2)CC1]

This compound was prepared according to the procedures described in Example 20, with 2-methoxyacetic acid replacing acetic acid in Step 2. LCMS calculated for C$_{28}$H$_{27}$Cl$_2$N$_6$O$_3$ (M+H)$^+$: m/z=565.2/567.2; found: 565.2/567.2.

Step 2. 1-(4-(4-(2-(2-Chloro-6-methylphenyl)-3-(hydroxymethyl)imidazo[2,1-f][1,6]naphthyridin-9-yl)-H-pyrazol-1-yl)piperidin-1-yl)-2-methoxyethan-1-one A microwave vial containing a mixture of 1-(4-(4-(2-(2,6-dichlorophenyl)-3-(hydroxymethyl)imidazo[2,1-][1,6]naphthyridin-9-yl)-1H-pyrazol-1-yl)piperidin-1-yl)-2-methoxyethan-1-one (25 mg, 0.044 mmol), Pd$_2$(dba)$_3$ (2 mg, 2.2 µmol), 9,9-dimethyl-4,5-bis(diphenylphosphino)xanthene (4 mg, 6.63 µmol), and potassium carbonate (12 mg, 0.088 mmol) was evacuated and backfilled with nitrogen three times, followed by the addition of 1,4-dioxane (2 mL) and trimethylboroxine (7 µL, 0.05 mmol). The vial was irradiated at 130° C. for 2 h using a Biotage Initator+ Microwave Synthesizer. After cooling to room temperature, the mixture was filtered through celite and washed with CH$_2$Cl$_2$, followed by concentration of the filtrate in vacuo. The residue was then dissolved with CH$_3$CN and purified with prep-LCMS (XBridge C18 column, eluting with a gradient of acetonitrile/water containing 0.1% TFA, at flow rate of 60 mL/min) to provide the title compound as the TFA salt. LCMS calculated for C$_{29}$H$_{30}$ClN$_6$O$_3$(M+H)$^+$: m/z=545.2; found 545.3.

Example 22. 1-(4-(2-(2-Chloro-6-methylphenyl)-3-(hydroxymethyl)imidazo[2,1-f][1,6]naphthyridin-9-yl)-1H-pyrazol-1-yl)-2-methylpropan-2-ol

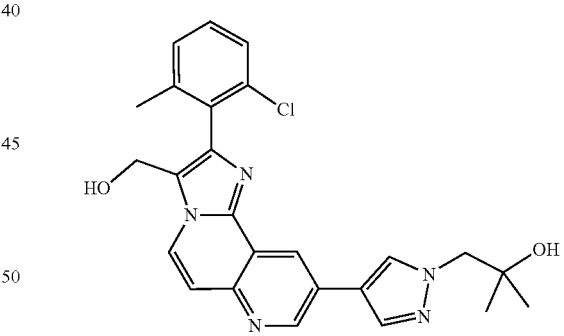

This compound was prepared according to the procedures described in Example 11, with 2-methyl-1-(4-(4,4,5,5-tetramethyl-1,3,2-dioxaborolan-2-yl)-1H-pyrazol-1-yl)propan-2-ol replacing 1-methyl-4-(4-(4,4,5,5-tetramethyl-1,3,2-dioxaborolan-2-yl)-1H-pyrazol-1-yl)piperidine in Step 1 to provide the title compound as the TFA salt. LCMS calculated for C$_{25}$H$_{25}$ClN$_5$O$_2$ (M+H)$^+$: m/z=462.2; found: 462.2. $^1$H NMR (600 MHz, DMSO-d$_6$) δ 9.30 (d, J=2.3 Hz, 1H), 8.95 (d, J=2.3 Hz, 1H), 8.57 (d, J=7.4 Hz, 1H), 8.47 (s, 1H), 8.21 (s, 1H), 7.51 (d, J=7.3 Hz, 1H), 7.48-7.42 (m, 2H), 7.40-7.36 (m, 1H), 4.75 (d, J=13.6 Hz, 1H), 4.57 (d, J=13.6 Hz, 1H), 4.09 (s, 2H), 2.18 (s, 3H), 1.12 (s, 6H).

Example 23. 3-(4-(2-(2,6-Dichlorophenyl)-3-(hydroxymethyl)imidazo[2,1-f][1,6]naphthyridin-9-yl)-1H-pyrazol-1-yl)butanenitrile

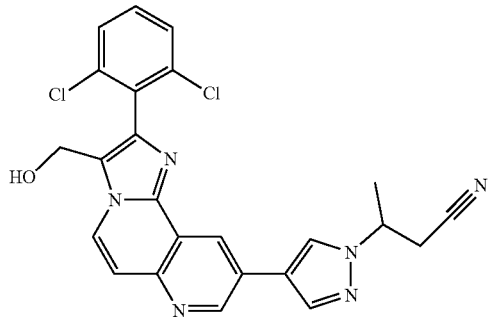 [SMILES: CC(CC#N)n1cc(-c2cnc3ccn4c(CO)c(-c5c(Cl)cccc5Cl)nc4c3c2)cn1]

To a vial containing a mixture of (2-(2,6-dichlorophenyl)-9-(1H-pyrazol-4-yl)imidazo[2,1-f][1,6]naphthyridin-3-yl)methanol (Example 1, Step 1, 15 mg, 0.037 mmol) and cesium carbonate (15 mg, 0.044 mmol) as a solution in DMF (500 μL) was added 3-bromobutanenitrile (6 mg, 0.037 mmol). The vial was sealed and heated to 80° C. for 16 h. After cooling to room temperature, the mixture was then diluted with CH$_3$CN and purified with prep-LCMS (XBridge C18 column, eluting with a gradient of acetonitrile/water containing 0.1% TFA, at flow rate of 60 mL/min). LCMS calculated for C$_{24}$H$_{19}$Cl$_2$N$_6$O (M+H)$^+$: m/z=477.1/479.1; found 477.2/479.2. This racemate was separated into pure enantiomers by subjecting to chiral SFC (Phenomenex Lux Sum Cellulose-2 1.1×250 mm column, eluting with an isocratic solution of 30% MeOH in CO$_2$, at a flow rate of 60 mL/min t$_{R, peak\ 1}$=10.4 min, t$_{R, peak\ 2}$=11.75 min). After the solvent was evaporated in vacuo, both enantiomers were purified by prep-LCMS (XBridge C18 column, eluting with a gradient of acetonitrile/water containing 0.1% TFA, at flow rate of 60 mL/min) to provide each enantiomer of the title compound as the TFA salt. $^1$H NMR (600 MHz, DMSO-d$_6$) δ 9.30 (d, J=2.2 Hz, 1H), 8.99 (d, J=2.3 Hz, 1H), 8.77 (s, 1H), 8.56 (d, J=7.4 Hz, 1H), 8.34 (s, 1H), 7.65 (d, J=8.1 Hz, 2H), 7.56 (dd, J=8.7, 7.6 Hz, 1H), 7.47 (d, J=7.4 Hz, 1H), 4.80 (h, J=6.7 Hz, 1H), 4.69 (s, 2H), 3.18-3.15 (m, 2H), 1.59 (d, J=6.8 Hz, 3H).

Example 24. (R)-2-(4-(2-(2,6-Dichlorophenyl)-3-(hydroxymethyl)imidazo[2,1-f][1,6]naphthyridin-9-yl)-1H-pyrazol-1-yl)propan-1-ol

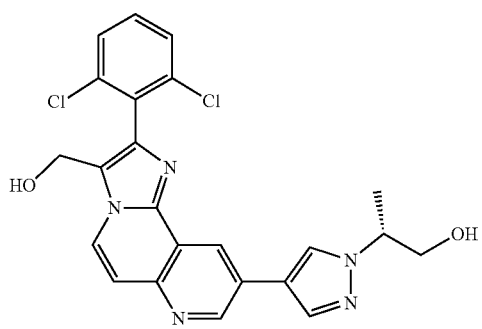 [SMILES: C[C@H](CO)n1cc(-c2cnc3ccn4c(CO)c(-c5c(Cl)cccc5Cl)nc4c3c2)cn1]

This compound was prepared according to the procedures described in Example 23, with (S)-2-chloropropan-1-ol replacing 3-bromobutanenitrile to provide the title compound as the TFA salt. LCMS calculated for C$_{23}$H$_{20}$Cl$_2$N$_5$O$_3$ (M+H)$^+$: m/z=468.1/470.1; found: 468.1/470.1.

Example 25. (2-(2,6-Dichlorophenyl)-9-(1-((4-fluorotetrahydro-2H-pyran-4-yl)methyl)-1H-pyrazol-4-yl)imidazo[2,1-J][1,6]naphthyridin-3-yl)methanol

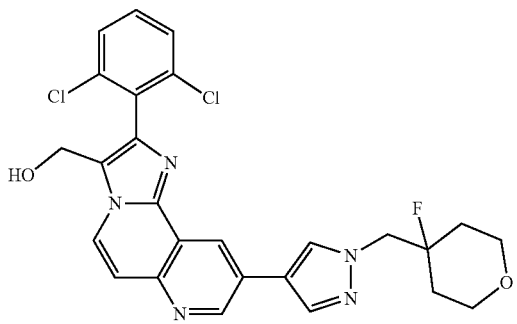 [SMILES: OCc1c(-c2c(Cl)cccc2Cl)nc2c3cc(-c4cnn(CC5(F)CCOCC5)c4)cnc3ccn12]

This compound was prepared according to the procedures described in Example 23, with 4-(bromomethyl)-4-fluorotetrahydro-2H-pyran replacing 3-bromobutanenitrile to provide the title compound as the TFA salt. LCMS calculated for C$_{26}$H$_{23}$Cl$_2$FN$_5$O$_2$ (M+H)$^+$: m/z=526.1/528.1; found: 526.1/528.1.

Example 26. 3-(4-(2-(2,6-Dichlorophenyl)-3-(hydroxymethyl)imidazo[2,1-f][1,6]naphthyridin-9-yl)-1H-pyrazol-1-yl)tetrahydro-2H-thiopyran 1,1-dioxide

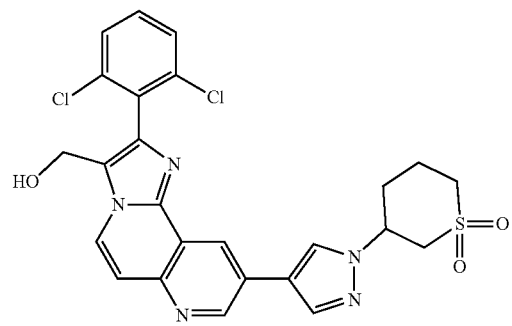 [SMILES: O=S1(=O)CCCC(n2cc(-c3cnc4ccn5c(CO)c(-c6c(Cl)cccc6Cl)nc5c4c3)cn2)C1]

This compound was prepared according to the procedures described in Example 23, with 4-iodotetrahydro-2H-thiopyran 1,1-dioxide replacing 3-bromobutanenitrile. [note: the 4-substituted thiopyrandioxide product was not observed] LCMS calculated for C$_{25}$H$_{22}$Cl$_2$N$_5$O$_3$S (M+H)$^+$: m/z=542.1/544.1; found: 542.1/544.1. This racemate was separated into pure enantiomers by subjecting to chiral HPLC (Phenomenex Lux Sum Cellulose-21.2×250 mm column, eluting with an isocratic solution of 85% EtOH in hexanes, at a flow rate of 20 mL/min t$_{R, peak\ 1}$=11.2 min, t$_{R, peak\ 2}$=15.6 min). After the solvent was evaporated in vacuo, both enantiomers were purified by prep-LCMS (XBridge C18 column, eluting with a gradient of acetonitrile/water containing 0.1% TFA, at flow rate of 60 mL/min)

to provide each enantiomer of the title compound as the TFA salt $^1$H NMR (600 MHz, DMSO-$d_6$) δ 9.25 (d, J=2.2 Hz, 1H), 8.95 (d, J=2.3 Hz, 1H), 8.74 (s, 1H), 8.54 (d, J=7.5 Hz, 1H), 8.32 (s, 1H), 7.65 (d, J=8.1 Hz, 2H), 7.55 (dd, J=8.7, 7.6 Hz, 1H), 7.45 (d, J=7.4 Hz, 1H), 4.75-4.64 (m, 3H), 3.70 (dd, J=13.3, 11.9 Hz, 1H), 3.63 (dtd, J=13.5, 3.8, 1.5 Hz, 1H), 3.21 (dtd, J=28.1, 14.1, 3.8 Hz, 2H), 2.20 (tdd, J=14.4, 6.8, 3.3 Hz, 2H), 2.12-2.03 (m, 1H), 1.92 (tdd, J=12.8, 10.8, 3.6 Hz, 1H).

Example 27. 1-(3-((4-(2-(2,6-Dichlorophenyl)-3-(hydroxymethyl)imidazo[2,1-f][1,6]naphthyridin-9-yl)-1H-pyrazol-1-yl)methyl)azetidin-1-yl)-2-methoxyethan-1-one

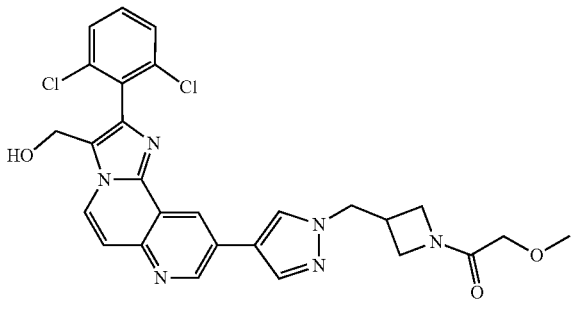 [SMILES: COCC(=O)N1CC(Cn2cc(-c3cnc4ccn5c(CO)c(-c6c(Cl)cccc6Cl)nc5c4c3)cn2)C1]

Step 1. (9-(1-(Azetidin-3-ylmethyl)-1H-pyrazol-4-yl)-2-(2,6-dichlorophenyl)imidazo[2,1-f][1,6]naphthyridin-3-yl)methanol

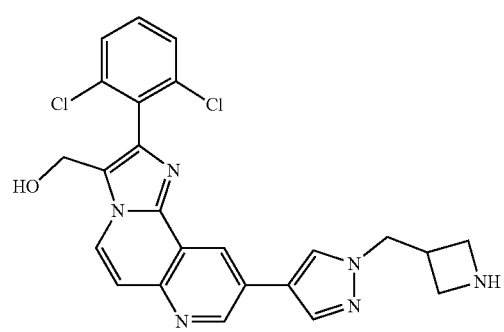 [SMILES: OCc1c(-c2c(Cl)cccc2Cl)nc2c3cc(-c4cnn(CC5CNC5)c4)cnc3ccn12]

This compound was prepared according to the procedures described in Example 20, with tert-butyl 3-((4-(4,4,5,5-tetramethyl-1,3,2-dioxaborolan-2-yl)-1H-pyrazol-1-yl)methyl)azetidine-1-carboxylate replacing tert-butyl 4-(4-(4,4,5,5-tetramethyl-1,3,2-dioxaborolan-2-yl)-1H-pyrazol-1-yl)piperidine-1-carboxylate in Step 1. LCMS calculated for $C_{24}H_{21}Cl_2N_6O$ (M+H)$^+$: m/z=479.1/481.1; found: 479.3/481.2.

Step 2. 1-(3-((4-(2-(2,6-Dichlorophenyl)-3-(hydroxymethyl)imidazo[2,1-f][1,6]naphthyridin-9-yl)-1H-pyrazol-1-yl)methyl)azetidin-1-yl)-2-methoxyethan-1-one To a vial containing (9-(1-(azetidin-3-ylmethyl)-1H-pyrazol-4-yl)-2-(2,6-dichlorophenyl)imidazo[2,1-f][1,6]naphthyridin-3-yl)methanol (10 mg, 0.021 mmol) was added 2-methoxyacetic acid (2 μL, 0.020 mmol), DMF (500 μl) and DIPEA (7 μL, 0.04 mmol). The solution was stirred for 1 min before adding HATU (12 mg, 0.03 mmol) and leaving to stir for 1 h. Upon completion the reaction mixture was diluted with acetonitrile/methanol and purified with prep-LCMS (XBridge C18 column, eluting with a gradient of acetonitrile/water containing 0.1% TFA, at flow rate of 60 mL/min) to provide the title compound as the TFA salt. LCMS calculated for $C_{27}H_{25}Cl_2N_6O_3$ (M+H)$^+$: m/z=551.1/553.1; found 551.2/553.2.

Example 28. 2-(2,6-Dichlorophenyl)-3-(difluoromethyl)-9-(1-(2-(methylsulfonyl)ethyl)-1H-pyrazol-4-yl)imidazo[2,1-f][1,6]naphthyridine

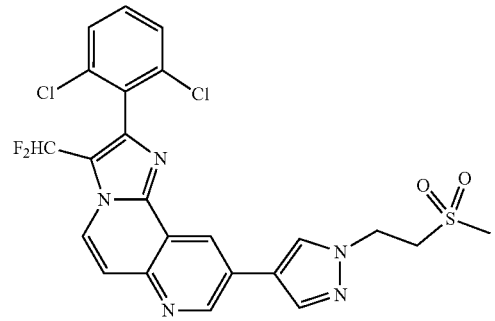 [SMILES: CS(=O)(=O)CCn1cc(-c2cnc3ccn4c(C(F)F)c(-c5c(Cl)cccc5Cl)nc4c3c2)cn1]

Step 1. 9-Bromo-2-(2,6-dichlorophenyl)imidazo[2,1-f][1,6]naphthyridine-3-carbaldehyde

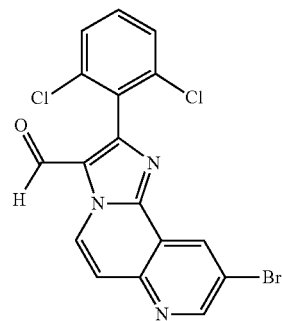 [SMILES: O=Cc1c(-c2c(Cl)cccc2Cl)nc2c3cc(Br)cnc3ccn12]

To a vial was added 9-bromo-2-(2,6-dichlorophenyl)-3-vinylimidazo[2,1-f][1,6]naphthyridine (240 mg, 0.573 mmol), THF (4.5 mL), water (1.1 mL) and osmium tetroxide (4 wt. % in H$_2$O, 91 μL, 14 μmol), followed by sodium periodate (612 mg, 2.86 mmol). The reaction mixture was stirred at 30° C. for 2 h, and upon completion the reaction was quenched with saturated aqueous Na$_2$S$_2$O$_3$ and extracted into EtOAc. The combined organic layers were concentrated in vacuo. The resulting residue was purified by Biotage Isolera to give the desired product as a yellow oil. LCMS calculated for $C_{17}H_9BrCl_2N_3O$ (M+H)$^+$: m/z=419.9/421.9; found 419.9/421.9.

Step 2. 9-Bromo-2-(2,6-dichlorophenyl)-3-(difluoromethyl)imidazo[2,1-f][1,6]naphthyridine

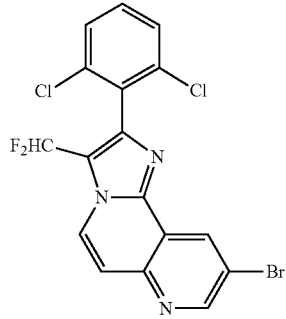 [SMILES: FC(F)c1c(-c2c(Cl)cccc2Cl)nc2c3cc(Br)cnc3ccn12]

To a vial containing 9-bromo-2-(2,6-dichlorophenyl)imidazo[2,1-f][1,6]naphthyridine-3-carbaldehyde (97 mg, 0.230 mmol) as a solution in CH$_2$Cl$_2$ (1.0 mL) at 0° C. was added diethylaminosulfur trifluoride (152 μL, 1.152 mmol) in a dropwise fashion. The reaction mixture was stirred at 40° C. for 16 h, and upon completion the reaction was carefully quenched with saturated aqueous NaHCO$_3$ and extracted into EtOAc. The combined organic layers were concentrated in vacuo. The resulting residue was purified by Biotage Isolera to give the desired product as a yellow oil. LCMS calculated for C$_{17}$H$_9$BrCl$_2$F$_2$N$_3$(M+H)$^+$: m/z=441.9/443.9; found 441.9/443.9.

Step 3. 2-(2,6-Dichlorophenyl)-3-(difluoromethyl)-9-(1-(2-(methylsulfonyl)ethyl)-1H-pyrazol-4-yl)imidazo[2,1-f][1,6]naphthyridine A vial containing 9-bromo-2-(2,6-dichlorophenyl)-3-(difluoromethyl)imidazo[2,1-f][1,6]naphthyridine (90 mg, 0.203 mmol), 1-(2-(methylsulfonyl)ethyl)-4-(4,4,5,5-tetramethyl-1,3,2-dioxaborolan-2-yl)-1H-pyrazole (73 mg, 0.244 mmol), potassium phosphate, tribasic (86 mg, 0.406 mmol), and (1,1'-bis(diphenylphosphino)ferrocene)dichloropalladium(II) dichloromethane adduct (17 mg, 0.020 mmol) was evacuated and backfilled with nitrogen three times, followed by the addition of 1,4-dioxane (1.9 mL) and water (190 μL). The vial was sealed and heated to 80° C. for 1 h. After cooling to room temperature, the mixture was filtered through a SiliaPrep SPE thiol cartridge (SPE-R51030B-06P) and washed with acetonitrile. The mixture was then diluted with acetonitrile and purified with prep-LCMS (XBridge C18 column, eluting with a gradient of acetonitrile/water containing 0.1% TFA, at flow rate of 60 mL/min) to provide the title compound as the TFA salt. LCMS calculated for C$_{23}$H$_{18}$Cl$_2$F$_2$N$_5$O$_2$S (M+H)$^+$: m/z=536.1/538.0; found 536.0/538.0. $^1$H NMR (500 MHz, DMSO-d$_6$) δ 9.35 (d, J=2.3 Hz, 1H), 9.02 (d, J=2.2 Hz, 1H), 8.73 (s, 1H), 8.59 (d, J=7.5 Hz, 1H), 8.36 (s, 1H), 7.70-7.64 (m, 2H), 7.63-7.55 (m, 2H), 7.54-7.17 (m, 1H), 4.61 (t, J=6.9 Hz, 2H), 3.78 (t, J=6.8 Hz, 2H), 2.92 (s, 3H).

Example 29. 2-(4-(2-(2,6-Dichlorophenyl)-3-(difluoromethyl)imidazo[2,1-f][1,6]naphthyridin-9-yl)-1H-pyrazol-1-yl)acetonitrile

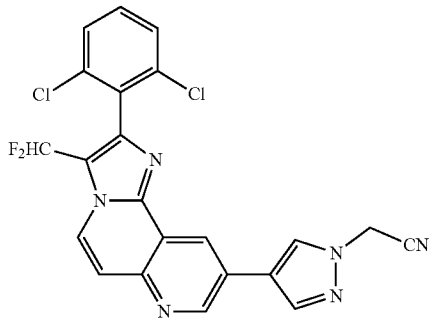 [SMILES: N#CCn1cc(-c2cnc3ccn4c(C(F)F)c(-c5c(Cl)cccc5Cl)nc4c3c2)cn1]

This compound was prepared according to the procedures described in Example 28, with 2-(4-(4,4,5,5-tetramethyl-1,3,2-dioxaborolan-2-yl)-1H-pyrazol-1-yl)acetonitrile replacing 1-(2-(methylsulfonyl)ethyl)-4-(4,4,5,5-tetramethyl-1,3,2-dioxaborolan-2-yl)-1H-pyrazole in Step 3 to provide the title compound as the TFA salt. LCMS calculated for C$_{22}$H$_{13}$Cl$_2$F$_2$N$_6$ (M+H)$^+$: m/z=469.1/471.1; found 469.0/471.0.

Example 30. 2-(2,6-Dichlorophenyl)-3-(difluoromethyl)-9-(1-(tetrahydro-2H-pyran-4-yl)-1H-pyrazol-4-yl)imidazo[2,1-J][1,6]naphthyridine

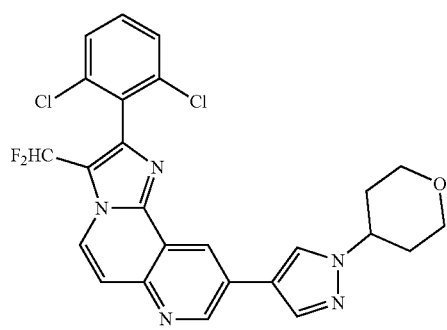 [SMILES: FC(F)c1c(-c2c(Cl)cccc2Cl)nc2c3cc(-c4cnn(C5CCOCC5)c4)cnc3ccn12]

This compound was prepared according to the procedures described in Example 28, with 1-(tetrahydro-2H-pyran-4-yl)-4-(4,4,5,5-tetramethyl-1,3,2-dioxaborolan-2-yl)-1H-pyrazole replacing 1-(2-(methylsulfonyl)ethyl)-4-(4,4,5,5-tetramethyl-1,3,2-dioxaborolan-2-yl)-1H-pyrazole in Step 3

Example 31. 2-(4-(2-(2,6-Dichlorophenyl)-3-(difluoromethyl)imidazo[2,1-f][1,6]naphthyridin-9-yl)-1H-pyrazol-1-yl)ethan-1-ol

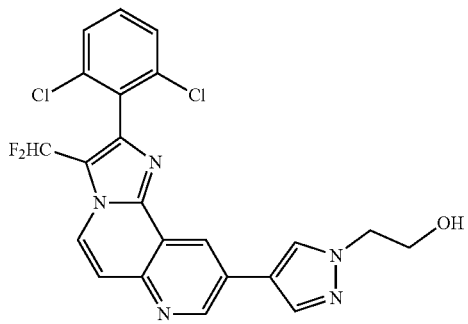 [SMILES: OCCn1cc(-c2cnc3ccn4c(C(F)F)c(-c5c(Cl)cccc5Cl)nc4c3c2)cn1]

This compound was prepared according to the procedures described in Example 28, with 2-(4-(4,4,5,5-tetramethyl-1,3,2-dioxaborolan-2-yl)-1H-pyrazol-1-yl)ethan-1-ol replacing 1-(2-(methylsulfonyl)ethyl)-4-(4,4,5,5-tetramethyl-1,3,2-dioxaborolan-2-yl)-1H-pyrazole in Step 3 to provide the title compound as the TFA salt. LCMS calculated for $C_{22}H_{16}Cl_2F_2N_5O$ (M+H)$^+$: m/z=474.1/476.1; found 474.0/476.0.

Example 32. 2-(4-(2-(2,6-Dichlorophenyl)-3-(difluoromethyl)imidazo[2,1-f][1,6]naphthyridin-9-yl)-1H-pyrazol-1-yl)propanenitrile

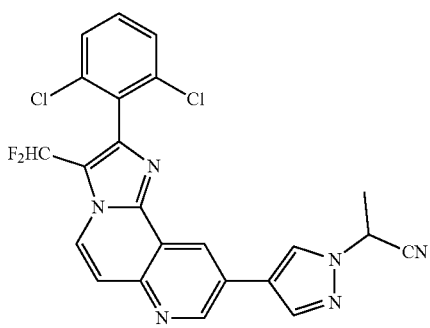

This compound was prepared according to the procedures described in Example 28, with 2-(4-(4,4,5,5-tetramethyl-1,3,2-dioxaborolan-2-yl)-1H-pyrazol-1-yl)propanenitrile replacing 1-(2-(methylsulfonyl)ethyl)-4-(4,4,5,5-tetramethyl-1,3,2-dioxaborolan-2-yl)-1H-pyrazole in Step 3 to provide the title compound as the TFA salt. LCMS calculated for $C_{23}H_{15}Cl_2F_2N_6$ (M+H)$^+$: m/z=483.1/485.1; found 483.0/485.0.

Example 33. 2-(4-(2-(2,6-Dichlorophenyl)-3-(difluoromethyl)imidazo[2,1-f][1,6]naphthyridin-9-yl)-1H-pyrazol-1-yl)-2-methylpropanamide

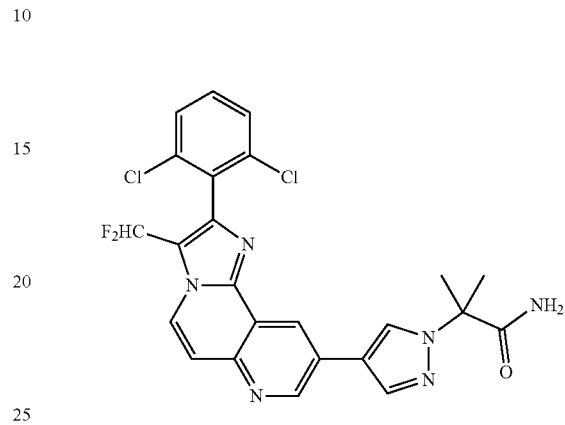

This compound was prepared according to the procedures described in Example 28, with 2-methyl-2-(4-(4,4,5,5-tetramethyl-1,3,2-dioxaborolan-2-yl)-1H-pyrazol-1-yl)propanamide replacing 1-(2-(methylsulfonyl)ethyl)-4-(4,4,5,5-tetramethyl-1,3,2-dioxaborolan-2-yl)-1H-pyrazole in Step 3 to provide the title compound as the TFA salt. LCMS calculated for $C_{24}H_{19}Cl_2F_2N_6O$ (M+H)$^+$: m/z=515.1/517.1; found 515.1/517.0.

Example 34. 2-(2-(2,6-Dichlorophenyl)-9-(1-(1-methylpiperidin-4-yl)-1H-pyrazol-4-yl)imidazo[2,1-f][1,6]naphthyridin-3-yl)ethan-1-ol

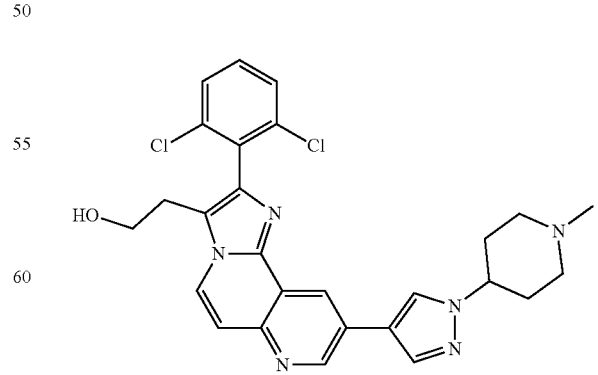

Step 1. 2-(9-Bromo-2-(2,6-dichlorophenyl)imidazo[2,1-f][1,6]naphthyridin-3-yl)ethan-1-ol

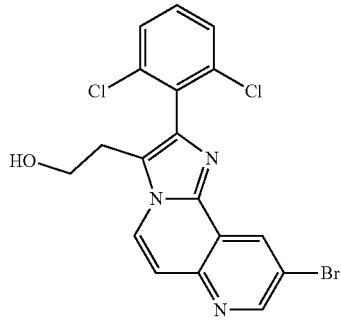 [SMILES: OCCc1c(-c2c(Cl)cccc2Cl)nc2c3cc(Br)cnc3ccn12]

To a vial containing 9-bromo-2-(2,6-dichlorophenyl)-3-vinylimidazo[2,1-f][1,6]naphthyridine (40 mg, 0.095 mmol) as a solution in THF (320 μL) was added 9-borabicyclo[3.3.1]nonane (0.5 M in THF, 380 μL, 0.190 mmol). The reaction mixture was stirred at 50° C. for 16 h. Upon consumption of the starting material, 2M aqueous sodium hydroxide (500 μL) and hydrogen peroxide (30% wt % in $H_2O$, 200 μL) was added to the vial. The reaction mixture was stirred at 50° C. for another 3 h. After cooling to room temperature, the solution was quenched with saturated aqueous $NaHCO_3$ and extracted into EtOAc. The combined organic layers were concentrated in vacuo. The resulting residue was purified by Biotage Isolera to give the desired product as a yellow oil. LCMS calculated for $C_{18}H_{13}BrCl_2N_3O$ $(M+H)^+$: m/z=436.0/438.0; found 436.0/438.0.

Step 2. 2-(2-(2,6-Dichlorophenyl)-9-(1-(1-methylpiperidin-4-yl)-1H-pyrazol-4-yl)imidazo[2,1-f][1,6]naphthyridin-3-yl)ethan-1-ol A vial containing 2-(9-bromo-2-(2,6-dichlorophenyl)imidazo[2,1-f][1,6]naphthyridin-3-yl)ethan-1-ol (3 mg, 6.9 μmol), 1-methyl-4-(4-(4,4,5,5-tetramethyl-1,3,2-dioxaborolan-2-yl)-1H-pyrazol-1-yl)piperidine (6 mg, 21 μmol), potassium phosphate, tribasic (4 mg, 21 μmol), and (1,1'-bis(diphenylphosphino)ferrocene)dichloropalladium(II) dichloromethane adduct (1 mg, 1.4 μmol) was evacuated and backfilled with nitrogen three times, followed by the addition of 1,4-dioxane (300 μL) and water (30 μL). The vial was sealed and heated to 80° C. for 1 h. After cooling to room temperature, the mixture was filtered through a SiliaPrep SPE thiol cartridge (SPE-R51030B-06P) and washed with acetonitrile. The mixture was then diluted with acetonitrile and purified with prep-LCMS (XBridge C18 column, eluting with a gradient of acetonitrile/water containing 0.1% TFA, at flow rate of 60 mL/min) to provide the title compound as the TFA salt. LCMS calculated for $C_{27}H_{27}Cl_2N_6O$ $(M+H)^+$: m/z=521.2/523.2; found 521.1/523.1.

Example 35. 2-(2,6-Dichlorophenyl)-9-(1-(tetrahydro-2H-pyran-4-yl)-1H-pyrazol-4-yl)imidazo[2,1-f][1,6]naphthyridin-3-amine

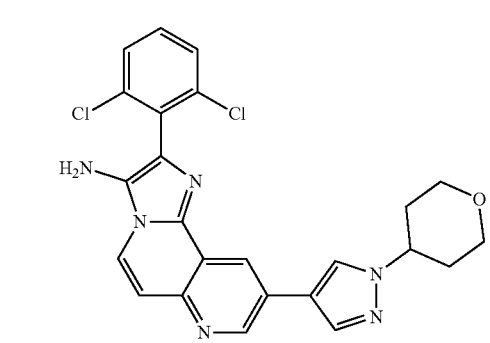 [SMILES: Nc1c(-c2c(Cl)cccc2Cl)nc2c3cc(-c4cnn(C5CCOCC5)c4)cnc3ccn12]

Step 1. 9-Bromo-2-(2,6-dichlorophenyl)imidazo[2,1-f][1,6]naphthyridin-3-amine A vial containing 9-bromo-2-(2,6-dichlorophenyl)imidazo[2,1-f][1,6]naphthyridine (140 mg, 0.356 mmol), tert-butyl nitrite (184 mg, 1.781 mmol) in acetonitrile (1.4 mL) was stirred at 50° C. for 16 h. The solution was subsequently cooled to room temperature, concentrated in vacuo and the residue was dissolved in MeOH (2 mL), and Pd/C (10 wt %, 28 mg, 0.026 mmol) was added. The vial was purged with hydrogen for 5 min and then stirred for 1 h under an atmosphere of hydrogen. The reaction mixture was then filtered and washed with $CH_2Cl_2$, followed by concentration of the filtrate in vacuo. The resulting residue was purified by Biotage Isolera to give the desired product as an orange solid. LCMS calculated for $C_{16}H_{10}BrCl_2N_4$ $(M+H)^+$: m/z=406.9/408.9; found 407.0/409.0.

Step 2. 2-(2,6-Dichlorophenyl)-9-(1-(tetrahydro-2H-pyran-4-yl)-1H-pyrazol-4-yl)imidazo[2,1-f][1,6]naphthyridin-3-amine A vial containing 9-bromo-2-(2,6-dichlorophenyl)imidazo[2,1-f][1,6]naphthyridin-3-amine (12 mg, 0.029 mmol), 1-(tetrahydro-2H-pyran-4-yl)-4-(4,4,5,5-tetramethyl-1,3,2-dioxaborolan-2-yl)-1H-pyrazole (16 mg, 0.059 mmol), potassium phosphate, tribasic (13 mg, 0.059 mmol), and (1,1'-bis(diphenylphosphino)ferrocene)dichloropalladium(II) dichloromethane adduct (2.4 mg, 2.9 μmol) was evacuated and backfilled with nitrogen three times, followed by the addition of 1,4-dioxane (270 μL) and water (27 μL). The vial was sealed and heated to 80° C. for 1 h. After cooling to room temperature, the mixture was filtered through a SiliaPrep SPE thiol cartridge (SPE-R51030B-06P) and washed with acetonitrile. The mixture was then diluted with acetonitrile and purified with prep-LCMS (XBridge C18 column, eluting with a gradient of acetonitrile/water containing 0.1% TFA, at flow rate of 60 mL/min) to provide the title compound as the TFA salt. LCMS calculated for $C_{24}H_{21}Cl_2N_6O$ $(M+H)^+$: m/z=479.1/481.1; found 479.1/481.1.

Example A: FGFR Enzymatic Assay

The inhibitor potency of the exemplified compounds was determined in an enzyme discontinuous assay that measures peptide phosphorylation using FRET measurements to detect product formation. Inhibitors were serially diluted in DMSO and a volume of 0.2 μL was transferred to the wells of a 384-well plate. A 5 μL/well volume of enzyme isoforms of FGFR (-1, -2, -3 wild-type and mutant isoforms, -4) including phosphorylated and un-phosphorylated proteins diluted in assay buffer (50 mM HEPES, 10 mM $MgCl_2$, 1 mM EGTA, 0.01% Tween-20, 5 mM DTT, pH 7.5) was added to the plate and pre-incubated with inhibitor for 5 to 15 minutes at ambient temperature. Appropriate controls (enzyme blank and enzyme with no inhibitor) were included on the plate. The reaction was initiated by the addition of a 5 μL/well volume containing both biotinylated EQEDE-PEGDYFEWLE peptide substrate (SEQ ID NO: 1) and ATP in assay buffer. The 10 μL/well reaction concentration of the peptide substrate was 500 nM whereas the ATP concentration was maintained near or below the ATP Km. The ATP Km values were pre-determined in a separate series of experiments. The reaction plate was incubated at 25° C. for 1 hr and the reactions were ended with the addition of 5 μL/well of quench solution (50 mM Tris, 150 mM NaCl, 0.5 mg/mL BSA, pH 7.8; 45 mM EDTA, 600 nM staurosporin, with Perkin Elmer Lance Reagents at 3.75 nM Eu-antibody PY20 and 180 nM APC-Streptavidin). The plate was allowed to equilibrate for ~10 minutes at ambient temperature before scanning on a PheraStar plate reader (BMG Labtech) instrument.

Either GraphPad prism or XLfit was used to analyze the data. The $IC_{50}$ values were derived by fitting the data to a four parameter logistic equation producing a sigmoidal dose-response curve with a variable Hill coefficient. Prism equation: $Y=Bottom+(Top-Bottom)/(1+10^{((Log\ IC_{50}-X)*Hill\ slope)})$; XLfit equation: $Y=(A+((B-A)/(1+((X/C)^D))))$ where X is the logarithm of inhibitor concentration and Y is the response. Compounds having an $IC_{50}$ of 1 μM or less are considered active.

Table 1 provides $IC_{50}$ data for compounds of the disclosure assayed in the FGFR Enzymatic Assay after dilution in assay buffer, added to the plate and pre-incubated for 4 hours. The symbol: "+" indicates an $IC_{50}$ less than 1.0 nM; "++" indicates an $IC_{50}$ greater than or equal to 1.0 nM but less than 5.0 nM.

The data in Table 1 was measured in wild-type un-phosphorylated FGFR3 protein.

TABLE 1

| Example No. | FGFR3 $IC_{50}$ (nM) |
|---|---|
| 1 | ++ |
| 2 | + |
| 3 | + |

TABLE 1-continued

| Example No. | FGFR3 $IC_{50}$ (nM) |
|---|---|
| 4 | + |
| 5 | ++ |
| 6 | ++ |
| 7 | ++ |
| 8 | ++ |
| 9 | ++ |
| 10 | ++ |
| 11 | ++ |
| 12 | + |
| 13 | ++ |
| 14 | ++ |
| 15 | ++ |
| 16 | ++ |
| 17 peak 1 | + |
| 17 peak 2 | + |
| 18 peak 1 | ++ |
| 18 peak 2 | ++ |
| 19 | ++ |
| 20 | + |
| 21 | ++ |
| 22 | ++ |
| 23 peak 1 | + |
| 23 peak 2 | + |
| 24 | ++ |
| 25 | + |
| 26 peak 1 | ++ |
| 26 peak 2 | + |
| 27 | ++ |
| 28 | + |
| 29 | + |
| 30 | + |
| 31 | + |
| 32 | + |
| 33 | + |
| 34 | ++ |
| 35 | ++ |

Example H: Luminescent Viability Assay

RT112 cells (cell lines and genetic profiles further detailed in Table 2) were purchased from ATCC (Manassas, VA) and maintained in RPMI, 10% FBS (Gibco/Life Technologies). To measure the effect of test compounds on the viability of cells, the cells were plated with RPMI 10% FBS (5×103 cells/well/in 50 μL) into black 96-well Greiner polystyrene in the presence or absence of 50 μL of a concentration range of test compounds. After 3 days, 100 μL of CellTiter-Glo Reagent (Promega) was added. Luminescence was read with a TopCount (PerkinElmer). $IC_{50}$ determination was performed by fitting the curve of percent inhibition versus the log of the inhibitor concentration using the GraphPad Prism 5.0 software.

TABLE 2

| Cell line | Histology | FGFR2/3 alteration |
|---|---|---|
| RT-112/84 | Bladder | FGFR3-TACC3 |
| RT112 | Bladder | FGFR3-TACC3 |
| RT-112 V555M* | Bladder | FGFR3-TACC3 V555M |
| UM-UC-14 | Bladder | FGFR3 S249C |
| RT-4 | Bladder | FGFR3-TACC3 |
| SW-780 | Bladder | FGFR3-BAIAP2L1 |
| KMS-11 | Multiple Myeloma | IgH-FGFR3 translocation + FGFR3 Y373C |
| OPM-2 | Multiple Myeloma | IgH-FGFR3 translocation + FGFR3 K650E |
| KATO-III | Stomach | FGFR2 amplification |
| SNU-16 | Stomach | FGFR2 amplification |
| AN3CA | Endometrial | FGFR2 N310R/N549K |

TABLE 2-continued

| Cell line | Histology | FGFR2/3 alteration |
|---|---|---|
| Ba/F3-FGFR2-BICC1 | Engineered system | FGFR2-BICC1** |
| Ba/F3-TEL-FGFR3 | Engineered system | TEL-FGFR3 |
| Ba/F3-TEL-FGFR3 V555M | Engineered system | TEL-FGFR3 V555M |
| Ba/F3-TEL-FGFR3 V555L | Engineered system | TEL-FGFR3 V555L |

*RT112 V555M: V555M mutation was engineered using CRISPR-mediated genome editing.
**FGFR2-BICC1 fusion represents the most prevalent FGFR2 alteration in cholangiocarcinoma.

Table 3 provides $IC_{50}$ data for compounds of the disclosure assayed in the luminescent viability assay for the RT-112/84 cell line. The symbol: "+" indicates an $IC_{50}$ less than 10 nM; "++" indicates an $IC_{50}$ greater than or equal to 10 nM but less than 50 nM.

TABLE 3

| Example No. | RT-112/84 $IC_{50}$ (nm) |
|---|---|
| 1 | ++ |
| 2 | ++ |
| 3 | + |
| 4 | + |
| 5 | + |
| 6 | ++ |
| 7 | ++ |
| 8 | ++ |
| 9 | ++ |
| 10 | ++ |
| 11 | ++ |
| 12 | + |
| 13 | ++ |
| 14 | ++ |
| 15 | + |
| 16 | ++ |
| 17 peak 1 | + |
| 17 peak 2 | + |
| 18 peak 1 | ++ |
| 18 peak 2 | ++ |
| 19 | ++ |
| 20 | + |
| 21 | + |
| 22 | ++ |
| 23 peak 1 | ++ |
| 23 peak 2 | ++ |
| 24 | ++ |
| 25 | + |
| 26 peak 1 | ++ |
| 26 peak 2 | + |
| 27 | ++ |
| 28 | + |
| 29 | + |
| 30 | + |
| 31 | + |
| 32 | + |
| 33 | + |
| 34 | ++ |
| 35 | ++ |

Example C: pFGFR2 and pFGFR1,3 Functional Cell HTRF Assay

To measure phosphorylated Fibroblast Growth Factor Receptor 2 (FGFR2), KATOIII cells (Human Gastric Carcinoma) are purchased from ATCC and maintained in Iscove's with 20% FBS (Gibco/Life Technologies). For the pFGFR2 assay, KATOIII cells are plated overnight in 5% FBS and Iscove's medium at $5 \times 10^4$ cells/well into Corning 96-well flat-bottom tissue culture treated plates. The next morning, 50 µl of fresh media with 0.5% FBS is incubated in the presence or absence of a concentration range of test compounds also at 50 ul, for 1 hour at 37° C., 5% CO2. Cell are washed with PBS, lysed with Cell Signaling Lysis Buffer with standard Protease inhibitors for 45 min at room temperature. 4 µl total of Cis Bio Anti Phospho-YAP d2 and Cis Bio Anti Phospho-YAP Cryptate together are added to the lysate and mixed well (following directions of the kit). 16 µl is then transferred to 384 well Greiner white plates and stored at 4° C. overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

To measure phosphorylated Fibroblast Growth Factor Receptor 3 (FGFR3), in house stable cell lines BAF3-TEL-FGFR1 or BAF3-TEL-FGFR3 are maintained in RPMI with 10% FBS and 1 ug/ml puromycin (Gibco/Life Technologies). For the assay, 12 nl of BAF3-TEL-FGFR1 or BAF3-TEL-FGFR3 cells in serum free and puromycin free RPMI media at $1 \times 10^6$ cell/ml are added to 384 Greiner white plate already containing 20 nl dots of compounds at a concentration range. The plates are gently shaken (100 rpm) for 2 minutes at room temperature to mix well and incubate for 2 hours in a single layer at 37° C., 5% CO2. 4 µl/well of 1/25 dilution of lysis buffer #3 (Cis Bio) is added with standard Protease inhibitors and shaken at 200 rpm at room temperature for 20 minutes. 4 µl total of the Cis Bio Tb-pFGFR Ab (10 ng) and d2-FGFR3 (1 ng) together are added to the lysate and mixed well. The plates are sealed and incubated at room temperature overnight in the dark. The plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

Example D: pFGFR3 Functional Whole Blood HTRF Assay

To measure phosphorylated Fibroblast Growth Factor Receptor 3 (FGFR3) in a whole blood assay, in house stable cell lines BAF3-TEL-FGFR3 are maintained in RPMI with 10% FBS and 1 µg/ml puromycin (Gibco/Life Technologies). For the assay, 100 ul BAF3-TEL-FGFR3 cells in 10% FBS and puromycin free RPMI media at $5 \times 10^4$ cell/well are added to fibronectin coated 96 well tissue culture plate (5 ug/ml) overnight at 37° C., 5% CO2. The next day, serum is separated from the top of the blood by a low speed spin, 1200, RPM, and heat inactivated by incubating at 56° C. for 15 minutes. 30 µl of the cooled serum is added to a 96 well plate pre dotted with 70 nM dots of compounds at a concentration range. Cell plates are washed gently with media, all the blood/compound mixture is added to the plates, and the plates are incubated for 2 hours at 37° C., 5% CO2. Blood from the plate is gently washed twice by adding media to the side of the wells and then dumping media from the plate, and allowing the plate to briefly sit on a paper towel to drain. 70 µl/well of 1× of lysis buffer #1 (Cis Bio) are added with standard Protease inhibitors, and are shaken at 400 rpm at room temperature for 30 minutes. Following lysis, the plate is spun down for 5 minutes and 16 uL of lysate is transferred into a 384-well small volume plate. 4 µl total of the Cis Bio Tb-pFGFR Ab (10 ng) and d2-FGFR3 (1 ng) together are added to the lysate and mixed well. The plates are sealed and incubated at room temperature overnight in the dark. Plates are read on the Pherastar plate reader at 665 nm and 620 nm wavelengths. $IC_{50}$ determination is performed by fitting the curve of inhibitor percent inhibition versus the log of the inhibitor concentration using the GraphPad Prism 5.0 software.

Example E: KATOIII Whole Blood pFGFR2α ELISA Assay

To measure tyrosine-phosphorylated Fibroblast Growth Factor Receptor 2 alpha (FGFR2α) in KATO III spiked whole blood assay, KATO III cells are purchased from ATCC and maintained in Iscove's medium with 20% FBS (Gibco/Life Technologies). To measure the inhibition of FGFR2α activity of test compounds, the cells are resuspended with Iscove's, 0.2% FBS at $5 \times 10^6$ cells/ml. 50 μL of the cells are then spiked into a 96-deep well 2 ml polypropylene assay block (Costar) in the presence or absence of a concentration range of test compounds and 300 ul human heparinized whole blood (Biological Specialty Corp, Colmar PA). After 4 hours incubation in 37° C., the red cells are lysed using Qiagen EL buffer and the cell lysates are resuspended in lysis buffer (Cell Signaling) containing standard protease inhibitor cocktail (Calbiochem/EMD) and PMSF (Sigma) for 30 minutes ice. The lysates are transferred to a standard V bottom propylene tissue culture plate and frozen overnight at −80° C. Samples are tested an in an R & D Systems DuoSet IC Human Phospho-FGF R2α ELISA and the plate is measured using a SpectraMax M5 microplate set to 450 nm with a wavelength correction of 540. $IC_{50}$ determination is performed by fitting the curve of inhibitor percent inhibition versus the log of the inhibitor concentration using the GraphPad Prism 5.0 software.

Example F: Inhibition of FGFR Pathway

The cellular potency of compounds is determined by measuring phosphorylation of FGFR or FGFR downstream effectors Fibroblast growth factor receptor substrate 2 (FRS2) and extracellular-signal-regulated kinase (ERK) in cell lines with FGFR2/3 alterations.

To measure phosphorylated Fibroblast growth factor receptor, Fibroblast growth factor receptor substrate 2 (FRS2) and extracellular-signal-regulated kinase (ERK) cells (details regarding the cell lines and types of data produced are further detailed in Table 4) are seeded in 6 well plates overnight in 10% FBS and RPMI medium at $5-7.5 \times 10^5$ cells/well into Corning 6-well tissue culture treated plates. The next morning, 2 ml of fresh media with 10% FBS is incubated in the presence or absence of a concentration range of test compounds for 4 hours at 37° C., 5% CO2. Cells are washed with PBS and lysed with Cell Signaling Lysis Buffer with standard Protease inhibitors. 20-40 μg of total protein lysates are applied to western blot analysis using antibodies: phosphor-FRS2 Tyr436 (AF5126) from R&D Systems (Minneapolis, MN)), phosphor-FGFR-Tyr653/654 (#2476S), phospho-ERK1/2-Thr202/Tyr204 (#9101L) and total-ERK1/2 (#9102L) from Cell Signaling Technologies (Danvers, MA)).

TABLE 4

| Cell line | Histology | FGFR2/3 alteration | Readout |
|---|---|---|---|
| RT-112/84 | Bladder | FGFR3-TACC3 | pFRS2, pERK |
| RT112 V555M | Bladder | FGFR3-TACC3 V555M | pFRS2, pERK |

TABLE 4-continued

| Cell line | Histology | FGFR2/3 alteration | Readout |
|---|---|---|---|
| UM-UC-14 | Bladder | FGFR3 S249C | pFRS2, pERK |
| KMS-11 | Multiple Myeloma | IgH-FGFR3 translocation + FGFR3 Y373C | pFRS2, pERK |
| KATO-III | Stomach | FGFR2 amplification | pFGFR, pERK |
| SNU-16 | Stomach | FGFR2 amplification | pFGFR, pERK |

Example G: Activity on In Vivo Tumor Models Harboring FGFR2/3 Alteration

In vivo activity of compounds is determined by measuring tumor growth when treated with various doses of compounds in FGFR2/3 altered models.

RT112/84 tumor cells (85061106, ECACC, UK) are maintained as recommended by the source (tumor models are further detailed in Table 5). On Day 0 of the experiments, $2.0 \times 10^6$ RT112/84 cells are inoculated with a 1:1 PBS to Matrigel (354263, Coning) subcutaneously into the right hind flank of female NSG mice (Jackson). Treatment with compounds at 0 (Vehicle). 100 mg/kg, 30 mg/kg or 10 mg/kg PO QD is initiated on Day 7 after tumor inoculation, when tumors averaged approximately 200 mm, and is continued until the end of study. Mice are monitored for tumor growth and overt tolerability over the course of the experiment. Tumor volume is calculated using the formula $(L \times W^2)/2$, where L and W refer to the length and width dimensions, respectively. Tumor growth inhibition (TGI) is calculated using the formula $(1-(V_T/V_C))*100$ where $V_T$ is the tumor volume of the treatment group on the last day of treatment, and $V_C$ is the tumor volume of the control group on the last day of treatment. One-way ANOVA is used to determine statistical differences between treatment groups at the end of the study.

TABLE 5

| Tumor model | Histology | FGFR2/3 alteration |
|---|---|---|
| RT-112/84 | Bladder | FGFR3-TACC3 |
| RT112 V555M | Bladder | FGFR3-TACC3 V555M |
| UM-UC-14 | Bladder | FGFR3 S249C |
| KMS-11 | Multiple Myeloma | IgH-FGFR3 translocation + FGFR3 Y373C |
| KATO-III | Stomach | FGFR2 amplification |
| SNU-16 | Stomach | FGFR2 amplification |
| Ba/F3-TEL-FGFR3 V555M | Engineered system | TEL-FGFR3 V555M |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound selected from:
(2-(2,6-Dichlorophenyl)-9-(1-(pyrimidin-4-ylmethyl)-1H-pyrazol-4-yl)imidazo[2,1-f][1,6]naphthyridin-3-yl)methanol;
5-((4-(2-(2,6-Dichlorophenyl)-3-(hydroxymethyl)imidazo[2,1-f][1,6]naphthyridin-9-yl)-1H-pyrazol-1-yl)methyl)nicotinonitrile;
5-((4-(2-(2,6-Dichlorophenyl)-3-(hydroxymethyl)imidazo[2,1-f][1,6]naphthyridin-9-yl)-1H-pyrazol-1-yl)methyl)picolinonitrile;
4-((4-(2-(2,6-Dichlorophenyl)-3-(hydroxymethyl)imidazo[2,1-f][1,6]naphthyridin-9-yl)-1H-pyrazol-1-yl)methyl)picolinonitrile;
(2-(2,6-Dichlorophenyl)-9-(1-((2-(trifluoromethyl)pyridin-4-yl)methyl)-1H-pyrazol-4-yl)imidazo[2,1-f][1,6]naphthyridin-3-yl)methanol;
(4-(2-(2,6-Dichlorophenyl)-3-(hydroxymethyl)imidazo[2,1-f][1,6]naphthyridin-9-yl)phenyl)(morpholino)methanone;
((1S,4S)-2-Oxa-5-azabicyclo[2.2.1]heptan-5-yl) (4-(2-(2,6-dichlorophenyl)-3-(hydroxymethyl)imidazo[2,1-f][1,6]naphthyridin-9-yl)phenyl)methanone;
1-(4-(4-(2-(2,6-Dichlorophenyl)-3-(hydroxymethyl)imidazo[2,1-f][1,6]naphthyridin-9-yl)benzyl)piperazin-1-yl)-2-hydroxyethan-1-one;
1-(4-(4-(2-(2,6-Dichlorophenyl)-3-(hydroxymethyl)imidazo[2,1-f][1,6]naphthyridin-9-yl)benzyl)piperazin-1-yl)ethan-1-one;
1-(4-(4-(2-(2,6-Dichlorophenyl)-3-(hydroxymethyl)imidazo[2,1-f][1,6]naphthyridin-9-yl)phenyl)piperazin-1-yl)-2-hydroxyethan-1-one;
(2-(2-Chloro-6-methylphenyl)-9-(1-(1-methylpiperidin-4-yl)-1H-pyrazol-4-yl)imidazo[2,1-f][1,6]naphthyridin-3-yl)methanol;
5-((4-(2-(2,6-Dichlorophenyl)-3-(hydroxymethyl)imidazo[2,1-f][1,6]naphthyridin-9-yl)-1H-pyrazol-1-yl)methyl)-N,N-dimethylpicolinamide;
(3-(4-(2-(2,6-Dichlorophenyl)-3-methylimidazo[2,1-f][1,6]naphthyridin-9-yl)-1H-pyrazol-1-yl)azetidin-1-yl)(1-methyl-1H-1,2,3-triazol-4-yl) methanone;
(3-(4-(2-(2,6-Dichlorophenyl)-3-methylimidazo[2,1-f][1,6]naphthyridin-9-yl)-1H-pyrazol-1-yl)azetidin-1-yl)(2-methyl-2H-tetrazol-5-yl) methanone;
(2-(2,6-Dichlorophenyl)-9-(1-ethyl-1H-pyrazol-4-yl)imidazo[2,1-f][1,6]naphthyridin-3-yl)methanol;
2-(4-(2-(2,6-Dichlorophenyl)-3-(hydroxymethyl)imidazo[2,1-f][1,6]naphthyridin-9-yl)-1H-pyrazol-1-yl)-2-methylpropanenitrile;
2-(4-(2-(2,6-Dichlorophenyl)-3-(hydroxymethyl)imidazo[2,1-f][1,6]naphthyridin-9-yl)-1H-pyrazol-1-yl)propanenitrile;
1-(4-(2-(2,6-Dichlorophenyl)-3-(hydroxymethyl)imidazo[2,1-f][1,6]naphthyridin-9-yl)-1H-pyrazol-1-yl)propan-2-ol;
2-(4-(2-(2,6-Dichlorophenyl)-3-(hydroxymethyl)imidazo[2,1-f][1,6]naphthyridin-9-yl)-1H-pyrazol-1-yl)-N,N-dimethylacetamide;
1-(4-(4-(2-(2,6-Dichlorophenyl)-3-(hydroxymethyl)imidazo[2,1-f][1,6]naphthyridin-9-yl)-1H-pyrazol-1-yl)piperidin-1-yl)ethan-1-one;
1-(4-(4-(2-(2-Chloro-6-methylphenyl)-3-(hydroxymethyl)imidazo[2,1-f][1,6]naphthyridin-9-yl)-1H-pyrazol-1-yl)piperidin-1-yl)-2-methoxyethan-1-one;
1-(4-(2-(2-Chloro-6-methylphenyl)-3-(hydroxymethyl)imidazo[2,1-f][1,6]naphthyridin-9-yl)-1H-pyrazol-1-yl)-2-methylpropan-2-ol;
3-(4-(2-(2,6-Dichlorophenyl)-3-(hydroxymethyl)imidazo[2,1-f][1,6]naphthyridin-9-yl)-1H-pyrazol-1-yl)butanenitrile;
(R)-2-(4-(2-(2,6-Dichlorophenyl)-3-(hydroxymethyl)imidazo[2,1-f][1,6]naphthyridin-9-yl)-1H-pyrazol-1-yl)propan-1-ol;
(2-(2,6-Dichlorophenyl)-9-(1-((4-fluorotetrahydro-2H-pyran-4-yl)methyl)-1H-pyrazol-4-yl)imidazo[2,1-f][1,6]naphthyridin-3-yl)methanol;
3-(4-(2-(2,6-Dichlorophenyl)-3-(hydroxymethyl)imidazo[2,1-f][1,6]naphthyridin-9-yl)-1H-pyrazol-1-yl)tetrahydro-2H-thiopyran 1,1-dioxide;
1-(3-((4-(2-(2,6-Dichlorophenyl)-3-(hydroxymethyl)imidazo[2,1-f][1,6]naphthyridin-9-yl)-1H-pyrazol-1-yl)methyl)azetidin-1-yl)-2-methoxyethan-1-one;
2-(2,6-Dichlorophenyl)-3-(difluoromethyl)-9-(1-(2-(methylsulfonyl)ethyl)-1H-pyrazol-4-yl)imidazo[2,1-f][1,6]naphthyridine;
2-(4-(2-(2,6-Dichlorophenyl)-3-(difluoromethyl)imidazo[2,1-f][1,6]naphthyridin-9-yl)-1H-pyrazol-1-yl)acetonitrile;
2-(2,6-Dichlorophenyl)-3-(difluoromethyl)-9-(1-(tetrahydro-2H-pyran-4-yl)-1H-pyrazol-4-yl)imidazo[2,1-f][1,6]naphthyridine;
2-(4-(2-(2,6-Dichlorophenyl)-3-(difluoromethyl)imidazo[2,1-f][1,6]naphthyridin-9-yl)-1H-pyrazol-1-yl)ethan-1-ol;
2-(4-(2-(2,6-Dichlorophenyl)-3-(difluoromethyl)imidazo[2,1-f][1,6]naphthyridin-9-yl)-1H-pyrazol-1-yl)propanenitrile;
2-(4-(2-(2,6-Dichlorophenyl)-3-(difluoromethyl)imidazo[2,1-f][1,6]naphthyridin-9-yl)-1H-pyrazol-1-yl)-2-methylpropanamide;

2-(2-(2,6-Dichlorophenyl)-9-(1-(1-methylpiperidin-4-yl)-1H-pyrazol-4-yl)imidazo[2,1-f][1,6]naphthyridin-3-yl)ethan-1-ol; and 2-(2,6-Dichlorophenyl)-9-(1-(tetrahydro-2H-pyran-4-yl)-1H-pyrazol-4-yl)imidazo[2,1-f][1,6]naphthyridin-3-amine, or a pharmaceutically salt of any of the aforementioned.

2. A pharmaceutical composition comprising a compound of claim 1 or a pharmaceutically acceptable salt thereof, and a pharmaceutically acceptable carrier or excipient.

* * * * *

UNITED STATES PATENT AND TRADEMARK OFFICE
CERTIFICATE OF CORRECTION

PATENT NO. : 12,428,420 B2
APPLICATION NO. : 17/835330
DATED : September 30, 2025
INVENTOR(S) : Robert Swyka et al.

Page 1 of 1

It is certified that error appears in the above-identified patent and that said Letters Patent is hereby corrected as shown below:

In the Claims

Column 85, Line 38, Claim 1, delete "yl) (4-" and insert -- yl)(4- --;

Column 85, Lines 58-59, Claim 1, delete "yl) (1-" and insert -- yl)(1- --;

Column 85, Line 59, Claim 1, delete "yl) methanone;" and insert -- yl)methanone; --;

Column 85, Lines 61-62, Claim 1, delete "yl) (2-" and insert -- yl)(2- --;

Column 85, Line 62, Claim 1, delete "yl) methanone;" and insert -- yl)methanone; --;

Column 86, Lines 27-28, Claim 1, delete "yl) piperidin" and insert -- yl)piperidin --.

Signed and Sealed this
Eleventh Day of November, 2025

John A. Squires
*Director of the United States Patent and Trademark Office*

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthesized peptide substrate

<400> SEQUENCE: 1

Glu Gln Glu Asp Glu Pro Glu Gly Asp Tyr Phe Glu Trp Leu Glu
1               5                   10                  15